United States Patent
Glezer et al.

(10) Patent No.: US 12,123,054 B2
(45) Date of Patent: *Oct. 22, 2024

(54) METHODS FOR LONG READ SEQUENCING

(71) Applicant: Singular Genomics Systems, Inc., La Jolla, CA (US)

(72) Inventors: Eli N. Glezer, Del Mar, CA (US); Abrehet Abdu, San Diego, CA (US); Timothy Looney, Austin, TX (US)

(73) Assignee: Singular Genomics Systems, Inc., San Diego, CA (US)

( * ) Notice: Subject to any disclaimer, the term of this patent is extended or adjusted under 35 U.S.C. 154(b) by 239 days.

This patent is subject to a terminal disclaimer.

(21) Appl. No.: 17/545,226

(22) Filed: Dec. 8, 2021

(65) Prior Publication Data

US 2022/0170092 A1 Jun. 2, 2022

Related U.S. Application Data

(63) Continuation of application No. 17/127,308, filed on Dec. 18, 2020, now Pat. No. 11,225,688.

(60) Provisional application No. 62/953,028, filed on Dec. 23, 2019.

(51) Int. Cl.
*C12Q 1/68* (2018.01)
*C12Q 1/6869* (2018.01)

(52) U.S. Cl.
CPC ................... *C12Q 1/6869* (2013.01)

(58) Field of Classification Search
CPC ................................... C12Q 1/6869
See application file for complete search history.

(56) References Cited

U.S. PATENT DOCUMENTS

| | | |
|---|---|---|
| 5,034,506 A | 7/1991 | Summerton et al. |
| 5,235,033 A | 8/1993 | Summerton et al. |
| 5,302,509 A | 4/1994 | Cheeseman |
| 5,599,675 A | 2/1997 | Brenner |
| 5,750,341 A | 5/1998 | Macevicz |
| 5,763,594 A | 6/1998 | Hiatt et al. |
| 5,808,045 A | 9/1998 | Hiatt et al. |
| 5,872,244 A | 2/1999 | Hiatt et al. |
| 6,013,445 A | 1/2000 | Albrecht et al. |
| 6,232,465 B1 | 5/2001 | Hiatt et al. |
| 6,255,475 B1 | 7/2001 | Kwiatkowski |
| 6,664,079 B2 | 12/2003 | Ju et al. |
| 7,057,026 B2 | 6/2006 | Barnes et al. |
| 7,211,390 B2 | 5/2007 | Rothberg et al. |
| 7,244,559 B2 | 7/2007 | Rothberg et al. |
| 7,264,929 B2 | 9/2007 | Rothberg et al. |
| 7,541,444 B2 | 6/2009 | Milton et al. |
| 8,143,030 B2 | 3/2012 | Maxham et al. |
| 8,703,461 B2 | 4/2014 | Peris et al. |
| 8,882,980 B2 | 11/2014 | Ling et al. |
| 9,416,409 B2 | 8/2016 | Hayden |
| 10,738,072 B1 | 8/2020 | Graham et al. |
| 11,225,688 B2 * | 1/2022 | Glezer ................. C12Q 1/6869 |
| 2005/0191698 A1 | 9/2005 | Chee et al. |
| 2010/0279882 A1 | 11/2010 | Ronaghi et al. |
| 2010/0323350 A1 | 12/2010 | Gordon et al. |
| 2013/0281306 A1 | 10/2013 | Rigatti et al. |
| 2017/0029883 A1 | 2/2017 | Zhao et al. |
| 2017/0044601 A1 | 2/2017 | Cmogorac |
| 2020/0131484 A1 | 4/2020 | Golynskiy et al. |
| 2020/0181587 A1 | 6/2020 | Klausing et al. |
| 2020/0199666 A1 | 6/2020 | Gatti-Lafranconi et al. |
| 2020/0232024 A1 | 7/2020 | Esfandyarpour et al. |
| 2020/0377937 A1 * | 12/2020 | Pratt ................... C12Q 1/6827 |
| 2021/0054442 A1 | 2/2021 | Pratt et al. |
| 2021/0189481 A1 | 6/2021 | Glezer et al. |

FOREIGN PATENT DOCUMENTS

| | | |
|---|---|---|
| WO | WO-96/07669 A1 | 3/1996 |
| WO | WO-2004/018497 A2 | 3/2004 |
| WO | WO-2004/018497 A3 | 3/2004 |
| WO | WO-2008/069973 A2 | 6/2008 |
| WO | WO-2008/069973 A3 | 6/2008 |
| WO | WO-2008/069973 A8 | 6/2008 |
| WO | WO-2009/097626 A2 | 8/2009 |
| WO | WO-2010/127304 A2 | 11/2010 |
| WO | WO-2018/148723 A1 | 8/2018 |
| WO | WO-2018/165207 A1 | 9/2018 |
| WO | WO-2019/156910 A1 | 8/2019 |
| WO | WO-2020/056044 A1 | 3/2020 |
| WO | WO-2020/126595 A1 | 6/2020 |
| WO | WO-2020/227161 A1 | 11/2020 |
| WO | WO-2021/133685 A1 | 7/2021 |

OTHER PUBLICATIONS

International Preliminary Report on Patentability mailed Sep. 12, 2023 for PCT/US2022/020776, filed Mar. 17, 2022, 9 pages.
International Search Report mailed Aug. 12, 2022 for PCT Application No. PCT/US2022/020776, filed Mar. 17, 2022, 4 pages.
Sawada, J. et al. (Jan. 6, 2016, e-published Aug. 27, 2015). "A surprisingly simple de Bruijn sequence construction," *Discrete Mathematics* 339(1): 127-131.
Written Opinion mailed Aug. 12, 2022 for PCT Application No. PCT/US2022/020776, filed Mar. 17, 2022, 8 pages.
Extended European Search Report mailed on Jun. 27, 2023, for EP Application No. 20907550.6, 6 pages.
Bains, I. et al. (May 28, 2009) "Quantifying the development of the peripheral naive CD4+ T-cell pool in humans," *Blood* 113(22):5480-5487.
Baker G.C. et al. (2003). "Review and re-analysis of domain-specific 16S primers," J Microbiological Methods 55:541-555.

(Continued)

*Primary Examiner* — Jezia Riley
(74) *Attorney, Agent, or Firm* — Mintz, Levin, Cohn, Ferris, Glovsky, Popeo, P.C.; Zachary L. Terranova

(57) ABSTRACT

Provided herein are methods including alternating series of sequencing cycles and dark extension cycles allowing longer read lengths and addressing disadvantages of traditional nucleic acid sequencing protocols.

35 Claims, 9 Drawing Sheets

Specification includes a Sequence Listing.

(56) References Cited

OTHER PUBLICATIONS

Bentley, D.R. et al. (Nov. 6, 2008). "Accurate whole human genome sequencing using reversible terminator chemistry," *Nature* 456(7218):53-59.

Bergen, K. et al. (Jun. 17, 2013, e-published Jun. 3, 2013). "Structures of KOD and 9°N DNA polymerases complexed with primer template duplex," *Chembiochem* 14(9):1058-1062.

Campbell, M.A .et al. (Dec. 2006). "Comprehensive analysis of alternative splicing in rice and comparative analyses with *Arabidopsis*," *BMC Genomics* 7:327.

Chakravorty, S., et al. (May 2007, e-published Feb. 22, 2007). "A detailed analysis of 16S ribosomal RNA gene segments for the diagnosis of pathogenic bacteria," *J Microbiological Methods* 69(2):330-339.

De Koning, A.P.J. et al. (Dec. 2011). "Repetitive elements may comprise over two-thirds of the human genome," *PLoS Genet* 7(12):e100238.

Deininger, P. et al. (Dec. 28, 2011). "Alu elements: know the SINEs," Genome Biology 12:236.

Dubrovina A.S. et al. (2013, e-published Dec. 26, 2012). "The role of canonical and noncanonical pre-mRNA splicing in plant stress responses," *Biomed. Res. Int.* 2013:264314.

Foltz, S.M. et al. (May 29, 2020). "Evolution and structure of clinically relevant gene fusions in multiple myeloma," *Nature Comm.* 11(1):2666.

Fuller, C.W. et al. (May 10, 2016, e-published Apr. 18, 2016). "Real-time single-molecule electronic DNA sequencing by synthesis using polymer-tagged nucleotides on a nanopore array," *PNAS USA* 113(19):5233-5238.

Ganusov, V.V. et al. (Dec. 2007, e-published Oct. 26, 2007). "Do most lymphocytes in humans really reside in the gut?" *Trends Immunol.* 28(12):514-518.

Guo, J. et al. (Jul. 8, 2008, e-published Jun. 30, 2008). "Four-color DNA sequencing with 3'-O-modified nucleotide reversible terminators and chemically cleavable fluorescent dideoxynucleotides," *PNAS USA* 105(27):9145-9150.

Hu, H. et al. (Feb. 7, 2020). "Analysis of Alternative Splicing and Alternative Polyadenylation in *Populus alba* var. pyramidalis by Single-Molecular Long-Read Sequencing," *Front. Genet.* 11:48.

International Search Report mailed on Mar. 23, 2021, for PCT Application No. PCT/US2020/066109, filed Dec. 18, 2020, 5 pages.

Ju, J. et al. (Dec. 26, 2006, e-published Dec. 14, 2006). "Four-color DNA sequencing by synthesis using cleavable fluorescent nucleotide reversible terminators," *PNAS USA* 103(52):19635-19640.

Kumar, S. et al. (2012, e-published Sep. 21, 2012). "PEG-labeled nucleotides and nanopore detection for single molecule DNA sequencing by synthesis," *Sci Rep* 2:684.

Li, Y. et al. (Apr. 2017, e-published Feb. 11, 2017). "Global identification of alternative splicing via comparative analysis of SMRT- and Illumina-based RNA-seq in strawberry," *The Plant J.* 90(1):164-176.

Liao, X et al. (2019). "Current challenges and solutions of de novo assembly," *Quant. Biol.* 7(2):90-109.

Liao, Y.C. et al. (Sep. 4, 2019). "Completing Circular Bacterial Genomes With Assembly Complexity by Using a Sampling Strategy From a Single MinION Run With Barcoding," *Front. Microbiol.* 10:2068.

Shendure,J et al. (Sep. 9, 2005, e-published Aug. 4, 2005). "Accurate multiplex polony sequencing of an evolved bacterial genome," *Science* 309(5741):1728-1732.

Southworth, M.W. et al. (May 28, 1996). "Cloning of thermostable DNA polymerases from hyperthermophilic marine Archaea with emphasis on *Thermococcus* sp. 9°N-7 and mutations affecting 3'-5' exonuclease activity," *PNAS USA* 93(11):5281-5285.

Wahl, M.C. et al. (Feb. 20, 2009). "The spliceosome: design principles of a dynamic RNP machine," *Cell* 136(4):701-718.

Wang, Q. et al. (Aug. 28, 2018, e-published Aug. 13, 2018). "JUM is a computational method for comprehensive annotation-free analysis of alternative pre-mRNA splicing patterns," *PNAS USA.* 115(35):E8181-E8190.

Wang, Y. et al. (Mar. 3, 2014). "Optimal eukaryotic 18S and universal 16S/18S ribosomal RNA primers and their application in a study of symbiosis," *PloS One* 9(3):e90053.

Written Opinion mailed on Mar. 23, 2021, for PCT Application No. PCT/US2020/066109, filed Dec. 18, 2020, 7 pages.

Yaari, G. et al. (Nov. 20, 2015). "Practical guidelines for B-cell receptor repertoire sequencing analysis," *Genome Med.* 2015;7:121.

Zhao, S. et al. (Mar. 19, 2018). "Evaluation of two main RNA-seq approaches for gene quantification in clinical RNA sequencing: polyA+ selection versus rRNA depletion," *Scientific Reports* 8(1): 4781.

\* cited by examiner

Template nucleic acid:
CGTGACCCTCAGGTGATGCGCCAGGGCCGGCTGCCGTCGGGGACAGGGCTTTCCATAGCCATGGCCCA Interval sequenced nucleic acid:

Traditional sequencing: 32 nucleotides identified from a 32-mer template in 32 sequencing cycles

- one nucleotide extension
- dark extension

Interval sequencing: 32 nucleotides identified from an 88-mer template in 32 sequencing cycles Interval sequencing in parallel:

3'MeSS_dATP

3'MeSS_dTTP

3'MeSS_dCTP

3'MeSS_dGTP

```
                             SEQUENCE LISTING

<160> NUMBER OF SEQ ID NOS: 10

<210> SEQ ID NO 1
<211> LENGTH: 116
<212> TYPE: DNA
<213> ORGANISM: Artificial Sequence
<220> FEATURE:
<223> OTHER INFORMATION: Synthetic construct

<400> SEQUENCE: 1
gcttccttgc tggtcagatt ggtcgtctta ttaccatttc aactactccg gttatcgctg      60
gcgactcctt cgagatggac gccgttggcg ctctccgtct ttctccattg cgtcgt        116

<210> SEQ ID NO 2
<211> LENGTH: 193
<212> TYPE: DNA
<213> ORGANISM: Artificial Sequence
<220> FEATURE:
<223> OTHER INFORMATION: Synthetic construct

<400> SEQUENCE: 2
attgttcgcg tttaccttgc gtgtacgcgc aggaaacact gacgttctta ctgacgcaga      60
agaaaacgtg cgtcaaaaat tacgtgcgga aggagtgatg taatgtctaa aggtaaaaaa     120
cgttctggcg ctcgccctgg tcgtccgcag ccgttgcgag gtactaaagg caagcgtaaa     180
ggcgctcgtc ttt                                                        193

<210> SEQ ID NO 3
<211> LENGTH: 297
<212> TYPE: DNA
<213> ORGANISM: Artificial Sequence
<220> FEATURE:
<223> OTHER INFORMATION: Synthetic construct

<400> SEQUENCE: 3
tgacatttta aaagagcgtg gattactatc tgagtccgat gctgttcaac cactaatagg      60
taagaaatca tgagtcaagt tactgaacaa tccgtacgtt tccagaccgc tttggcctct     120
```

```
attaagctca ttcaggcttc tgccgttttg gatttaaccg aagatgattt cgattttctg    180
acgagtaaca aagtttggat tgctactgac cgctctcgtg ctcgtcgctg cgttgaggct    240
tgcgtttatg gtacgctgga ctttgtggga tacCctcgct ttcctgctcc tgttgag      297
```

<210> SEQ ID NO 4
<211> LENGTH: 394
<212> TYPE: DNA
<213> ORGANISM: Artificial Sequence
<220> FEATURE:
<223> OTHER INFORMATION: Synthetic construct

<400> SEQUENCE: 4

```
tcaagatgat gctcgttatg gtttccgttg ctgccatctc aaaaacattt ggactgctcc    60
gcttcctcct gagactgagc tttctcgcca aatgacgact tctaccacat ctattgacat    120
tatgggtctg caagctgctt atgctaattt gcatactgac caagaacgtg attacttcat    180
gcagcgttac catgatgtta tttcttcatt tggaggtaaa acctcttatg acgctgacaa    240
ccgtccttta cttgtcatgc gctctaatct ctgggcatct ggctatgatg ttgatggaac    300
tgaccaaacg tcgttaggcc agttttctgg tcgtgttcaa cagacctata acattctgt     360 gccgcgtttc tttgttcctg agcatggcac tatg                                394
```

<210> SEQ ID NO 5
<211> LENGTH: 277
<212> TYPE: DNA
<213> ORGANISM: Artificial Sequence
<220> FEATURE:
<223> OTHER INFORMATION: Synthetic construct

<400> SEQUENCE: 5

```
cgttcgtcaa ggactggttt agatatgagt cacattttgt tcatggtaga gattctcttg    60
ttgacatttt aaaagagcgt ggattactat ctgagtccga tgctgttcaa ccactaatag    120
gtaagaaatc atgagtcaag ttactgaaca atccgtacgt ttccagaccg ctttggcctc    180
tattaagctc attcaggctt ctgccgtttt ggatttaacc gaagatgatt tcgattttct    240
gacgagtaac aaagtttgga ttgctactga ccgctct                             277
```

<210> SEQ ID NO 6
<211> LENGTH: 259
<212> TYPE: DNA
<213> ORGANISM: Artificial Sequence
<220> FEATURE:
<223> OTHER INFORMATION: Synthetic construct

<400> SEQUENCE: 6

```
cctttcgcca tcaactaacg attctgtcaa aaactgacgc gttggatgag gagaagtggc    60
ttaatatgct tggcacgttc gtcaaggact ggtttagata tgagtcacat tttgttcatg    120
gtagagattc tcttgttgac attttaaaag agcgtggatt actatctgag tccgatgctg    180
ttcaaccact aataggtaag aaatcatgag tcaagttact gaacaatccg tacgtttcca    240
gaccgctttg gcctctatt                                                  259
```

<210> SEQ ID NO 7
<211> LENGTH: 291
<212> TYPE: DNA
<213> ORGANISM: Artificial Sequence
<220> FEATURE:
<223> OTHER INFORMATION: Synthetic construct

```
-continued

<400> SEQUENCE: 7
ctgccgtttt ggatttaacc gaagatgatt tcgattttct gacgagtaac aaagtttgga    60
ttgctactga ccgctctcgt gctcgtcgct gcgttgaggc ttgcgtttat ggtacgctgg   120
actttgtggg ataccctcgc tttcctgctc ctgttgagtt tattgctgcc gtcattgctt   180
attatgttca tcccgtcaac attcaaacgg cctgtctcat catggaaggc gctgaattta   240
cggaaaacat tattaatggc gtcgagcgtc cggttaaagc cgctgaattg t            291

<210> SEQ ID NO 8
<211> LENGTH: 398
<212> TYPE: DNA
<213> ORGANISM: Artificial Sequence
<220> FEATURE:
<223> OTHER INFORMATION: Synthetic construct

<400> SEQUENCE: 8
acattcaaac ggcctgtctc atcatggaag gcgctgaatt tacggaaaac attattaatg    60
gcgtcgagcg tccggttaaa gccgctgaat tgttcgcgtt taccttgcgt gtacgcgcag   120
gaaacactga cgttcttact gacgcagaag aaaacgtgcg tcaaaaatta cgtgcggaag   180
gagtgatgta atgtctaaag gtaaaaaacg ttctggcgct cgccctggtc gtccgcagcc   240
gttgcgaggt actaaaggca agcgtaaagg cgctcgtctt tggtatgtag gtggtcaaca   300
attttaattg caggggcttc ggccccttac ttgaggataa attatgtcta atattcaaac   360
tggcgccgag cgtatgccgc atgacctttc ccatcttg                          398

<210> SEQ ID NO 9
<211> LENGTH: 68
<212> TYPE: DNA
<213> ORGANISM: Artificial Sequence
<220> FEATURE:
<223> OTHER INFORMATION: Synthetic construct

<400> SEQUENCE: 9
cgtgaccctc aggtgatgcg ccagggccgg ctgccgtcgg ggacagggct ttccatagcc    60
atggccca                                                            68

<210> SEQ ID NO 10
<211> LENGTH: 10
<212> TYPE: DNA
<213> ORGANISM: Artificial Sequence
<220> FEATURE:
<223> OTHER INFORMATION: Synthetic construct

<400> SEQUENCE: 10
tatatatata                                                          10
```

METHODS FOR LONG READ SEQUENCING

CROSS-REFERENCES TO RELATED APPLICATIONS

This application claims the benefit of U.S. Provisional Application No. 62/953,028, filed Dec. 23, 2019, which is incorporated herein by reference in its entirety and for all purposes.

SEQUENCE LISTING

The instant application contains a Sequence Listing which has been submitted electronically in ASCII format and is hereby incorporated by reference in its entirety. Said ASCII copy, created on Dec. 14, 2020, is named 051385-519001US_SL_ST25.txt and is 4,732 byes in size.

BACKGROUND

DNA sequencing is a fundamental tool in biological and medical research; it is an essential technology for the paradigm of personalized precision medicine. Sanger sequencing, where the sequence of a nucleic acid is determined by selective incorporation and detection of dideoxynucleotides, enabled the mapping of the first human reference genome. While this methodology is still useful for validating newer sequencing technologies, efforts to sequence and assemble genomes using the Sanger method are an expensive and laborious undertaking, requiring specialized equipment and expertise. Certain new sequencing methodologies make use of simultaneously sequencing millions of fragments of nucleic acids, resulting in a 50,000-fold drop in the costs associated with sequencing. Due to the relatively short length of the fragments of nucleic acids, ranging in length from 35 to 600 base pairs, nucleic acid sequencing technologies may struggle with accurately mapping homopolymeric sequences, detecting single nucleotide polymorphism (SNP) regions, or identifying rare mutations.

Traditional sequencing-by-synthesis (SBS) methodologies employ serial incorporation and detection of labeled nucleotide analogues. For example, high-throughput SBS technology uses cleavable fluorescent nucleotide reversible terminator (NRT) sequencing chemistry. These cleavable fluorescent NRTs were designed based on the following rationale: each of the four nucleotides (A, C, G, T, and/or U) is modified by attaching a unique cleavable fluorophore to the specific location of the nucleobase and capping the 3'-OH group of the nucleotide sugar with a small reversible moiety (also referred to herein as a reversible terminator) so that they are still recognized by DNA polymerase as substrates. The reversible terminator temporarily halts the polymerase reaction after nucleotide incorporation while the fluorophore signal is detected. After incorporation and signal detection, the fluorophore and the reversible terminator are cleaved to resume the polymerase reaction in the next cycle.

These traditional SBS techniques have proved themselves incredibly valuable, however they require de novo assembly of relatively short lengths of DNA (e.g., 50 to 200 base pairs), which makes resolving complex regions with mutations or repetitive sequences difficult.

SUMMARY

In view of the foregoing, innovative approaches to address issues with existing sequencing technologies are needed. Disclosed herein are solutions to these and other problems in the art.

In an aspect, provided herein are methods of sequencing a template nucleic acid, including (a) executing a sequencing cycle that includes (i) extending a complementary polynucleotide that is hybridized to the template nucleic acid by incorporating a first nucleotide using a polymerase; and (ii) detecting a label that identifies the first nucleotide; (b) extending the complementary polynucleotide in one or more dark cycles, where each dark cycle includes extending the complementary polynucleotide by one or more nucleotides using the polymerase, without performing a detection event to identify nucleotides incorporated during the dark cycle; and (c) executing a sequencing cycle that includes (i) extending the complementary polynucleotide by incorporating a second nucleotide using a polymerase; and (ii) detecting a label that identifies the second nucleotide, thereby sequencing a template nucleic acid.

In an aspect, provided herein are methods of sequencing a template nucleic acid, including (a) executing one or more sequencing cycles that include (i) an extension step, where a complementary polynucleotide that is hybridized to the template nucleic acid is extended by incorporating a first nucleotide using a polymerase; and (ii) a detection step, where a characteristic signature is detected that identifies the first nucleotide; (b) extending the complementary polynucleotide in one or more dark cycles, where each dark cycle includes extending the complementary polynucleotide by one or more nucleotides using the polymerase, omitting a detection step to identify nucleotides incorporated during the dark cycle; and (c) executing one or more sequencing cycles that include (i) an extension step, where a complementary polynucleotide is extended by incorporating a second nucleotide using a polymerase; and (ii) a detection step, where a characteristic signature is detected that identifies the second nucleotide, thereby sequencing a template nucleic acid.

In an aspect, provided herein are methods of sequencing a template nucleic acid, the method including (a) executing a sequencing cycle including (i) extending a complementary polynucleotide that is hybridized to the template nucleic acid by incorporating a first nucleotide using a polymerase; where said nucleotide includes a reversible terminator moiety, and (ii) detecting a label that identifies the first nucleotide; (b) extending the complementary polynucleotide in one or more dark cycles, where each dark cycle includes extending the complementary polynucleotide by at least two nucleotides using the polymerase; wherein at least one nucleotide does not comprise a reversible terminator, and one nucleotide comprises a reversible terminator moiety, optionally performing a detection event to identify nucleotides incorporated during the dark cycle; and (c) executing a sequencing cycle including (i) extending the complementary polynucleotide by incorporating a second nucleotide using a polymerase; wherein said nucleotide comprises a reversible terminator moiety, and (ii) detecting a label that identifies the second nucleotide, thereby sequencing a template nucleic acid.

In an aspect, provided herein are methods of sequencing a template nucleic acid, the method including (a) executing a sequencing cycle including (i) extending a complementary polynucleotide that is hybridized to the template nucleic acid by incorporating a first nucleotide using a polymerase; where said nucleotide includes a reversible terminator moiety, and (ii) detecting a characteristic signature indicating that the first nucleotide has been incorporated; (b) extending the complementary polynucleotide in one or more dark cycles, where each dark cycle includes extending the complementary polynucleotide by exposing the complementary polynucleotide to two or more nucleotides in the presence of a polymerase; wherein at least one nucleotide does not comprise a reversible terminator, and at least one nucleotide comprises a reversible terminator moiety, optionally performing a detection event to identify nucleotides incorporated during the dark cycle; and (c) executing a sequencing cycle including (i) extending the complementary polynucleotide by incorporating a second nucleotide using a polymerase; wherein said nucleotide comprises a reversible terminator moiety, and (ii) detecting a characteristic signature indicating that the second nucleotide has been incorporated, thereby sequencing a template nucleic acid.

In an aspect, provided herein are kits including labeled nucleotides including four or fewer differently labeled nucleotides, where the label identifies the type of nucleotide, unlabeled nucleotides lacking a reversible terminator; and unlabeled nucleotides including a reversible terminator.

In an aspect, provided herein are reaction mixtures including labeled nucleotides including four or fewer differently labeled nucleotides, where the label identifies the type of nucleotide, unlabeled nucleotides lacking a reversible terminator; unlabeled nucleotides including a reversible terminator; and a polymerase.

BRIEF DESCRIPTION OF THE DRAWINGS

FIG. 3A illustrates a traditional sequencing method which provides information on the identity of every nucleotide incorporated into the extension strand across a 32-mer template, as compared to interval sequencing of 32 sequenced nucleotides across intervals spanning an 88-mer template. FIG. 3B illustrates interval sequencing in accordance with an embodiment, which alternates between sequencing and dark cycle reactions. Furthermore, the sequencing and dark (i.e. limited-extension) reaction conditions may be varied and run in parallel (FIG. 3B) so as to gather information about the entire template. In embodiments, interval sequencing permits sequencing of longer template nucleic acids for the same amount of sequencing time and aids in alignment.

FIG. 4A illustrates 3'MeSS_dATP and 3'MeSS_dTTP. FIG. 4B illustrates 3'MeSS_dCTP and 3'MeSS_dGTP.

FIG. 5B shows the results of sequencing cycles and resulting reads, which may then be aligned to show sufficient coverage of the V-D-J-constant regions. FIG. 5C depicts an illustration of the variable (V), diversity (D), joining (J) and constant/isotype region of an expressed, rearranged IGH receptor, including the membrane domain located at the 3' end of the constant gene. Alternative splicing of membrane exons determines whether the translated receptor is membrane bound or secreted as an immunoglobulin. In embodiments, interval sequencing methods described herein allows one to determine the membrane exon and isotype, bypass a majority of the constant gene, then obtain the sequence of the variable portion of the antibody.

DETAILED DESCRIPTION

Figure 1:
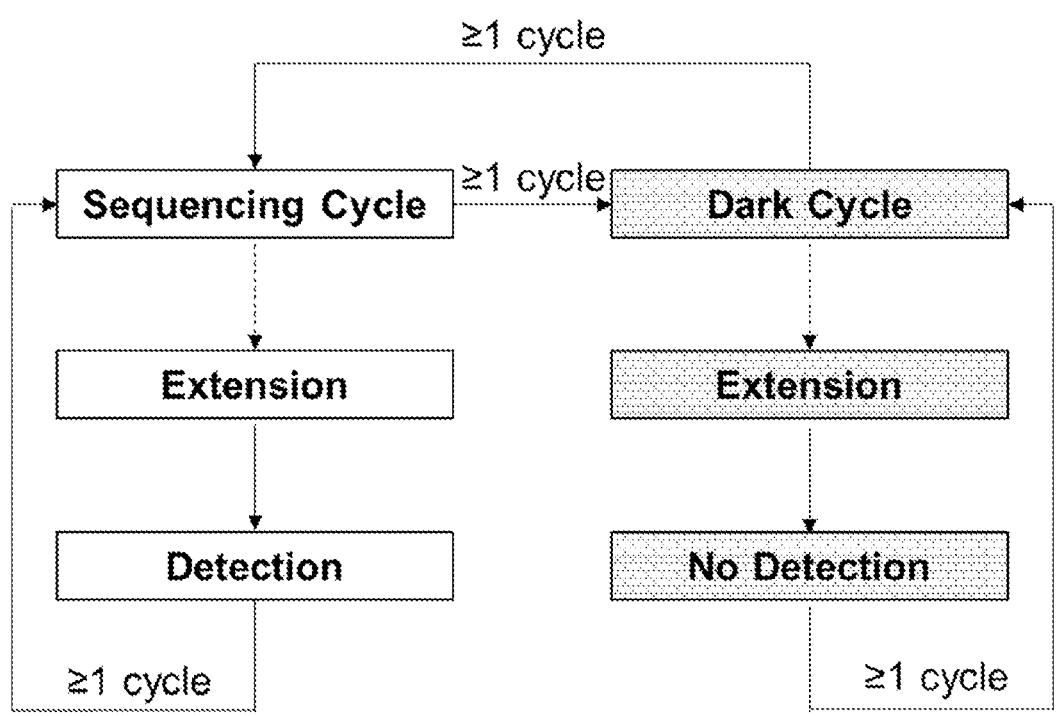
FIG. 1 depicts an embodiment of the invention in which sequencing comprises one or more sequencing cycles, where each sequencing cycle comprises polynucleotide extension and subsequent detection of an incorporated nucleotide. The one or more sequencing cycles are then followed by one or more dark cycles, where each dark cycle comprises polynucleotide extension without detection of an incorporated nucleotide. Following the dark cycle, the process may repeat with another sequencing cycle, and optionally another dark cycle.

The practice of the technology described herein will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Examples of such techniques are available in the literature. Methods, devices and materials similar or equivalent to those described herein can be used in the practice of this invention.

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise.

Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein, the term "control" or "control experiment" is used in accordance with its plain and ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

As used herein, the term "complement" is used in accordance with its plain and ordinary meaning and refers to a nucleotide (e.g., RNA nucleotide or DNA nucleotide) or a sequence of nucleotides capable of base pairing with a complementary nucleotide or sequence of nucleotides. As described herein and commonly known in the art the complementary (matching) nucleotide of adenosine is thymidine in DNA, or alternatively in RNA the complementary (matching) nucleotide of adenosine is uracil, and the complementary (matching) nucleotide of guanosine is cytosine. Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence. "Duplex" means at least two oligonucleotides and/or polynucleotides that are fully or partially complementary undergo Watson-Crick type base pairing among all or most of their nucleotides so that a stable complex is formed.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, sequences in a pair of complementary sequences form portions of a single polynucleotide with non-base-pairing nucleotides (e.g., as in a hairpin structure, with or without an overhang) or portions of separate polynucleotides. In embodiments, one or both sequences in a pair of complementary sequences form portions of longer polynucleotides, which may or may not include additional regions of complementarity.

As used herein, the term "contacting" is used in accordance with its plain ordinary meaning and refers to the process of allowing at least two distinct species (e.g. chemical compounds including biomolecules or cells) to become sufficiently proximal to react, interact or physically touch.

However, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound, nucleic acid, a protein, or enzyme (e.g., a DNA polymerase).

As used herein, the term "nucleic acid" is used in accordance with its plain and ordinary meaning and refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a sequence of nucleotides. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA with linear or circular framework. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences. A "nucleoside" is structurally similar to a nucleotide, but is missing the phosphate moieties. An example of a nucleoside analogue would be one in which the label is linked to the base and there is no phosphate group attached to the sugar molecule. As may be used herein, the terms "nucleic acid oligomer" and "oligonucleotide" are used interchangeably and are intended to include, but are not limited to, nucleic acids having a length of 200 nucleotides or less. In some embodiments, an oligonucleotide is a nucleic acid having a length of 2 to 200 nucleotides, 2 to 150 nucleotides, 5 to 150 nucleotides or 5 to 100 nucleotides.

The term "primer," as used herein, is defined to be one or more nucleic acid fragments that may specifically hybridize to a nucleic acid template, be bound by a polymerase, and be extended in a template-directed process for nucleic acid synthesis. A primer can be of any length depending on the particular technique it will be used for. For example, PCR primers are generally between 10 and 40 nucleotides in length. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. The length and complexity of the nucleic acid fixed onto the nucleic acid template is not critical to the invention. One of skill can adjust these factors to provide optimum hybridization and signal production for a given hybridization procedure, and to provide the required resolution among different genes or genomic locations. The primer permits the addition of a nucleotide residue thereto, or oligonucleotide or polynucleotide synthesis therefrom, under suitable conditions well-known in the art. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment the primer is an RNA primer. In embodiments, a primer is hybridized to a target polynucleotide. A "primer" comprises a sequence that is complementary to a polynucleotide template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

As used herein, the terms "solid support" and "substrate" and "solid surface" refers to discrete solid or semi-solid surfaces to which a plurality of primers may be attached. A solid support may encompass any type of solid, porous, or hollow sphere, ball, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. Solid supports in the form of discrete particles may be referred to herein as "beads," which alone does not imply or require any particular shape. A bead can be non-spherical in shape. A solid support may further comprise a polymer or hydrogel on the surface to which the primers are attached (e.g., the splint primers are covalently attached to the polymer, wherein the polymer is in direct contact with the solid support). Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor, silica or silica-based materials including silicon and modified silicon, carbon, metals, inorganic glasses, optical fiber bundles, photopatternable dry film resists, UV-cured adhesives and polymers. The solid supports for some embodiments have at least one surface located within a flow cell. The solid support, or regions thereof, can be substantially flat. The solid support can have surface features such as wells, pits, channels, ridges, raised regions, pegs, posts or the like. The term solid support is encompassing of a substrate (e.g., a flow cell) having a surface comprising a polymer coating covalently attached thereto. In embodiments, the solid support is a flow cell. The term "flow cell" as used herein refers to a chamber including a solid surface across which one or more fluid reagents can be flowed. Examples of flow cells and related fluidic systems and detection platforms that can be readily used in the methods of the present disclosure are described, for example, in Bentley et al., Nature 456:53-59 (2008).

In some embodiments, a nucleic acid comprises a capture nucleic acid. A capture nucleic acid refers to a nucleic acid that is attached to a substrate (e.g., covalently attached). In some embodiments, a capture nucleic acid comprises a primer. In some embodiments, a capture nucleic acid is a nucleic acid configured to specifically hybridize to a portion of one or more nucleic acid templates (e.g., a template of a library). In some embodiments a capture nucleic acid configured to specifically hybridize to a portion of one or more nucleic acid templates is substantially complementary to a suitable portion of a nucleic acid template, or an amplicon thereof. In some embodiments a capture nucleic acid is configured to specifically hybridize to a portion of an adapter, or a portion thereof. In some embodiments a capture nucleic acid, or portion thereof, is substantially complementary to a portion of an adapter, or a complement thereof. In embodiments, a capture nucleic acid is a probe oligonucleotide. Typically, a probe oligonucleotide is complementary to a target polynucleotide or portion thereof, and further comprises a label (such as a binding moiety) or is attached to a surface, such that hybridization to the probe oligonucleotide permits the selective isolation of probe-bound polynucleotides from unbound polynucleotides in a population. A probe oligonucleotide may or may not also be used as a primer.

Nucleic acids, including e.g., nucleic acids with a phosphothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent, or other interaction.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the term "template nucleic acid" refers to any polynucleotide molecule that may be bound by a polymerase and utilized as a template for nucleic acid synthesis. A template nucleic acid may be a target nucleic acid. In general, the term "target nucleic acid" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. A target nucleic acid is not necessarily any single molecule or sequence. For example, a target nucleic acid may be any one of a plurality of target nucleic acids in a reaction, or all nucleic acids in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target nucleic acid in a reaction with the corresponding primer polynucleotide(s). In the context of selective sequencing, "target nucleic acid(s)" refers to the subset of nucleic acid(s) to be sequenced from within a starting population of nucleic acids.

In embodiments, a target nucleic acid is a cell-free nucleic acid. In general, the terms "cell-free," "circulating," and "extracellular" as applied to nucleic acids (e.g. "cell-free DNA" (cfDNA) and "cell-free RNA" (cfRNA)) are used interchangeably to refer to nucleic acids present in a sample from a subject or portion thereof that can be isolated or otherwise manipulated without applying a lysis step to the sample as originally collected (e.g., as in extraction from cells or viruses). Cell-free nucleic acids are thus unencapsulated or "free" from the cells or viruses from which they originate, even before a sample of the subject is collected. Cell-free nucleic acids may be produced as a byproduct of cell death (e.g. apoptosis or necrosis) or cell shedding, releasing nucleic acids into surrounding body fluids or into circulation. Accordingly, cell-free nucleic acids may be isolated from a non-cellular fraction of blood (e.g. serum or plasma), from other bodily fluids (e.g. urine), or from non-cellular fractions of other types of samples.

As used herein, the terms "analogue" and "analog", in reference to a chemical compound, refers to compound having a structure similar to that of another one, but differing from it in respect of one or more different atoms, functional groups, or substructures that are replaced with one or more other atoms, functional groups, or substructures. In the context of a nucleotide, a "nucleotide analog" and "modified nucleotide" refer to a compound that, like the nucleotide of which it is an analog, can be incorporated into a nucleic acid molecule (e.g., an extension product) by a suitable polymerase, for example, a DNA polymerase in the context of a nucleotide analogue. The terms also encompass nucleic acids containing known nucleotide analogs or modified backbone residues or linkages, which are synthetic, naturally occurring, or non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, e.g., see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

As used herein, a "native" nucleotide is used in accordance with its plain and ordinary meaning and refers to a naturally occurring nucleotide that does not include an exogenous label (e.g., a fluorescent dye, or other label) or chemical modification such as those that may characterize a nucleotide analog (e.g., a reversible terminating moiety). Examples of native nucleotides useful for carrying out procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate).

As used herein, the term "modified nucleotide" refers to a nucleotide modified in some manner. Typically, a nucleotide contains a single 5-carbon sugar moiety, a single nitrogenous base moiety and 1 to three phosphate moieties. In embodiments, a nucleotide can include a blocking moiety (alternatively referred to herein as a reversible terminator moiety) and/or a label moiety. A blocking moiety on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. In embodiments, the blocking moiety is attached to the 3' oxygen of the nucleotide and is independently —NH$_2$, —CN, —CH$_3$, C$_2$-C$_6$ allyl (e.g., —CH$_2$—CH=CH$_2$), methoxyalkyl (e.g., —CH$_2$—O—CH$_3$), or —CH$_2$N$_3$. In embodiments, the blocking moiety is attached to the 3' oxygen of the nucleotide and is independently

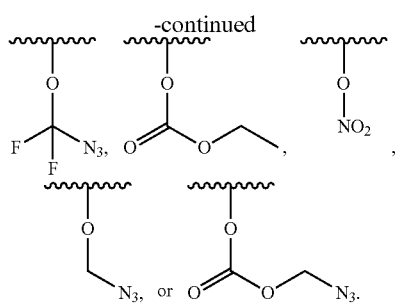

A label moiety of a nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both. Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the —OH group at the 3'-position of deoxyribose. Nucleotide analogues and DNA polymerase-based DNA sequencing are also described in U.S. Pat. No. 6,664,079, which is incorporated herein by reference in its entirety for all purposes.

Figure 3A:
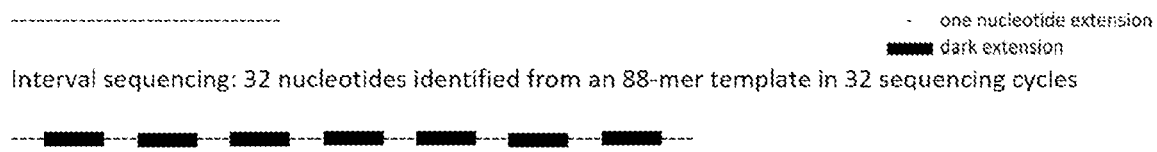
FIGS. 3A-3B illustrate a comparison of interval sequencing with traditional sequencing methods.
Figure 3A:
Figure 3B:
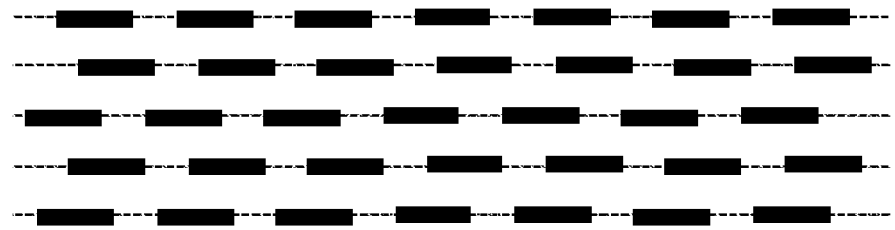

In embodiments, the nucleotides of the present disclosure use a cleavable linker to attach the label to the nucleotide. The use of a cleavable linker ensures that the label can, if required, be removed after detection, avoiding any interfering signal with any labelled nucleotide incorporated subsequently. The use of the term "cleavable linker" is not meant to imply that the whole linker is required to be removed from the nucleotide base. The cleavage site can be located at a position on the linker that ensures that part of the linker remains attached to the nucleotide base after cleavage. The linker can be attached at any position on the nucleotide base provided that Watson-Crick base pairing can still be carried out. In the context of purine bases, it is preferred if the linker is attached via the 7-position of the purine or the preferred deazapurine analogue, via an 8-modified purine, via an N-6 modified adenosine or an N-2 modified guanine. For pyrimidines, attachment is preferably via the 5-position on cytidine, thymidine or uracil and the N-4 position on cytosine. Suitable nucleotide structures having cleavable linkers are shown in FIGS. 3A-3B, however any suitable linker possessing a cleavable moiety may be used.

The term "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite (Na$_2$S$_2$O$_4$), or hydrazine (N$_2$H$_4$)). A chemically cleavable linker is non-enzymatically cleavable. In embodiments, the cleavable linker is cleaved by contacting the cleavable linker with a cleaving agent. In embodiments, the cleaving agent is a phosphine containing reagent (e.g., TCEP or THPP), sodium dithionite (Na$_2$S$_2$O$_4$), weak acid, hydrazine (N$_2$H$_4$), Pd(0), or light-irradiation (e.g., ultraviolet radiation).

As used herein, the term "removable" group, e.g., a label or a blocking group or protecting group, is used in accordance with its plain and ordinary meaning and refers to a chemical group that can be removed from a nucleotide analogue such that a DNA polymerase can extend the nucleic acid (e.g., a primer or extension product) by the incorporation of at least one additional nucleotide. Removal may be by any suitable method, including enzymatic, chemical, or photolytic cleavage. Removal of a removable group, e.g., a blocking group, does not require that the entire removable group be removed, only that a sufficient portion of it be removed such that a DNA polymerase can extend a nucleic acid by incorporation of at least one additional nucleotide using a nucleotide or nucleotide analogue.

As used herein, the terms "blocking moiety," "reversible blocking group," "reversible terminator" and "reversible terminator moiety" are used in accordance with their plain and ordinary meanings and refer to a cleavable moiety which does not interfere with incorporation of a nucleotide comprising it by a polymerase (e.g., DNA polymerase, modified DNA polymerase), but prevents further strand extension until removed ("unblocked"). For example, a reversible terminator may refer to a blocking moiety located, for example, at the 3' position of the nucleotide and may be a chemically cleavable moiety such as an allyl group, an azidomethyl group or a methoxymethyl group, or may be an enzymatically cleavable group such as a phosphate ester. Suitable nucleotide blocking moieties are described in applications WO 2004/018497, U.S. Pat. Nos. 7,057,026, 7,541,444, WO 96/07669, U.S. Pat. Nos. 5,763,594, 5,808,045, 5,872,244 and 6,232,465 the contents of which are incorporated herein by reference in their entirety. The nucleotides may be labelled or unlabeled. The nucleotides may be modified with reversible terminators useful in methods provided herein and may be 3'-O-blocked reversible or 3'-unblocked reversible terminators. In nucleotides with 3'-O-blocked reversible terminators, the blocking group may be represented as —OR [reversible terminating (capping) group], wherein 0 is the oxygen atom of the 3'-OH of the pentose and R is the blocking group, while the label is linked to the base, which acts as a reporter and can be cleaved. The 3'-O-blocked reversible terminators are known in the art, and may be, for instance, a 3'-ONH$_2$ reversible terminator, a 3'-O-allyl reversible terminator, or a 3'-O-azidomethyl reversible terminator. In embodiments, the reversible terminator moiety is

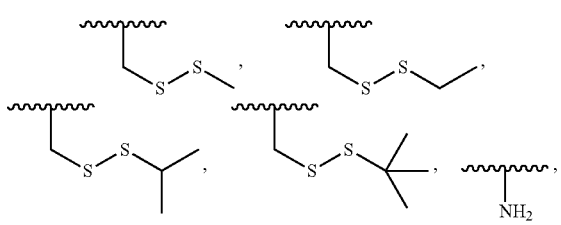

-continued

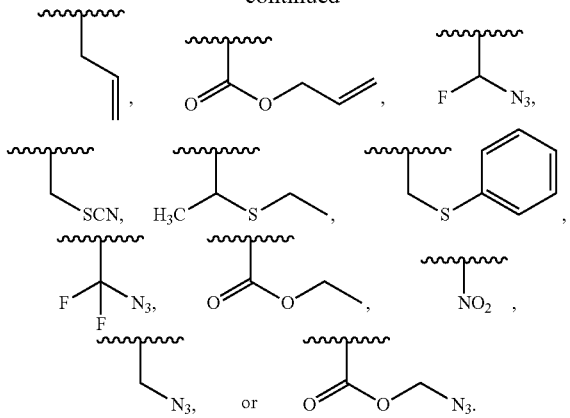

The term "allyl" as described herein refers to an unsubstituted methylene attached to a vinyl group (i.e., —CH═CH$_2$), having the formula

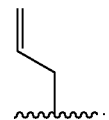

In embodiments, the reversible terminator moiety is

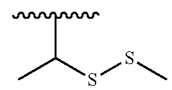 [SMILES: *C(C)SSC]

as described in U.S. Pat. No. 10,738,072, which is incorporated herein by reference for all purposes. For example, a nucleotide including a reversible terminator moiety may be represented by the formula:

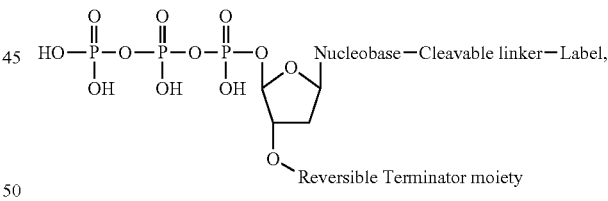

where the nucleobase is adenine or adenine analogue, thymine or thymine analogue, guanine or guanine analogue, or cytosine or cytosine analogue.

As used herein, the term "label" or "labels" is used in accordance with their plain and ordinary meanings and refer to molecules that can directly or indirectly produce or result in a detectable signal either by themselves or upon interaction with another molecule. Non-limiting examples of detectable labels include fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the label is a dye. In embodiments, the dye is a fluorescent dye. Non-limiting examples of dyes, some of which are commercially available, include CF dyes (Biotium, Inc.), Alexa Fluor dyes (Thermo Fisher), DyLight dyes (Thermo Fisher), Cy dyes (GE Healthscience), IRDyes (Li-Cor Biosciences, Inc.), and HiLyte dyes (Anaspec, Inc.). In embodiments, a particular nucleotide type is associated with a particular label, such that identifying the label identifies the nucleotide with which it is associated. In embodiments, the label is luciferin that reacts with luciferase to produce a detectable signal in response to one or more bases being incorporated into an elongated complementary strand, such as in pyrosequencing. In embodiment, a nucleotide comprises a label (such as a dye). In embodiments, the label is not associated with any particular nucleotide, but detection of the label identifies whether one or more nucleotides having a known identity were added during an extension step (such as in the case of pyrosequencing).

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals. The alkyl may include a designated number of carbons (e.g., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, homologs and isomers thereof, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkynyl moiety. An alkyl moiety may be fully saturated. An alkenyl may include more than one double bond and/or one or more triple bonds in addition to the one or more double bonds. An alkynyl may include more than one triple bond and/or one or more double bonds in addition to the one or more triple bonds.

Examples of detectable agents include imaging agents, including fluorescent and luminescent substances, including, but not limited to, a variety of organic or inorganic small molecules commonly referred to as "dyes," "labels," or "indicators." Examples include fluorescein, rhodamine, acridine dyes, Alexa dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescein isothiocyanate moiety, tetramethylrhodamine-5-(and 6)-isothiocyanate moiety, Cy2 moiety, Cy3 moiety, Cy5 moiety, Cy7 moiety, 4',6-diamidino-2-phenylindole moiety, Hoechst 33258 moiety, Hoechst 33342 moiety, Hoechst 34580 moiety, propidium-iodide moiety, or acridine orange moiety. In embodiments, the detectable moiety is a Indo-1, Ca saturated moiety, Indo-1 Ca2+ moiety, Cascade Blue BSA pH 7.0 moiety, Cascade Blue moiety, LysoTracker Blue moiety, Alexa 405 moiety, LysoSensor Blue pH 5.0 moiety, LysoSensor Blue moiety, DyLight 405 moiety, DyLight 350 moiety, BFP (Blue Fluorescent Protein) moiety, Alexa 350 moiety, 7-Amino-4-methylcoumarin pH 7.0 moiety, Amino Coumarin moiety, AMCA conjugate moiety, Coumarin moiety, 7-Hydroxy-4-methylcoumarin moiety, 7-Hydroxy-4-methylcoumarin pH 9.0 moiety, 6,8-Difluoro-7-hydroxy-4-methylcoumarin pH 9.0 moiety, Hoechst 33342 moiety, Pacific Blue moiety, Hoechst 33258 moiety, Hoechst 33258-DNA moiety, Pacific Blue antibody conjugate pH 8.0 moiety, PO-PRO-1 moiety, PO-PRO-1-DNA moiety, POPO-1 moiety, POPO-1-DNA moiety, DAPI-DNA moiety, DAPI moiety, Marina Blue moiety, SYTOX Blue-DNA moiety, CFP (Cyan Fluorescent Protein) moiety, eCFP (Enhanced Cyan Fluorescent Protein) moiety, 1-Anilinonaphthalene-8-sulfonic acid (1,8-ANS) moiety, Indo-1, Ca free moiety, 1,8-ANS (1-Anilinonaphthalene-8-sulfonic acid) moiety, BO-PRO-1-DNA moiety, BOPRO-1 moiety, BOBO-1-DNA moiety, SYTO 45-DNA moiety, evoglow-Pp1 moiety, evoglow-Bs1 moiety, evoglow-Bs2 moiety, Auramine 0 moiety, DiO moiety, LysoSensor Green pH 5.0 moiety, Cy 2 moiety, LysoSensor Green moiety, Fura-2, high Ca moiety, Fura-2 Ca2+sup> moiety, SYTO 13-DNA moiety, YO-PRO-1-DNA moiety, YOYO-1-DNA moiety, eGFP (Enhanced Green Fluorescent Protein) moiety, LysoTracker Green moiety, GFP (S65T) moiety, BODIPY FL, MeOH moiety, Sapphire moiety, BODIPY FL conjugate moiety, MitoTracker Green moiety, MitoTracker Green FM, MeOH moiety, Fluorescein 0.1 M NaOH moiety, Calcein pH 9.0 moiety, Fluorescein pH 9.0 moiety, Calcein moiety, Fura-2, no Ca moiety, Fluo-4 moiety, FDA moiety, DTAF moiety, Fluorescein moiety, CFDA moiety, FITC moiety, Alexa Fluor 488 hydrazide-water moiety, DyLight 488 moiety, 5-FAM pH 9.0 moiety, Alexa 488 moiety, Rhodamine 110 moiety, Rhodamine 110 pH 7.0 moiety, Acridine Orange moiety, BCECF pH 5.5 moiety, PicoGreendsDNA quantitation reagent moiety, SYBR Green I moiety, Rhodamine Green pH 7.0 moiety, CyQUANT GR-DNA moiety, NeuroTrace 500/525, green fluorescent Nissl stain-RNA moiety, DansylCadaverine moiety, Fluoro-Emerald moiety, Nissl moiety, Fluorescein dextran pH 8.0 moiety, Rhodamine Green moiety, 5-(and-6)-Carboxy-2',7'-dichlorofluorescein pH 9.0 moiety, DansylCadaverine, MeOH moiety, eYFP (Enhanced Yellow Fluorescent Protein) moiety, Oregon Green 488 moiety, Fluo-3 moiety, BCECF pH 9.0 moiety, SBFI-Na+ moiety, Fluo-3 Ca2+ moiety, Rhodamine 123 MeOH moiety, FlAsH moiety, Calcium Green-1 Ca2+ moiety, Magnesium Green moiety, DM-NERF pH 4.0 moiety, Calcium Green moiety, Citrine moiety, LysoSensor Yellow pH 9.0 moiety, TO-PRO-1-DNA moiety, Magnesium Green Mg2+ moiety, Sodium Green Na+ moiety, TOTO-1-DNA moiety, Oregon Green 514 moiety, Oregon Green 514 antibody conjugate pH 8.0 moiety, NBD-X moiety, DM-NERF pH 7.0 moiety, NBD-X, MeOH moiety, CI-NERF pH 6.0 moiety, Alexa 430 moiety, CI-NERF pH 2.5 moiety, Lucifer Yellow, CH moiety, LysoSensor Yellow pH 3.0 moiety, 6-TET, SE pH 9.0 moiety, Eosin antibody conjugate pH 8.0 moiety, Eosin moiety, 6-Carboxyrhodamine 6G pH 7.0 moiety, 6-Carboxyrhodamine 6G, hydrochloride moiety, Bodipy R6G SE moiety, BODIPY R6G MeOH moiety, 6 JOE moiety, Cascade Yellow moiety, mBanana moiety, Alexa 532 moiety, Erythrosin-5-isothiocyanate pH 9.0 moiety, 6-HEX, SE pH 9.0 moiety, mOrange moiety, mHoneydew moiety, Cy 3 moiety, Rhodamine B moiety, DiI moiety, 5-TAMRA-MeOH moiety, Alexa 555 moiety, DyLight 549 moiety, BODIPY TMR-X, SE moiety, BODIPY TMR-X MeOH moiety, PO-PRO-3-DNA moiety, PO-PRO-3 moiety, Rhodamine moiety, POPO-3 moiety, Alexa 546 moiety, Calcium Orange Ca2+ moiety, TRITC moiety, Calcium Orange moiety, Rhodaminephalloidin pH 7.0 moiety, MitoTracker Orange moiety, MitoTracker Orange MeOH moiety, Phycoerythrin moiety, Magnesium Orange moiety, R-Phycoerythrin pH 7.5 moiety, 5-TAMRA pH 7.0 moiety, 5-TAMRA moiety, Rhod-2 moiety, FM 1-43 moiety, Rhod-2 Ca2+ moiety, FM 1-43 lipid moiety, LOLO-1-DNA moiety, dTomato moiety, DsRed moiety, Dapoxyl (2-aminoethyl) sulfonamide moiety, Tetramethylrhodamine dextran pH 7.0 moiety, Fluor-Ruby moiety, Resorufin moiety, Resorufin pH 9.0 moiety, mTangerine moiety, LysoTracker Red moiety, Lissaminerhodamine moiety, Cy 3.5 moiety, Rhodamine Red-X antibody conjugate pH 8.0 moiety, Sulforhodamine 101 EtOH moiety, JC-1 pH 8.2 moiety, JC-1 moiety, mStrawberry moiety, MitoTracker Red moiety, MitoTracker Red, MeOH moiety, X-Rhod-1 Ca2+ moiety, Alexa 568 moiety, 5-ROX pH 7.0 moiety, 5-ROX (5-Carboxy-X-rhodamine, triethylammonium salt) moiety, BO-PRO-3-DNA moiety, BOPRO-3 moiety, BOBO-3-DNA moiety, Ethidium Bromide moiety, ReAsH moiety, Calcium Crimson moiety, Calcium Crimson Ca2+ moiety, mRFP moiety, mCherry moiety, HcRed moiety, DyLight 594 moiety, Ethidium homodimer-1-DNA moiety, Ethidium homodimer moiety, Propidium Iodide moiety, SYPRO Ruby moiety, Propidium Iodide-DNA moiety, Alexa 594 moiety, BODIPY TR-X, SE moiety, BODIPY TR-X, MeOH moiety, BODIPY TR-X phallacidin pH 7.0 moiety, Alexa Fluor 610 R-phycoerythrin streptavidin pH 7.2 moiety, YO-PRO-3-DNA moiety, Di-8 ANEPPS moiety, Di-8-ANEPPS-lipid moiety, YOYO-3-DNA moiety, Nile Red-lipid moiety, Nile Red moiety, DyLight 633 moiety, mPlum moiety, TO-PRO-3-DNA moiety, DDAO pH 9.0 moiety, Fura Red high Ca moiety, Allophycocyanin pH 7.5 moiety, APC (allophycocyanin) moiety, Nile Blue, EtOH moiety, TOTO-3-DNA moiety, Cy 5 moiety, BODIPY 650/665-X, MeOH moiety, Alexa Fluor 647 R-phycoerythrin streptavidin pH 7.2 moiety, DyLight 649 moiety, Alexa 647 moiety, Fura Red Ca2+ moiety, Atto 647 moiety, Fura Red, low Ca moiety, Carboxynaphthofluorescein pH 10.0 moiety, Alexa 660 moiety, Cy 5.5 moiety, Alexa 680 moiety, DyLight 680 moiety, Alexa 700 moiety, FM 4-64, 2% CHAPS moiety, or FM 4-64 moiety. In embodiments, the detectable moiety is a moiety of 1,1-Diethyl-4,4-carbocyanine iodide, 1,2-Diphenylacetylene, 1,4-Diphenylbutadiene, 1,4-Diphenylbutadiyne, 1,6-Diphenylhexatriene, 1,6-Diphenylhexatriene, 1-anilinonaphthalene-8-sulfonic acid, 2,7-Dichlorofluorescein, 2,5-DIPHENYLOXAZOLE, 2-Di-1-ASP, 2-dodecylresorufin, 2-Methylbenzoxazole, 3,3-Diethylthiadicarbocyanine iodide, 4-Dimethylamino-4-Nitrostilbene, 5(6)-Carboxyfluorescein, 5(6)-Carboxynaphtofluorescein, 5(6)-Carboxytetramethylrhodamine B, 5-(and-6)-carboxy-2',7'-dichlorofluorescein, 5-(and-6)-carboxy-2,7-dichlorofluorescein, 5-(N-hexadecanoyl)aminoeosin, 5-(N-hexadecanoyl)aminoeosin, 5-chloromethylfluorescein, 5-FAM, 5-ROX, 5-TAMRA, 5-TAMRA, 6,8-difluoro-7-hydroxy-4-methylcoumarin, 6,8-difluoro-7-hydroxy-4-methylcoumarin, 6-carboxyrhodamine 6G, 6-HEX, 6-JOE, 6-JOE, 6-TET, 7-aminoactinomycin D, 7-Benzylamino-4-Nitrobenz-2-Oxa-1,3-Diazole, 7-Methoxycoumarin-4-Acetic Acid, 8-Benzyloxy-5,7-diphenylquinoline, 8-Benzyloxy-5,7-diphenylquinoline, 9,10-Bis(Phenylethynyl) Anthracene, 9,10-Diphenylanthracene, 9-METHYLCARBAZOLE, (CS)2Ir(µ-Cl)$_2$Ir(CS)2, AAA, Acridine Orange, Acridine Orange, Acridine Yellow, Acridine Yellow, Adams Apple Red 680, Adirondack Green 520, Alexa Fluor 350, Alexa Fluor 405, Alexa Fluor 430, Alexa Fluor 430, Alexa Fluor 480, Alexa Fluor 488, Alexa Fluor 488, Alexa Fluor 488 hydrazide, Alexa Fluor 500, Alexa Fluor 514, Alexa Fluor 532, Alexa Fluor 546, Alexa Fluor 546, Alexa Fluor 555, Alexa Fluor 555, Alexa Fluor 568, Alexa Fluor 594, Alexa Fluor 594, Alexa Fluor 594, Alexa Fluor 610, Alexa Fluor 610-R-PE, Alexa Fluor 633, Alexa Fluor 635, Alexa Fluor 647, Alexa Fluor 647, Alexa Fluor 647-R-PE, Alexa Fluor 660, Alexa Fluor 680, Alexa Fluor 680-APC, Alexa Fluor 680-R-PE, Alexa Fluor 700, Alexa Fluor 750, Alexa Fluor 790, Allophycocyanin, AmCyan1, Aminomethylcoumarin, Amplex Gold (product), Amplex Red Reagent, Amplex UltraRed, Anthracene, APC, APC-Seta-750, AsRed2, ATTO 390, ATTO 425, ATTO 430LS, ATTO 465, ATTO 488, ATTO 490LS, ATTO 495, ATTO 514, ATTO 520, ATTO 532, ATTO 550, ATTO 565, ATTO 590, ATTO 594, ATTO 610, ATTO 620, ATTO 633, ATTO 635, ATTO 647, ATTO 647N, ATTO 655, ATTO 665, ATTO 680, ATTO 700, ATTO 725, ATTO 740, ATTO Oxa12, ATTO Rho3B, ATTO Rho6G, ATTO Rho11, ATTO Rho12, ATTO Rho13, ATTO Rho14, ATTO Rho101, ATTO Thio12, Auramine O, Azami Green, Azami Green monomeric, B-phycoerythrin, BCECF, BCECF, Bex1, Biphenyl, Birch Yellow 580, Blue-green algae, BO-PRO-1, BO-PRO-3, BOBO-1, BOBO-3, BODIPY 630 650-X, BODIPY 650/665-X, BODIPY FL, BODIPY FL, BODIPY R6G, BODIPY TMR-X, BODIPY TR-X, BODIPY TR-X Ph 7.0, BODIPY TR-X phallacidin, BODIPY-DiMe, BODIPY-Phenyl, BODIPY-TMSCC, C3-Indocyanine, C3-Indocyanine, C3-Oxacyanine, C3-Thiacyanine Dye (EtOH), C3-Thiacyanine Dye (PrOH), C5-Indocyanine, C5-Oxacyanine, C5-Thiacyanine, C7-Indocyanine, C7-Oxacyanine, C545T, C-Phycocyanin, Calcein, Calcein red-orange, Calcium Crimson, Calcium Green-1, Calcium Orange, Calcofluor white 2MR, Carboxy SNARF-1 pH 6.0, Carboxy SNARF-1 pH 9.0, Carboxynaphthofluorescein, Cascade Blue, Cascade Yellow, Catskill Green 540, CBQCA, CellMask Orange, CellTrace BODIPY TR methyl ester, CellTrace calcein violet, CellTrace™ Far Red, CellTracker Blue, CellTracker Red CMTPX, CellTracker Violet BMQC, CF405M, CF405S, CF488A, CF543, CF555, CFP, CFSE, CF™ 350, CF™ 485, Chlorophyll A, Chlorophyll B, Chromeo 488, Chromeo 494, Chromeo 505, Chromeo 546, Chromeo 642, Citrine, Citrine, ClOH butoxy aza-BODIPY, ClOH C12 aza-BODIPY, CM-H2DCFDA, Coumarin 1, Coumarin 6, Coumarin 6, Coumarin 30, Coumarin 314, Coumarin 334, Coumarin 343, Coumarine 545T, Cresyl Violet Perchlorate, CryptoLight CF1, CryptoLight CF2, CryptoLight CF3, CryptoLight CF4, CryptoLight CF5, CryptoLight CF6, Crystal Violet, Cumarin153, Cy2, Cy3, Cy3, Cy3.5, Cy3B, Cy3B, Cy3Cy5 ET, Cy5, Cy5, Cy5.5, Cy7, Cyanine3 NHS ester, Cyanine5 carboxylic acid, Cyanine5 NHS ester, Cyclotella meneghiniana Kützing, CypHer5, CypHer5 pH 9.15, CyQUANT GR, CyTrak Orange, Dabcyl SE, DAF-FM, DAMC (Weiss), dansyl cadaverine, Dansyl Glycine (Dioxane), DAPI, DAPI, DAPI, DAPI, DAPI (DMSO), DAPI (H2O), Dapoxyl (2-aminoethyl)sulfonamide, DCI, DCM, DCM, DCM (acetonitrile), DCM (MeOH), DDAO, Deep Purple, di-8-ANEPPS, DiA, Dichlorotris(1,10-phenanthroline) ruthenium(II), DiClOH C12 aza-BODIPY, DiClOHbutoxy aza-BODIPY, DiD, DiI, DiIC18(3), DiO, DiR, Diversa Cyan-FP, Diversa Green-FP, DM-NERF pH 4.0, DOCI, Doxorubicin, DPP pH-Probe 590-7.5, DPP pH-Probe 590-9.0, DPP pH-Probe 590-11.0, DPP pH-Probe 590-11.0, Dragon Green, DRAQ5, DsRed, DsRed, DsRed, DsRed-Express, DsRed-Express2, DsRed-Express T1, dTomato, DY-350XL, DY-480, DY-480XL MegaStokes, DY-485, DY-485XL MegaStokes, DY-490, DY-490XL MegaStokes, DY-500, DY-500XL MegaStokes, DY-520, DY-520XL MegaStokes, DY-547, DY-549P1, DY-549P1, DY-554, DY-555, DY-557, DY-557, DY-590, DY-590, DY-615, DY-630, DY-631, DY-633, DY-635, DY-636, DY-647, DY-649P1, DY-649P1, DY-650, DY-651, DY-656, DY-673, DY-675, DY-676, DY-680, DY-681, DY-700, DY-701, DY-730, DY-731, DY-750, DY-751, DY-776, DY-782, Dye-28, Dye-33, Dye-45, Dye-304, Dye-1041, DyLight 488, DyLight 549, DyLight 594, DyLight 633, DyLight 649, DyLight 680, E2-Crimson, E2-Orange, E2-Red/Green, EBFP, ECF, ECFP, ECL Plus, eGFP, ELF 97, Emerald, Envy Green, Eosin, Eosin Y, epicocconone, EqFP611, Erythrosin-5-isothiocyanate, Ethidium bromide, ethidium homodimer-1, Ethyl Eosin, Ethyl Eosin, Ethyl Nile Blue A, Ethyl-p-Dimethylaminobenzoate, Ethyl-p-Dimethylaminobenzoate, Eu2O3 nanoparticles, Eu (Soini), Eu(tta) 3DEADIT, EvaGreen, EVOblue-30, EYFP, FAD, FITC, FITC, FlAsH (Adams), Flash Red EX, FlAsH-CCPGCC, FlAsH-CCXXCC, Fluo-3, Fluo-4, Fluo-5F, Fluorescein, Fluorescein 0.1 NaOH, Fluorescein-Dibase, fluoro-emerald, Fluorol 5G, FluoSpheres blue, FluoSpheres crimson, FluoSpheres dark red, FluoSpheres orange, FluoSpheres red, FluoSpheres yellow-green, FM4-64 in CTC, FM4-64 in SDS, FM 1-43, FM 4-64, Fort Orange 600, Fura Red, Fura Red Ca free, fura-2, Fura-2 Ca free, Gadodiamide, Gd-Dtpa-Bma, Gadodiamide, Gd-Dtpa-Bma, GelGreen™, GelRed™, H9-40, HcRed1, Hemo Red 720, HiLyte Fluor 488, HiLyte Fluor 555, HiLyte Fluor 647, HiLyte Fluor 680, HiLyte Fluor 750, HiLyte Plus 555, HiLyte Plus 647, HiLyte Plus 750, HmGFP, Hoechst 33258, Hoechst 33342, Hoechst-33258, Hoechst-33258, Hops Yellow 560, HPTS, HPTS, HPTS, HPTS, HPTS, indo-1, Indo-1 Ca free, Ir(Cn)2(acac), Ir(Cs)2(acac), IR-775 chloride, IR-806, Ir-OEP-CO-C1, IRDye® 650 Alkyne, IRDye® 650 Azide, IRDye® 650 Carboxylate, IRDye® 650 DBCO, IRDye® 650 Maleimide, IRDye® 650 NHS Ester, IRDye® 680LT Carboxylate, IRDye® 680LT Maleimide, IRDye® 680LT NHS Ester, IRDye® 680RD Alkyne, IRDye® 680RD Azide, IRDye® 680RD Carboxylate, IRDye® 680RD DBCO, IRDye® 680RD Maleimide, IRDye® 680RD NHS Ester, IRDye® 700 phosphoramidite, IRDye® 700DX, IRDye® 700DX, IRDye® 700DX Carboxylate, IRDye® 700DX NHS Ester, IRDye® 750 Carboxylate, IRDye® 750 Maleimide, IRDye® 750 NHS Ester, IRDye® 800 phosphoramidite, IRDye® 800CW, IRDye® 800CW Alkyne, IRDye® 800CW Azide, IRDye® 800CW Carboxylate, IRDye® 800CW DBCO, IRDye® 800CW Maleimide, IRDye® 800CW NHS Ester, IRDye® 800RS, IRDye® 800RS Carboxylate, IRDye® 800RS NHS Ester, IRDye® QC-1 Carboxylate, IRDye® QC-1 NHS Ester, *Isochrysis galbana*-Parke, JC-1, JC-1, JOJO-1, Jonamac Red Evitag T2, Kaede Green, Kaede Red, kusabira orange, Lake Placid 490, LDS 751, Lissamine Rhodamine (Weiss), LOLO-1, lucifer yellow CH, Lucifer Yellow CH, lucifer yellow CH, Lucifer Yellow CH Dilitium salt, Lumio Green, Lumio Red, Lumogen F Orange, Lumogen Red F300, Lumogen Red F300, LysoSensor Blue DND-192, LysoSensor Green DND-153, LysoSensor Green DND-153, LysoSensor Yellow/Blue DND-160 pH 3, LysoSensor YellowBlue DND-160, LysoTracker Blue DND-22, LysoTracker Blue DND-22, LysoTracker Green DND-26, LysoTracker Red DND-99, LysoTracker Yellow HCK-123, Macoun Red Evitag T2, Macrolex Fluorescence Red G, Macrolex Fluorescence Yellow 10GN, Macrolex Fluorescence Yellow 10GN, Magnesium Green, Magnesium Octaethylporphyrin, Magnesium Orange, Magnesium Phthalocyanine, Magnesium Phthalocyanine, Magnesium Tetramesitylporphyrin, Magnesium Tetraphenylporphyrin, malachite green isothiocyanate, Maple Red-Orange 620, Marina Blue, mBanana, mBBr, mCherry, Merocyanine 540, Methyl green, Methyl green, Methyl green, Methylene Blue, Methylene Blue, mHoneyDew, MitoTracker Deep Red 633, MitoTracker Green FM, MitoTracker Orange CMTMRos, MitoTracker Red CMXRos, monobromobimane, Monochlorobimane, Monoraphidium, mOrange, mOrange2, mPlum, mRaspberry, mRFP, mRFP1, mRFP1.2 (Wang), mStrawberry (Shaner), mTangerine (Shaner), N,N-Bis(2,4,6-trimethylphenyl)-3,4:9,10-perylenebis(dicarboximide), NADH, Naphthalene, Naphthalene, Naphthofluorescein, Naphthofluorescein, NBD-X, NeuroTrace 500525, Nilblau perchlorate, nile blue, Nile Blue, Nile Blue (EtOH), nile red, Nile Red, Nile Red, Nile red, Nileblue A, NIR1, NIR2, NIR3, NIR4, NIR820, Octaethylporphyrin, OH butoxy aza-BODIPY, OHC12 aza-BODIPY, Orange Fluorescent Protein, Oregon Green 488, Oregon Green 488 DHPE, Oregon Green 514, Oxazinl, Oxazin 750, Oxazine 1, Oxazine 170, P4-3, P-Quaterphenyl, P-Terphenyl, PA-GFP (post-activation), PA-GFP (pre-activation), Pacific Orange, Palladium (II) meso-tetraphenyltetrabenzoporphyrin, PdOEPK, PdTFPP, PerCP-Cy5.5, Perylene, Perylene, Perylene bisimide pH-Probe 550-5.0, Perylene bisimide pH-Probe 550-5.5, Perylene bisimide pH-Probe 550-6.5, Perylene Green pH-Probe 720-5.5, Perylene Green Tag pH-Probe 720-6.0, Perylene Orange pH-Probe 550-2.0, Perylene Orange Tag 550, Perylene Red pH-Probe 600-5.5, Perylenediimid, Perylne Green pH-Probe 740-5.5, Phenol, Phenylalanine, pHrodo, succinimidyl ester, Phthalocyanine, PicoGreen dsDNA quantitation reagent, Pinacyanol-Iodide, Piroxicam, Platinum(II) tetraphenyltetrabenzoporphyrin, Plum Purple, PO-PRO-1, PO-PRO-3, POPO-1, POPO-3, POPOP, Porphin, PPO, Proflavin, PromoFluor-350, PromoFluor-405, PromoFluor-415, PromoFluor-488, PromoFluor-488 Premium, PromoFluor-488LSS, PromoFluor-500LSS, PromoFluor-505, PromoFluor-510LSS, PromoFluor-514LSS, PromoFluor-520LSS, PromoFluor-532, PromoFluor-546, PromoFluor-555, PromoFluor-590, PromoFluor-610, PromoFluor-633, PromoFluor-647, PromoFluor-670, PromoFluor-680, PromoFluor-700, PromoFluor-750, PromoFluor-770, PromoFluor-780, PromoFluor-840, propidium iodide, Protoporphyrin IX, PTIR475/UF, PTIR545/UF, PtOEP, PtOEPK, PtTFPP, Pyrene, QD525, QD565, QD585, QD605, QD655, QD705, QD800, QD903, QD PbS 950, QDot 525, QDot 545, QDot 565, Qdot 585, Qdot 605, Qdot 625, Qdot 655, Qdot 705, Qdot 800, QpyMe2, QSY 7, QSY 7, QSY 9, QSY 21, QSY 35, quinine, Quinine Sulfate, Quinine sulfate, R-phycoerythrin, R-phycoerythrin, ReAsH-CCPGCC, ReAsH-CCXXCC, Red Beads (Weiss), Redmond Red, Resorufin, resorufin, rhod-2, Rhodamin 700 perchlorate, rhodamine, Rhodamine 6G, Rhodamine 6G, Rhodamine 101, rhodamine 110, Rhodamine 123, rhodamine 123, Rhodamine B, Rhodamine B, Rhodamine Green, Rhodamine pH-Probe 585-7.0, Rhodamine pH-Probe 585-7.5, Rhodamine phalloidin, Rhodamine Red-X, Rhodamine Red-X, Rhodamine Tag pH-Probe 585-7.0, Rhodol Green, Riboflavin, Rose Bengal, Sapphire, SBFI, SBFI Zero Na, *Scenedesmus* sp., SensiLight PBXL-1, SensiLight PBXL-3, Seta 633-NHS, Seta-633-NHS, SeTau-380-NHS, SeTau-647-NHS, Snake-Eye Red 900, SNIR1, SNIR2, SNIR3, SNIR4, Sodium Green, Solophenyl flavine 7GFE 500, Spectrum Aqua, Spectrum Blue, Spectrum FRed, Spectrum Gold, Spectrum Green, Spectrum Orange, Spectrum Red, Squarylium dye III, Stains All, Stilben derivate, Stilbene, Styryl8 perchlorate, Sulfo-Cyanine3 carboxylic acid, Sulfo-Cyanine3 carboxylic acid, Sulfo-Cyanine3 NHS ester, Sulfo-Cyanine5 carboxylic acid, Sulforhodamine 101, sulforhodamine 101, Sulforhodamine B, Sulforhodamine G, Suncoast Yellow, SuperGlo BFP, SuperGlo GFP, Surf Green EX, SYBR Gold nucleic acid gel stain, SYBR Green I, SYPRO Ruby, SYTO 9, SYTO 11, SYTO 13, SYTO 16, SYTO 17, SYTO 45, SYTO 59, SYTO 60, SYTO 61, SYTO 62, SYTO 82, SYTO RNASelect, SYTO RNASelect, SYTOX Blue, SYTOX Green, SYTOX Orange, SYTOX Red, T-Sapphire, Tb (Soini), tCO, tdTomato, Terrylen, Terrylendiimid, testdye, Tetra-t-Butylazaporphine, Tetra-t-Butylnaphthalocyanine, Tetracen, Tetrakis(o-Aminophenyl)Porphyrin, Tetramesitylporphyrin, Tetramethylrhodamine, tetramethylrhodamine, Tetraphenylporphyrin, Tetraphenylporphyrin, Texas Red, Texas Red DHPE, Texas Red-X, ThiolTracker Violet, Thionin acetate, TMRE, TO-PRO-1, TO-PRO-3, Toluene, Topaz (Tsien1998), TOTO-1, TOTO-3, Tris(2,2-Bipyridyl)Ruthenium(II) chloride; Tris(4,4-diphenyl-2,2-bipyridine) ruthenium(II) chloride. Tris(4,7-diphenyl-1,10-phenanthroline) ruthenium(II) TMS, TRITC (Weiss), TRITC Dextran (Weiss), Tryptophan, Tyrosine, Vexl, Vybrant DyeCycle Green stain, Vybrant DyeCycle Orange stain, Vybrant DyeCycle Violet stain, WEGFP (post-activation), WellRED D2, WellRED D3, WellRED D4, WtGFP, WtGFP (Tsien1998), X-rhod-1, Yakima Yellow, YFP, YO-PRO-1, YO-PRO-3, YOYO-1, YoYo-1, YoYo-1 dsDNA, YoYo-1 ssDNA, YOYO-3, Zinc Octaethylporphyrin, Zinc Phthalocyanine, Zinc Tetramesitylporphyrin, Zinc Tetraphenylporphyrin, ZsGreen1, or ZsYellow1.

In embodiments, the detectable label is a fluorescent dye. In embodiments, the detectable label is a fluorescent dye capable of exchanging energy with another fluorescent dye (e.g., fluorescence resonance energy transfer (FRET) chromophores).

In embodiments, the detectable moiety is a moiety of a derivative of one of the detectable moieties described immediately above, wherein the derivative differs from one of the detectable moieties immediately above by a modification resulting from the conjugation of the detectable moiety to a compound described herein.

The term "cyanine" or "cyanine moiety" as described herein refers to a detectable moiety containing two nitrogen groups separated by a polymethine chain. In embodiments, the cyanine moiety has 3 methine structures (i.e. cyanine 3 or Cy3). In embodiments, the cyanine moiety has 5 methine structures (i.e. cyanine 5 or Cy5). In embodiments, the cyanine moiety has 7 methine structures (i.e. cyanine 7 or Cy7).

As used herein, the term "DNA polymerase" and "nucleic acid polymerase" are used in accordance with their plain ordinary meanings and refer to enzymes capable of synthesizing nucleic acid molecules from nucleotides (e.g., deoxyribonucleotides). Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol τ DNA polymerase, Pol κ DNA polymerase, Pol ζ DNA polymerase, Pol γ DNA polymerase, Pol θ DNA polymerase, Pol ν DNA polymerase, or a thermophilic nucleic acid polymerase (e.g. Therminator γ, 9° N polymerase (exo-), Therminator II, Therminator III, or Therminator IX). In embodiments, the DNA polymerase is a modified archaeal DNA polymerase. In embodiments, the polymerase is a reverse transcriptase. In embodiments, the polymerase is a mutant P. abyssi polymerase (e.g., such as a mutant P. abyssi polymerase described in WO 2018/148723 or WO 2020/056044).

As used herein, the term "thermophilic nucleic acid polymerase" refers to a family of DNA polymerases (e.g., 9° N™) and mutants thereof derived from the DNA polymerase originally isolated from the hyperthermophilic archaea, *Thermococcus* sp. 9 degrees N-7, found in hydrothermal vents at that latitude (East Pacific Rise) (Southworth M W, et al. *PNAS.* 1996; 93(11):5281-5285). A thermophilic nucleic acid polymerase is a member of the family B DNA polymerases. Site-directed mutagenesis of the 3'-5' exo motif I (Asp-Ile-Glu or DIE) to AIA, AIE, EIE, EID or DIA yielded polymerase with no detectable 3' exonuclease activity. Mutation to Asp-Ile-Asp (DID) resulted in reduction of 3'-5' exonuclease specific activity to <1% of wild type, while maintaining other properties of the polymerase including its high strand displacement activity. The sequence AIA (D141A, E143A) was chosen for reducing exonuclease. Subsequent mutagenesis of key amino acids results in an increased ability of the enzyme to incorporate dideoxynucleotides, ribonucleotides and acyclonucleotides (e.g., Therminator II enzyme from New England Biolabs with D141A/E143A/Y409V/A485L mutations); 3'-amino-dNTPs, 3'-azido-dNTPs and other 3'-modified nucleotides (e.g., NEB Terminator III DNA Polymerase with D141A/E143A/L408S/Y409A/P410V mutations, NEB Terminator IX DNA polymerase), or γ-phosphate labeled nucleotides (e.g., Terminator γ: D141A/E143A/W355A/L408W/R460A/Q461S/K464E/D480V/R484W/A485L). Typically, these enzymes do not have 5'-3' exonuclease activity. Additional information about thermophilic nucleic acid polymerases may be found in (Southworth M W, et al. *PNAS.* 1996; 93(11):5281-5285; Bergen K, et al. *Chem Bio Chem.* 2013; 14(9):1058-1062; Kumar S, et al. *Scientific Reports.* 2012; 2:684; Fuller C W, et al. 2016; 113(19):5233-5238; Guo J, et al. *Proceedings of the National Academy of Sciences of the United States of America.* 2008; 105(27): 9145-9150), which are incorporated herein in their entirety for all purposes.

As used herein, the term "exonuclease activity" is used in accordance with its ordinary meaning in the art, and refers to the removal of a nucleotide from a nucleic acid by a DNA polymerase. For example, during polymerization, nucleotides are added to the 3' end of the primer strand. Occasionally a DNA polymerase incorporates an incorrect nucleotide to the 3'-OH terminus of the primer strand, wherein the incorrect nucleotide cannot form a hydrogen bond to the corresponding base in the template strand. Such a nucleotide, added in error, is removed from the primer as a result of the 3' to 5' exonuclease activity of the DNA polymerase. In embodiments, exonuclease activity may be referred to as "proofreading." When referring to 3'-5' exonuclease activity, it is understood that the DNA polymerase facilitates a hydrolyzing reaction that breaks phosphodiester bonds at either the 3' end of a polynucleotide chain to excise the nucleotide. In embodiments, 3'-5' exonuclease activity refers to the successive removal of nucleotides in single-stranded DNA in a 3'→5' direction, releasing deoxyribonucleoside 5'-monophosphates one after another. Methods for quantifying exonuclease activity are known in the art, see for example Southworth et al, PNAS Vol 93, 8281-8285 (1996).

As used herein, the term "incorporating" or "chemically incorporating," when used in reference to a primer and cognate nucleotide, refers to the process of joining the cognate nucleotide to the primer or extension product thereof by formation of a phosphodiester bond.

As used herein, the term "selective" or "selectivity" or the like of a compound refers to the compound's ability to discriminate between molecular targets. When used in the context of sequencing, such as in "selectively sequencing," this term refers to sequencing one or more target polynucleotides from an original starting population of polynucleotides, and not sequencing non-target polynucleotides from the starting population. Typically, selectively sequencing one or more target polynucleotides involves differentially manipulating the target polynucleotides based on known sequence. For example, target polynucleotides may be hybridized to a probe oligonucleotide that may be labeled (such as with a member of a binding pair) or bound to a surface. In embodiments, hybridizing a target polynucleotide to a probe oligonucleotide includes the step of displacing one strand of a double-stranded nucleic acid. Probe-hybridized target polynucleotides may then be separated from non-hybridized polynucleotides, such as by removing probe-bound polynucleotides from the starting population or by washing away polynucleotides that are not bound to a probe. The result is a selected subset of the starting population of polynucleotides, which is then subjected to sequencing, thereby selectively sequencing the one or more target polynucleotides.

As used herein, the terms "specific", "specifically", "specificity", or the like of a compound refers to the compound's ability to cause a particular action, such as binding, to a particular molecular target with minimal or no action to other proteins in the cell.

As used herein, the terms "bind" and "bound" are used in accordance with their plain and ordinary meanings and refer to an association between atoms or molecules. The association can be direct or indirect. For example, bound atoms or molecules may be directly bound to one another, e.g., by a covalent bond or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). As a further example, two molecules may be bound indirectly to one another by way of direct binding to one or more intermediate molecules, thereby forming a complex.

As used herein, the terms "sequencing", "sequence determination", "determining a nucleotide sequence", and the like include determination of partial as well as full sequence information, including the identification, ordering, or locations of the nucleotides that comprise the polynucleotide being sequenced, and inclusive of the physical processes for generating such sequence information. That is, the term includes sequence comparisons, fingerprinting, and like levels of information about a target polynucleotide, as well as the express identification and ordering of nucleotides in a target polynucleotide. The term also includes the determination of the identification, ordering, and locations of one, two, or three of the four types of nucleotides within a target polynucleotide. Sequencing methods, such as those outlined in U.S. Pat. No. 5,302,509 can be carried out using the nucleotides described herein. The sequencing methods are preferably carried out with the target polynucleotide arrayed on a solid substrate. Multiple target polynucleotides can be immobilized on the solid support through linker molecules, or can be attached to particles, e.g., microspheres, which can also be attached to a solid substrate. The solid substrate is in the form of a chip, a bead, a well, a capillary tube, a slide, a wafer, a filter, a fiber, a porous media, or a column. This invention also provides the instant method, wherein the solid substrate is gold, quartz, silica, plastic, glass, diamond, silver, metal, or polypropylene. This invention also provides the instant method, wherein the solid substrate is porous.

As used herein, the term "sequencing reaction mixture" is used in accordance with its plain and ordinary meaning and refers to an aqueous mixture that contains the reagents necessary to allow a dNTP or dNTP analogue to add a nucleotide to a DNA strand by a DNA polymerase. In embodiments, the sequencing reaction mixture includes a buffer. In embodiments, the buffer includes an acetate buffer, 3-(N-morpholino) propanesulfonic acid (MOPS) buffer, N-(2-Acetamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP) buffer, 4-(Cyclohexylamino)-1-butanesulfonic acid (CABS) buffer, glycine-NaOH buffer, N-Cyclohexyl-2-aminoethanesulfonic acid (CHES) buffer, tris(hydroxymethyl)aminomethane (Tris) buffer, or a N-cyclohexyl-3-aminopropanesulfonic acid (CAPS) buffer. In embodiments, the buffer is a borate buffer. In embodiments, the buffer is a CHES buffer. In embodiments, the sequencing reaction mixture includes nucleotides, wherein the nucleotides include a reversible terminating moiety and a label covalently linked to the nucleotide via a cleavable linker. In embodiments, the sequencing reaction mixture includes a buffer, DNA polymerase, detergent (e.g., Triton X), a chelator (e.g., EDTA), or salts (e.g., ammonium sulfate, magnesium chloride, sodium chloride, or potassium chloride).

As used herein, the term "sequencing cycle" is used in accordance with its plain and ordinary meaning and refers to incorporating one or more nucleotides (e.g., nucleotide analogues) to the 3' end of a polynucleotide with a polymerase, and detecting one or more labels that identify the one or more nucleotides incorporated. The sequencing may be accomplished by, for example, sequencing by synthesis, pyrosequencing, and the like. In embodiments, a sequencing cycle includes extending a complementary polynucleotide by incorporating a first nucleotide using a polymerase, wherein the polynucleotide is hybridized to a template nucleic acid, detecting the first nucleotide, and identifying the first nucleotide. In embodiments, to begin a sequencing cycle, one or more differently labeled nucleotides and a DNA polymerase can be introduced. Following nucleotide addition, signals produced (e.g., via excitation and emission of a detectable label) can be detected to determine the identity of the incorporated nucleotide (based on the labels on the nucleotides). Reagents can then be added to remove the 3' reversible terminator and to remove labels from each incorporated base. Reagents, enzymes and other substances can be removed between steps by washing. Cycles may include repeating these steps, and the sequence of each cluster is read over the multiple repetitions.

"Hybridize" shall mean the annealing of one single-stranded nucleic acid (such as a primer) to another nucleic acid based on the well-understood principle of sequence complementarity. In an embodiment the other nucleic acid is a single-stranded nucleic acid. The propensity for hybridization between nucleic acids depends on the temperature and ionic strength of their milieu, the length of the nucleic acids and the degree of complementarity. The effect of these parameters on hybridization is described in, for example, Sambrook J., Fritsch E. F., Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith. For example, hybridization can be performed at a temperature ranging from 15° C. to 95° C. In some embodiments, the hybridization is performed at a temperature of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., or about 95° C. In other embodiments, the stringency of the hybridization can be further altered by the addition or removal of components of the buffered solution. In some embodiments nucleic acids, or portions thereof, that are configured to hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence. A specific hybridization discriminates over non-specific hybridization interactions (e.g., two nucleic acids that a not configured to specifically hybridize, e.g., two nucleic acids that are 80% or less, 70% or less, 60% or less or 50% or less complementary) by about 2-fold or more, often about 10-fold or more, and sometimes about 100-fold or more, 1000-fold or more, 10,000-fold or more, 100,000-fold or more, or 1,000,000-fold or more. Two nucleic acid strands that are hybridized to each other can form a duplex which comprises a double-stranded portion of nucleic acid.

As used herein, the terms "dark cycle" and "limited-extension cycle" and "LE cycle" refer to incorporating with a polymerase one or more nucleotides (e.g., native nucleotides) to the 3' end of a polynucleotide under a set of conditions that are different from a sequencing cycle. In embodiments, during a dark cycle the identity of a nucleotide is not determined following incorporation of the nucleotide. In embodiments, the identity of one or more (but not all) nucleotides is optionally determined upon incorporation. In embodiments, during a dark cycle, a native nucleotide (e.g., dATP, dCTP, dTTP, or dGTP) is incorporated into a polynucleotide. Due to it being a native nucleotide having no reversible terminator moiety, the polymerase does not temporarily halt, and the incorporated nucleotide is not detected or identified, and polymerization continues. In embodiments, during a dark cycle a nucleotide analogue comprising a label (e.g., dATP*, dCTP*, dTTP*, or dGTP*, wherein '*' indicates a labeled nucleotide) may be used and is incorporated into a polynucleotide. The identity of the incorporated nucleotide may be determined to ensure cluster synchronization. The native nucleotides may be any number of naturally occurring or modified nucleotides. In embodiments, the nucleotides include a reversible blocking group (i.e., a reversible terminator moiety). In embodiments, a dark cycle includes the incorporation of one or more nucleotides that are unidentified, and optionally one or more nucleotides that are identified.

As used herein, the term "extension" or "elongation" is used in accordance with their plain and ordinary meanings and refer to synthesis by a polymerase of a new polynucleotide strand complementary to a template strand by adding free nucleotides (e.g., dNTPs) from a reaction mixture that are complementary to the template in the 5'-to-3' direction. Extension includes condensing the 5'-phosphate group of the dNTPs with the 3'-hydroxy group at the end of the nascent (elongating) DNA strand.

As used herein, the term "sequencing read" is used in accordance with its plain and ordinary meaning and refers to an inferred sequence of base pairs (or base pair probabilities) corresponding to all or part of a single DNA fragment. Sequencing technologies vary in the length of reads produced. A sequencing read may include 10, 20, 30, 40, 50, 60, 70, 80, 90, 100, 150, 200, 250, or more nucleotide bases. Reads of length 20-40 base pairs (bp) are referred to as ultra-short. Typical sequencers produce read lengths in the range of 100-500 bp. Read length is a factor which can affect the results of biological studies. For example, longer read lengths improve the resolution of de novo genome assembly and detection of structural variants.

Provided herein are methods and compositions for analyzing a sample (e.g., sequencing nucleic acids within a sample). A sample (e.g., a sample comprising nucleic acid) can be obtained from a suitable subject. A sample can be isolated or obtained directly from a subject or part thereof. In some embodiments, a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. A fluid or tissue sample from which nucleic acid is extracted may be acellular (e.g., cell-free). Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may comprise cells or tissues that are normal, healthy, diseased (e.g., infected), and/or cancerous (e.g., cancer cells). A sample obtained from a subject may comprise cells or cellular material (e.g., nucleic acids) of multiple organisms (e.g., virus nucleic acid, fetal nucleic acid, bacterial nucleic acid, parasite nucleic acid).

In some embodiments, a sample comprises nucleic acid, or fragments thereof. A sample can comprise nucleic acids obtained from one or more subjects. In some embodiments a sample comprises nucleic acid obtained from a single subject. In some embodiments, a sample comprises a mixture of nucleic acids. A mixture of nucleic acids can comprise two or more nucleic acid species having different nucleotide sequences, different fragment lengths, different origins (e.g., genomic origins, cell or tissue origins, subject origins, the like or combinations thereof), or combinations thereof. A sample may comprise synthetic nucleic acid.

A subject can be any living or non-living organism, including but not limited to a human, non-human animal, plant, bacterium, fungus, virus or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a human subject. A subject can be a patient (e.g., a human patient). In some embodiments a subject is suspected of having a genetic variation or a disease or condition associated with a genetic variation.

As used herein, the term "consensus sequence" refers to a sequence that shows the nucleotide most commonly found at each position within the nucleic acid sequences of group of sequences (e.g., a group of sequencing reads) aligned at that position. A consensus sequence is often "assembled" from shorter sequence reads that are at least partially overlapping. Where two sequences contain overlapping sequence information aligned at one end and non-overlapping sequence information at opposite ends, the consensus sequence formed from the two sequences will be longer than either sequence individually. Aligning multiple such sequences allows for assembly of many short sequences into much longer consensus sequences representative of a longer sample polynucleotide. In embodiments, aligned sequences used to generate a consensus sequence may contain gaps (e.g., representative of nucleotides not appearing in a given read because they were extended during a dark cycle and not identified).

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

The term "kit" is used in accordance with its plain ordinary meaning and refers to any delivery system for delivering materials or reagents for carrying out a method of the invention. Such delivery systems include systems that allow for the storage, transport, or delivery of reaction reagents (e.g., nucleotides, enzymes, nucleic acid templates, etc. in the appropriate containers) and/or supporting materials (e.g., buffers, written instructions for performing the reaction, etc.) from one location to another location. For example, kits include one or more enclosures (e.g., boxes) containing the relevant reaction reagents and/or supporting materials. Such contents may be delivered to the intended recipient together or separately. For example, a first container may contain an enzyme, while a second container contains nucleotides. In embodiments, the kit includes vessels containing one or more enzymes, primers, adaptors, or other reagents as described herein. Vessels may include any structure capable of supporting or containing a liquid or solid material and may include, tubes, vials, jars, containers, tips, etc. In embodiments, a wall of a vessel may permit the transmission of light through the wall. In embodiments, the vessel may be optically clear. The kit may include the enzyme and/or nucleotides in a buffer. In embodiments, the buffer includes an acetate buffer, 3-(N-morpholino) propanesulfonic acid (MOPS) buffer, N-(2-Acetamido)-2-aminoethanesulfonic acid (ACES) buffer, phosphate-buffered saline (PBS) buffer, 4-(2-hydroxyethyl)-1-piperazineethanesulfonic acid (HEPES) buffer, N-(1,1-Dimethyl-2-hydroxyethyl)-3-amino-2-hydroxypropanesulfonic acid (AMPSO) buffer, borate buffer (e.g., borate buffered saline, sodium borate buffer, boric acid buffer), 2-Amino-2-methyl-1,3-propanediol (AMPD) buffer, N-cyclohexyl-2-hydroxyl-3-aminopropanesulfonic acid (CAPSO) buffer, 2-Amino-2-methyl-1-propanol (AMP) buffer, 4-(Cyclohexylamino)-1-butanesulfonic acid (CABS) buffer, glycine-NaOH buffer, N-Cyclohexyl-2-aminoethanesulfonic acid (CHES) buffer, tris(hydroxymethyl)aminomethane (Tris) buffer, or a N-cyclohexyl-3-aminopropanesulfonic acid (CAPS) buffer. In embodiments, the buffer is a borate buffer. In embodiments, the buffer is a CHES buffer.

The methods and kits of the present disclosure may be applied, mutatis mutandis, to the sequencing of RNA, or to determining the identity of a ribonucleotide.

By aqueous solution herein is meant a liquid comprising at least 20 vol % water. In embodiments, aqueous solution includes at least 50%, for example at least 75 vol %, at least 95 vol %, above 98 vol %, or 100 vol % of water as the continuous phase.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Sequencing Methods

In an aspect, provided herein are methods of sequencing a template nucleic acid, including step (a) executing one or more sequencing cycles that includes (i) extending a complementary polynucleotide that is hybridized to the template nucleic acid by incorporating a first nucleotide using a polymerase; and (ii) detecting a label that identifies the first nucleotide; step (b) extending the complementary polynucleotide in one or more dark cycles, where each dark cycle includes extending the complementary polynucleotide by one or more nucleotides using the polymerase, without performing a detection event (or without applying a detection process) to identify nucleotides incorporated during the dark cycle; and step (c) executing one or more sequencing cycles that includes (i) extending the complementary polynucleotide by incorporating a second nucleotide using a polymerase; and (ii) detecting a label that identifies the second nucleotide, thereby sequencing a template nucleic acid.

In another aspect, provided herein are methods of sequencing a template nucleic acid, including (a) executing one or more sequencing cycles that include (i) an extension step, where a complementary polynucleotide that is hybridized to the template nucleic acid is extended by incorporating a first nucleotide using a polymerase; and (ii) a detection step, where a characteristic signature is detected that identifies the first nucleotide; (b) extending the complementary polynucleotide in one or more dark cycles, where each dark cycle includes extending the complementary polynucleotide by one or more nucleotides using the polymerase, omitting a detection step to identify nucleotides incorporated during the dark cycle; and (c) executing one or more sequencing cycles that include (i) an extension step, where a complementary polynucleotide is extended by incorporating a second nucleotide using a polymerase; and (ii) a detection step, where a characteristic signature is detected that identifies the second nucleotide, thereby sequencing a template nucleic acid. In embodiments, the characteristic signature is indicative of the identity of the nucleotide, for example a specific fluorescent emission (e.g., Alexa Fluor™ 647 is indicative of dA). In embodiments, the characteristic signature is measured as a change in pH. For example, the pH change that occurs due to release of $H^+$ ions during the incorporation reaction is detected using a FET. In embodiments, the characteristic signature is a change in local charge density around the template nucleic acid. Methods for detecting electrical charges are known, including methods and systems such as field-effect transistors, dielectric spectroscopy, impedance measurements, and pH measurements, among others. Field-effect transistors include, but are not limited to, ion-sensitive field-effect transistors (ISFET), charge-modulated field-effect transistors, insulated-gate field-effect transistors, metal oxide semiconductor field-effect transistors and field-effect transistors fabricated using semiconducting single wall carbon nanotubes.

In embodiments, the characteristic signature is detecting the absence of a label. For example, when the method includes the detection of four different nucleotides using fewer than four different labels. As a first example, a pair of nucleotide types can be detected at the same wavelength, but distinguished based on a difference in signal states, such as the intensity, for one member of the pair compared to the other, or based on a change to one member of the pair (e.g., via chemical modification, photochemical modification or physical modification) that causes apparent signal to appear or disappear compared to the signal detected for the other member of the pair. As another example, three of four different nucleotide types can be detected under particular conditions while a fourth nucleotide type lacks a label that is detectable under those conditions, or is minimally detected under those conditions. Incorporation of the first three nucleotide types into a nucleic acid can be determined based on presence of their respective signals and incorporation of the fourth nucleotide type into the nucleic acid can be determined based on absence or minimal detection of any signal. As a third example, one nucleotide type can include label(s) that are detected in two different channels, whereas other nucleotide types are detected in no more than one of the channels. In embodiments, the characteristic signature is a fluorescent emission.

In embodiments, the method includes extending the complementary polynucleotide in one or more dark cycles, where each dark cycle includes extending the complementary polynucleotide by one or more nucleotides using the polymerase, without performing a detection event (or without performing a detection process) to identify nucleotides incorporated during a dark cycle before step (a). In embodiments, the nucleotides in each dark cycle do not include a label.

In an aspect, provided herein are methods of sequencing a template nucleic acid, including step (a) extending a complementary polynucleotide that is hybridized to the template nucleic acid in one or more dark cycles, where each dark cycle includes extending the complementary polynucleotide by one or more nucleotides using the polymerase, without performing a detection event to identify nucleotides incorporated during the dark cycle; step (b) executing a sequencing cycle that includes (i) extending the complementary polynucleotide by incorporating a first nucleotide using a polymerase; and (ii) detecting a label that identifies the first nucleotide; step (c) extending a complementary polynucleotide in one or more dark cycles, where each dark cycle includes extending the complementary polynucleotide by one or more nucleotides using the polymerase, without performing a detection event to identify nucleotides incorporated during the dark cycle; and step (d) executing a sequencing cycle that includes (i) extending the complementary polynucleotide by incorporating a second nucleotide using a polymerase; and (ii) detecting a label that identifies the second nucleotide, thereby sequencing a template nucleic acid.

In an aspect, provided herein are methods of sequencing a template nucleic acid, the method including step (a) executing one or more sequencing cycles, wherein each cycle includes (i) extending a complementary polynucleotide that is hybridized to the template nucleic acid by incorporating a first nucleotide using a polymerase; where said nucleotide includes a reversible terminator moiety, and (ii) detecting a label that identifies the first nucleotide; step (b) extending the complementary polynucleotide in one or more dark cycles, where each dark cycle includes extending the complementary polynucleotide by at least two nucleotides using the polymerase; where at least one nucleotide does not comprise a reversible terminator, and one nucleotide comprises a reversible terminator moiety, optionally performing a detection event to identify nucleotides incorporated during the dark cycle; and step (c) executing one or more sequencing cycles, wherein each cycle includes (i) extending the complementary polynucleotide by incorporating a second nucleotide using a polymerase; wherein the nucleotide comprises a reversible terminator moiety, and (ii) detecting a label that identifies the second nucleotide, thereby sequencing a template nucleic acid.

In embodiments, the methods of sequencing a template nucleic acid include extending the complementary polynucleotide in one or more dark cycles, where each dark cycle comprises extending the complementary polynucleotide by at least two nucleotides using the polymerase; where at least one nucleotide does not include a reversible terminator, and one nucleotide comprises a reversible terminator moiety, optionally performing a detection event to identify nucleotides incorporated during the dark cycle; and incorporated during a dark cycle before step (a) (e.g., as a quality check). In embodiments, each dark cycle comprises extending the complementary polynucleotide by a plurality of nucleotides.

In embodiments, a template nucleic acid can include any nucleic acid of interest. Template nucleic acids can include DNA, RNA, peptide nucleic acid, morpholino nucleic acid, locked nucleic acid, glycol nucleic acid, threose nucleic acid, mixtures thereof, and hybrids thereof. In embodiments, the template nucleic acid is obtained from one or more source organisms. As used herein the term "organism" is not necessarily limited to a particular species of organism but can be used to refer to the living or self-replicating particle at any level of classification, which comprises the template nucleic acid. For example, the term "organism" can be used to refer collectively to all of the species within the genus *Salmonella* or all of the bacteria within the kingdom Eubacteria. A template nucleic acid can comprise any nucleotide sequence. In some embodiments, the template nucleic acid can include a selected sequence or a portion of a larger sequence. In embodiments, sequencing a portion of a target nucleic acid or a fragment thereof can be used to identify the source of the target nucleic acid.

In embodiments, the template nucleic acid is at least 1000 bases (1 kb), at least 2 kb, at least 4 kb, at least 6 kb, at least 10 kb, at least 20 kb, at least 30 kb, at least 40 kb, or at least 50 kb in length. In embodiments, the entire sequence of the template nucleic acid is about 1 to 3 kb, and only a portion of that the sample polynucleotide (e.g., 50 to 100 nucleotides) is sequenced at a time. In embodiments, the template nucleic acid is about 2 to 3 kb. In embodiments, the template nucleic acid is about 1 to 10 kb. In embodiments, the template nucleic acid is about 3 to 10 kb. In embodiments, the template nucleic acid is about 5 to 10 kb. In embodiments, the template nucleic acid is about 1 to 3 kb. In embodiments, the template nucleic acid is about 1 to 2 kb. In embodiments, the template nucleic acid is greater than 1 kb. In embodiments, the template nucleic acid is greater than 500 bases. In embodiments, the template nucleic acid is about 1 kb. In embodiments, the template nucleic acid is about 2 kb. In embodiments, the template nucleic acid is less than 1 kb. In embodiments, the template nucleic acid is about 500 nucleotides. In embodiments, the template nucleic acid is about 510 nucleotides. In embodiments, the template nucleic acid is about 520 nucleotides. In embodiments, the template nucleic acid is about 530 nucleotides. In embodiments, the template nucleic acid is about 540 nucleotides. In embodiments, the template nucleic acid is about 550 nucleotides. In embodiments, the template nucleic acid is about 560 nucleotides. In embodiments, the template nucleic acid is about 570 nucleotides. In embodiments, the template nucleic acid is about 580 nucleotides. In embodiments, the template nucleic acid is about 590 nucleotides. In embodiments, the template nucleic acid is about 600 nucleotides. In embodiments, the template nucleic acid is about 610 nucleotides. In embodiments, the template nucleic acid is about 620 nucleotides. In embodiments, the template nucleic acid is about 630 nucleotides. In embodiments, the template nucleic acid is about 640 nucleotides. In embodiments, the template nucleic acid is about 650 nucleotides. In embodiments, the template nucleic acid is about 660 nucleotides. In embodiments, the template nucleic acid is about 670 nucleotides. In embodiments, the template nucleic acid is about 680 nucleotides. In embodiments, the template nucleic acid is about 690 nucleotides. In embodiments, the template nucleic acid is about 700 nucleotides. In embodiments, the template nucleic acid is about 1,600 nucleotides. In embodiments, the template nucleic acid is about 1,610 nucleotides. In embodiments, the template nucleic acid is about 1,620 nucleotides. In embodiments, the template nucleic acid is about 1,630 nucleotides. In embodiments, the template nucleic acid is about 1,640 nucleotides. In embodiments, the template nucleic acid is about 1,650 nucleotides. In embodiments, the template nucleic acid is about 1,660 nucleotides. In embodiments, the template nucleic acid is about 1,670 nucleotides. In embodiments, the template nucleic acid is about 1,680 nucleotides. In embodiments, the template nucleic acid is about 1,690 nucleotides. In embodiments, the template nucleic acid is about 1,700 nucleotides. In embodiments, the template nucleic acid is about 1,710 nucleotides. In embodiments, the template nucleic acid is about 1,720 nucleotides. In embodiments, the template nucleic acid is about 1,730 nucleotides. In embodiments, the template nucleic acid is about 1,740 nucleotides. In embodiments, the template nucleic acid is about 1,750 nucleotides. In embodiments, the template nucleic acid is about 1,760 nucleotides. In embodiments, the template nucleic acid is about 1,770 nucleotides. In embodiments, the template nucleic acid is about 1,780 nucleotides. In embodiments, the template nucleic acid is about 1,790 nucleotides. In embodiments, the template nucleic acid is about 1,800 nucleotides.

In embodiments the template nucleic acid is an RNA transcript. RNA transcripts are responsible for the process of converting DNA into an organism's phenotype, thus by determining the types and quantity of RNA present in a sample (e.g., a cell), it is possible to assign a phenotype to the cell. RNA transcripts include coding RNA and non-coding RNA molecules, such as messenger RNA (mRNA), transfer RNA (tRNA), micro RNA (miRNA), small interfering RNA (siRNA), small nucleolar RNA (snoRNA), small nuclear RNA (snRNA), Piwi-interacting RNA (piRNA), enhancer RNA (eRNA), or ribosomal RNA (rRNA). In embodiments, the template nucleic acid is pre-mRNA. In embodiments, the template nucleic acid is heterogeneous nuclear RNA (hnRNA). In embodiments the template nucleic acid is a single stranded RNA nucleic acid sequence. In embodiments, the template nucleic acid is an RNA nucleic acid sequence or a DNA nucleic acid sequence (e.g., cDNA). In embodiments, the template nucleic acid is a cDNA target nucleic acid sequence. In embodiments, the template nucleic acid is genomic DNA (gDNA), mitochondrial DNA, chloroplast DNA, episomal DNA, viral DNA, or complementary DNA (cDNA). In embodiments, the template nucleic acid is coding RNA such as messenger RNA (mRNA), and non-coding RNA (ncRNA) such as transfer RNA (tRNA), microRNA (miRNA), small nuclear RNA (snRNA), or ribosomal RNA (rRNA).

In embodiments, the template nucleic acid includes a cancer-associated gene or fragment thereof. In embodiments, the cancer-associated gene is a MDC, NME-2, KGF, P1GF, Flt-3L, HGF, MCP1, SAT-1, MIP-1-b, GCLM, OPG, TNF RII, VEGF-D, ITAC, MMP-10, GPI, PPP2R4, AKR1B1, Amy1A, MIP-1b, P-Cadherin, or EPO gene or fragment thereof. In embodiments, the cancer-associated gene is a AKT1, AKT2, AKT3, ALK, AR, ARAF, ARID1A, ATM, ATR, ATRX, AXL, BAP1, BRAF, BRCA1, BRCA2, BTK, CBL, CCND1, CCND2, CCND3, CCNE1, CDK12, CDK2, CDK4, CDK6, CDKN1B, CDKN2A, CDKN2B, CHEK1, CHEK2, CREBBP, CSF1R, CTNNB1, DDR2, EGFR, ERBB2, ERBB3, ERBB4, ERCC2, ERG, ESR1, ETV1, ETV4, ETV5, EZH2, FANCA, FANCD2, FANCI, FBXW7, FGF19, FGF3, FGFR1, FGFR2, FGFR3, FGFR4, FGR, FLT3, FOXL2, GATA2, GNA11, GNAQ, GNAS, H3F3A, HIST1H3B, HNF1A, HRAS, IDH1, IDH2, IGF1R, JAK1, JAK2, JAK3, KDR, KIT, KNSTRN, KRAS, MAGOH, MAP2K1, MAP2K2, MAP2K4, MAPK1, MAX, MDM2, MDM4, MED12, MET, MLH1, MRE11A, MSH2, MSH6, MTOR, MYB, MYBL1, MYC, MYCL, MYCN, MYD88, NBN, NF1, NF2, NFE2L2, NOTCH1, NOTCH2, NOTCH3, NOTCH4, NRAS, NRG1, NTRK1, NTRK2, NTRK3, NUTM1, PALB2, PDGFRA, PDGFRB, PIK3CA, PIK3CB, PIK3R1, PMS2, POLE, PPARG, PPP2R1A, PRKACA, PRKACB, PTCH1, PTEN, PTPN11, RAC1, RAD50, RAD51, RAD51B, RAD51C, RAD51D, RAF1, RB1, RELA, RET, RHEB, RHOA, RICTOR, RNF43, ROS1, RSPO2, RSPO3, SETD2, SF3B1, SLX4, SMAD4, SMARCA4, SMARCB1, SMO, SPOP, SRC, STAT3, STK11, TERT, TOP1, TP53, TSC1, TSC2, U2AF1, or XPO1 gene, or fragment thereof. In embodiments, the cancer-associated gene is a ABL1, AKT1, ALK, APC, ATM, BRAF, CDH1, CDKN2A, CSF1R, CTNNB1, EGFR, ERBB2, ERBB4, EZH2, FBXW7, FGFR1, FGFR2, FGFR3, FLT3, GNA11, GNAQ, GNAS, HNF1A, HRAS, IDH1, IDH2, JAK2, JAK3, KDR, KIT, KRAS, MET, MLH1, MPL, NOTCH1, NPM1, NRAS, PDGFRA, PIK3CA, PTEN, PTPN11, RB1, RET, SMAD4, SMARCB1, SMO, SRC, STK11, TP53, or VHL gene, or fragment thereof.

In embodiments, the template nucleic acids are RNA nucleic acid sequences or DNA nucleic acid sequences. In embodiments, the template nucleic acids are RNA nucleic acid sequences or DNA nucleic acid sequences from the same cell. In embodiments, the template nucleic acids are RNA nucleic acid sequences. In embodiments, the RNA nucleic acid sequence is stabilized using known techniques in the art. For example, RNA degradation by RNase should be minimized using commercially available solutions (e.g., RNA Later®, RNA Protect®, or DNA/RNA Shield®). In embodiments, the sample polynucleotides are messenger RNA (mRNA), transfer RNA (tRNA), micro RNA (miRNA), small interfering RNA (siRNA), small nucleolar RNA (snoRNA), small nuclear RNA (snRNA), Piwi-interacting RNA (piRNA), enhancer RNA (eRNA), or ribosomal RNA (rRNA). In embodiments, the template nucleic acid is pre-mRNA. In embodiments, the template nucleic acid is heterogeneous nuclear RNA (hnRNA). In embodiments, the template nucleic acid is mRNA, tRNA (transfer RNA), rRNA (ribosomal RNA), or noncoding RNA (such as lncRNA (long noncoding RNA)). In embodiments, the template nucleic acids are on different regions of the same RNA nucleic acid sequence. In embodiments, the template nucleic acid is cDNA target nucleic acid sequences and before step i), the RNA nucleic acid sequences are reverse transcribed to generate the cDNA target nucleic acid sequences. In embodiments, the template nucleic acid is not reverse transcribed to cDNA. When mRNA is reverse transcribed an oligo(dT) primer can be added to better hybridize to the poly A tail of the mRNA. The oligo(dT) primer may include between about 12 and about 25 dT residues. The oligo(dT) primer may be an oligo(dT) primer of between about 18 to about 25 nt in length.

In embodiments, the template nucleic acid includes a gene or a gene fragment. In embodiments, the gene or gene fragment is a cancer-associated gene or fragment thereof, T cell receptor (TCRs) gene or fragment thereof, or a B cell receptor (BCRs) gene, or fragment thereof. In embodiments, the gene or gene fragment is a CDR3 gene or fragment thereof. In embodiments, the gene or gene fragment is a T cell receptor alpha variable (TRAV) gene or fragment thereof, T cell receptor alpha joining (TRAJ) gene or fragment thereof, T cell receptor alpha constant (TRAC) gene or fragment thereof, T cell receptor beta variable (TRBV) gene or fragment thereof, T cell receptor beta diversity (TRBD) gene or fragment thereof, T cell receptor beta joining (TRBJ) gene or fragment thereof, T cell receptor beta constant (TRBC) gene or fragment thereof, T cell receptor gamma variable (TRGV) gene or fragment thereof, T cell receptor gamma joining (TRGJ) gene or fragment thereof, T cell receptor gamma constant (TRGC) gene or fragment thereof, T cell receptor delta variable (TRDV) gene or fragment thereof, T cell receptor delta diversity (TRDD) gene or fragment thereof, T cell receptor delta joining (TRDJ) gene or fragment thereof, or T cell receptor delta constant (TRDC) gene or fragment thereof. In embodiments, the polynucleotide includes genomic DNA, complementary DNA (cDNA), cell-free DNA (cfDNA), messenger RNA (mRNA), transfer RNA (tRNA), ribosomal RNA (rRNA), cell-free RNA (cfRNA), or noncoding RNA (ncRNA). In embodiments, the polynucleotide includes messenger RNA (mRNA), transfer RNA (tRNA), micro RNA (miRNA), small interfering RNA (siRNA), small nucleolar RNA (snoRNA), small nuclear RNA (snRNA), Piwi-interacting RNA (piRNA), enhancer RNA (eRNA), or ribosomal RNA (rRNA).

In embodiments, the template nucleic acid includes a gene fusion. Gene fusions are a type of somatic alteration leading to cancer associated with up to 20% of cancer morbidity and having oncogenic roles in hematological, soft tissue, and solid tumors (Foltz S M et al. Nature Comm. 2020; 11:2666). Translocations, copy number changes, and inversions can lead to fusions, dysregulared gene expression, and novel molecular functions. In embodiments, the gene fusion includes a CD74-ROS1, SLC34A2-ROS1, SDC4-ROS1, EZR-ROS1, GOPC-ROS1, LRIG3-ROS1, TPM3-ROS1, PPFIBP1-ROS1, EML4-ALK, BCR-ABL, TCF3-PBX1, ETV6-RUNX1, MLL-AF4, SIL-TAL1, RET-NTRK1, PAX8-PPARG, MECT1-MAML2, TFE3-TFEB, BRD4-NUT, ETV6-NTRK3, TMPRSS2-ERG, TPM3-NTRK1, SQSTM1-NTRK1, CD74-NTRK1, MPRIP-NTRK1, or TRIM24-NTRK2, wherein the gene fusion is written in the format [gene1]-[gene2]. In embodiments, the gene fusion includes a ROS1 gene or fragment thereof, ALK gene or fragment thereof, EML4 gene or fragment thereof, BCR gene or fragment thereof, ABL gene or fragment thereof, TCF3 gene or fragment thereof, PBX1 gene or fragment thereof, ETV6 gene or fragment thereof, RUNX1 gene or fragment thereof, MLL gene or fragment thereof, AF4 gene or fragment thereof, SIL gene or fragment thereof, TAL1 gene or fragment thereof, RET gene or fragment thereof, NTRK1 gene or fragment thereof, PAX8 gene or fragment thereof, PPARG gene or fragment thereof, MECT1 gene or fragment thereof, MAML2 gene or fragment thereof, TFE3 gene or fragment thereof, TFEB gene or fragment thereof, BRD4 gene or fragment thereof, NUT gene or fragment thereof, ETV6 gene or fragment thereof, NTRK3 gene or fragment thereof, TMPRSS2 gene or fragment thereof, NKRT2 gene or fragment thereof, an ERG gene or fragment thereof, and at least one other gene.

In embodiments, the methods and compositions described herein are utilized to analyze the various sequences of T cell receptors (TCRs) and B cell receptors (BCRs) from immune cells, for example various clonotypes. In embodiments, the target nucleic acid includes a nucleic acid sequence encoding a TCR alpha (TCRA) chain, a TCR beta (TCRB) chain, a TCR delta (TCRD) chain, a TCR gamma (TCRG) chain, or any fragment thereof (e.g., variable regions including VDJ or VJ regions, constant regions, transmembrane regions, fragments thereof, combinations thereof, and combinations of fragments thereof). In embodiments, the template nucleic acid includes a nucleic acid sequence encoding a B cell receptor heavy chain, B cell receptor light chain, or any fragment thereof (e.g., variable regions including VDJ or VJ regions, constant regions, transmembrane regions, fragments thereof, combinations thereof, and combinations of fragments thereof). In embodiments, the template nucleic acid includes a CDR3 nucleic acid sequence. In embodiments, the template nucleic acid includes a TCRA gene sequence or a TCRB gene sequence. In embodiments, the template nucleic acid includes a TCRA gene sequence and a TCRB gene sequence. In embodiments, the template nucleic acid includes sequences of various T cell receptor alpha variable genes (TRAV genes), T cell receptor alpha joining genes (TRAJ genes), T cell receptor alpha constant genes (TRAC genes), T cell receptor beta variable genes (TRBV genes), T cell receptor beta diversity genes (TRBD genes), T cell receptor beta joining genes (TRBJ genes), T cell receptor beta constant genes (TRBC genes), T cell receptor gamma variable genes (TRGV genes), T cell receptor gamma joining genes (TRGJ genes), T cell receptor gamma constant genes (TRGC genes), T cell receptor delta variable genes (TRDV genes), T cell receptor delta diversity genes (TRDD genes), T cell receptor delta joining genes (TRDJ genes), or T cell receptor delta constant genes (TRDC genes).

In embodiments, the methods described herein can utilize a single template nucleic acid. Other embodiments can utilize a plurality of template nucleic acids. In such embodiments, a plurality of template nucleic acids can include a plurality of the same template nucleic acids, a plurality of different template nucleic acids where some template nucleic acids are the same, or a plurality of template nucleic acids where all template nucleic acids are different. In some embodiments, the plurality of template nucleic acids can include substantially all of a particular organism's genome. In some embodiments, the plurality of template nucleic acids can include at least a portion of a particular organism's genome including, for example, at least about 10%, 25%, 50%, 75%, 80%, 85%, 90%, 95%, or 99% of the genome. In other embodiments, the plurality of template nucleic acids can include a single nucleotide sequence of the genome of an organism or a single expressed nucleotide sequence. In still other embodiments, the plurality of template nucleic acids can include a portion of a single nucleotide sequence of the genome of an organism or a portion of a single expressed nucleotide sequence. With reference to nucleic acids, polynucleotides and/or nucleotide sequences a "portion," "fragment" or "region" can be at least 5 consecutive nucleotides, at least 10 consecutive nucleotides, at least 15 consecutive nucleotides, at least 20 consecutive nucleotides, at least 25 consecutive nucleotides, at least 50 consecutive nucleotides or at least 100 consecutive nucleotides.

In embodiments, to initiate a sequencing cycle, one or more differently labeled nucleotides and a DNA polymerase can be introduced to a template nucleic acid. Either a single nucleotide can be added at a time, or the nucleotides used in the sequencing procedure can include a reversible terminator moiety, thus allowing each cycle of the sequencing reaction to occur simultaneously in the presence of all four labeled nucleotides (dA, dC, dT, dG). Following nucleotide addition, signals produced (e.g., signals produced at the features on a surface) can be detected to determine the identity of the incorporated nucleotide (based on the labels on the nucleotides). Reagents can then be added to remove the 3' reversible terminator and to remove labels from each incorporated base. Reagents, enzymes and other substances can be removed between steps by washing. Such cycles are then repeated and the sequence of each cluster is read over the multiple chemistry cycles. The identity of the base present in one or more of the added nucleotide(s) can be determined in a detection or imaging step, preferably after each nucleotide incorporation. In embodiments, fluorescently labeled nucleotides are used in the sequencing cycle. The four different bases are each labeled with a unique fluorescent label to permit identification of the incorporated nucleotide as successive nucleotides are added. The labeled nucleotides also can have a removable 3' reversible terminator to prevent further incorporation by temporarily halting the polymerase. The label of the incorporated base can be determined and the reversible terminator removed to permit further extension. The labels may be the same for each type of nucleotide, or each nucleotide type may carry a different label. This facilitates the identification of incorporation of a particular nucleotide. Thus, for example modified adenine, guanine, cytosine and thymine would all have attached a different fluorophore to allow them to be discriminated from one another readily.

In embodiments, the methods of sequencing a template nucleic acid include a extending a polynucleotide by using a polymerase. In embodiments, the polymerase is a DNA polymerase. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol µ DNA polymerase, Pol λ DNA polymerase, Pol σ DNA polymerase, Pol α DNA polymerase, Pol δ DNA polymerase, Pol ε DNA polymerase, Pol η DNA polymerase, Pol τ DNA polymerase, Pol κ DNA polymerase, Pol ζ DNA polymerase, Pol γ DNA polymerase, Pol θ DNA polymerase, Pol ν DNA polymerase, or a thermophilic nucleic acid polymerase (e.g. Terminator γ, 9° N polymerase (exo-), Terminator II, Terminator III, or Terminator IX). In embodiments, the DNA polymerase is a thermophilic nucleic acid polymerase. In embodiments, the DNA polymerase is a modified archaeal DNA polymerase. In embodiments, the polymerase is a bacterial DNA polymerase, eukaryotic DNA polymerase, archaeal DNA polymerase, viral DNA polymerase, or phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases α, β, γ, δ, ε, η, ζ, σ, µ, and k, as well as the Revl polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cp1 DNA polymerase, Cp1 DNA polymerase, T7 DNA polymerase, and T4 polymerase. Other useful DNA polymerases include thermostable and/or thermophilic DNA polymerases such as *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. In embodiments, the polymerase is 3PDX polymerase as disclosed in U.S. Pat. No. 8,703,461, the disclosure of which is incorporated herein by reference. In embodiments, the polymerase is a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, or Telomerase reverse transcriptase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044, both of which are incorporated by reference herein). In embodiments, the polymerase is DNA polymerase, a terminal deoxynucleotidyl transferase, or a reverse transcriptase. In embodiments, the enzyme is a DNA polymerase, such as DNA polymerase 812 (Pol 812) or DNA polymerase 1901 (Pol 1901), e.g., a polymerase described in US 2020/0131484, and US 2020/0181587, both of which are incorporated by reference herein.

In embodiments, the methods of sequencing a template nucleic acid include extending a complementary polynucleotide that is hybridized to the template nucleic acid by incorporating a first nucleotide. In embodiments, the nucleotide is selected from one or more of dATP, dCTP, dGTP, and dTTP or an analogue thereof. In embodiments, the nucleotide includes a detectable label. In embodiments, the detectable label is a fluorescent label. In embodiments, the nucleotide includes a reversible terminator moiety. In embodiments, the reversible terminator moiety may be 3'-O-blocked reversible terminator. In nucleotides with 3'-O-blocked reversible terminators, the blocking group (referred to as —OR) wherein the 0 of —OR is the oxygen atom of the 3'-OH of the pentose, and R of —OR is the blocking group (i.e. the reversible terminator moiety) while the label is linked to the base, which acts as a reporter and can be cleaved. The 3'-O-blocked reversible terminators are known in the art, and may be, for instance, a 3'-ONH$_2$ reversible terminator, a 3'-O-allyl reversible terminator, or a 3'-O-azidomethyl reversible terminator. In embodiments, the reversible terminator moiety is

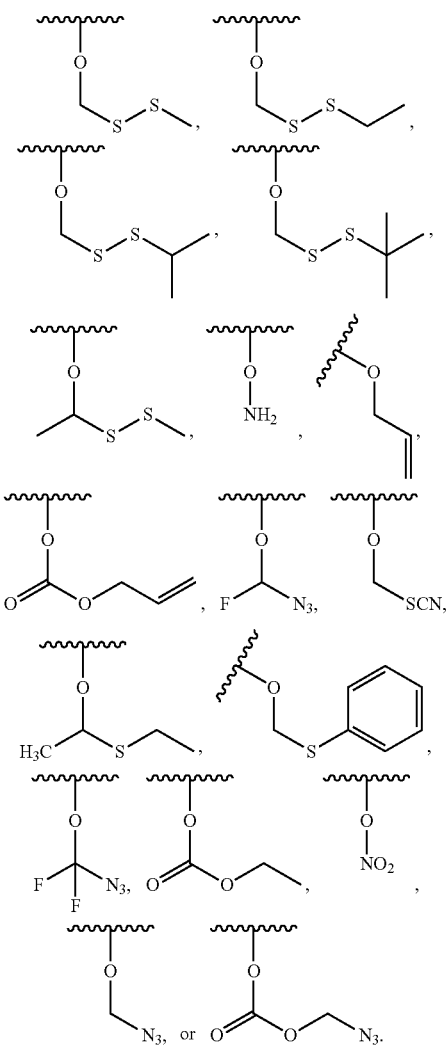

In embodiments, the method comprises a plurality of cycles, with each cycle comprising incorporation and identification of a first nucleotide. In some embodiments of methods comprising a plurality of sequencing cycles, the first nucleotide incorporated in one cycle of the plurality of cycles may be the same or different from the first nucleotide incorporated in another cycle of the plurality of cycles.

In embodiments, the nucleotide has the formula:

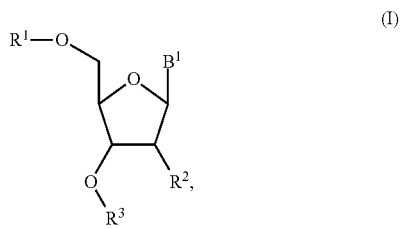

wherein $B^1$ is a nucleobase; $R^1$ is —OH, a monophosphate moiety, or polyphosphate moiety; $R^2$ is —OH or hydrogen; and $R^3$ is a reversible terminator moiety.

In embodiments, $B^1$ is

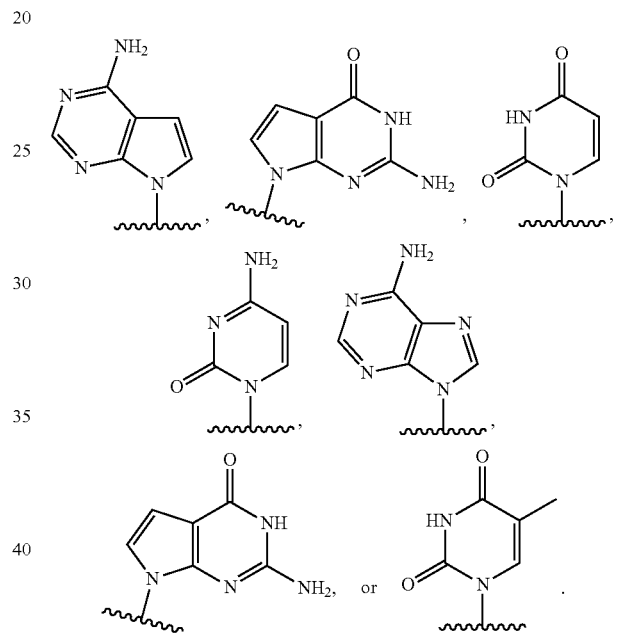

In embodiments, $B^1$ is a divalent nucleobase. In embodiments, $B^1$ is

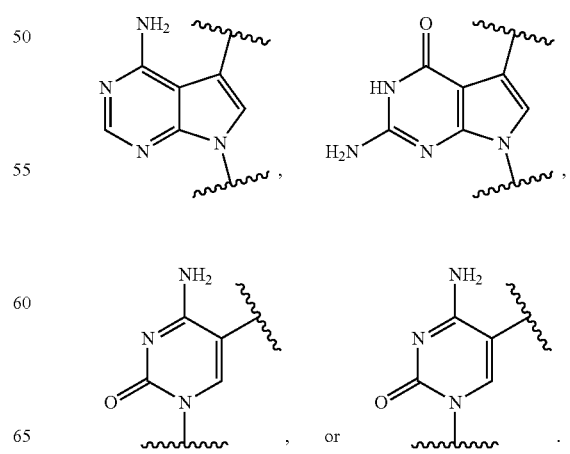

In embodiments, B¹ is

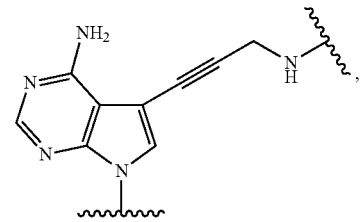

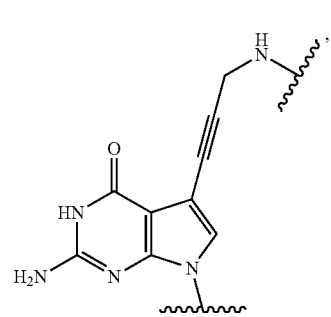

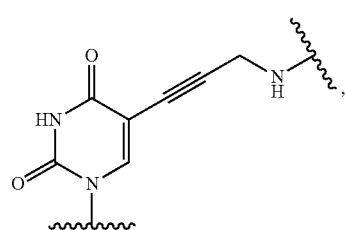

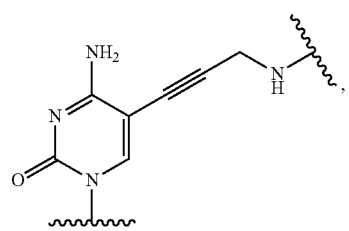

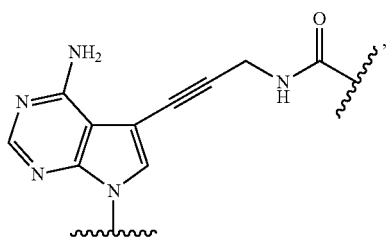

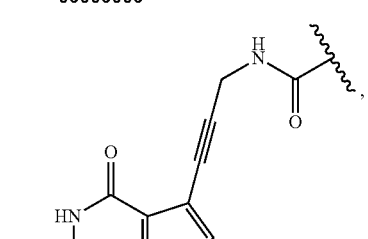

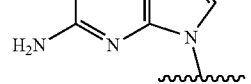

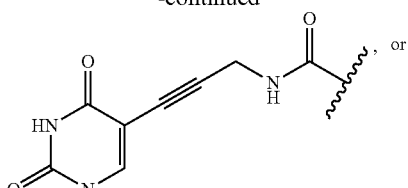

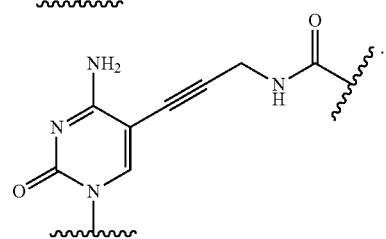

In embodiments, B¹ is —B-L¹⁰⁰-R⁴. B is a divalent cytosine or a derivative thereof, divalent guanine or a derivative thereof, divalent adenine or a derivative thereof, divalent thymine or a derivative thereof, divalent uracil or a derivative thereof, divalent hypoxanthine or a derivative thereof, divalent xanthine or a derivative thereof, divalent 7-methylguanine or a derivative thereof, divalent 5,6-dihydrouracil or a derivative thereof, divalent 5-methylcytosine or a derivative thereof, or divalent 5-hydroxymethylcytosine or a derivative thereof. L¹⁰⁰ is a divalent linker; and R⁴ is a detectable moiety. In embodiments, L¹⁰⁰ is independently a bioconjugate linker, a cleavable linker, or a self-immolative linker.

In embodiments, R⁴ is a detectable moiety. In embodiments, R⁴ is a fluorescent dye moiety. In embodiments, R⁴ is a detectable moiety described herein (e.g., Dye Table). In embodiments, R⁴ is a detectable moiety described in the Dye Table.

DYE TABLE

Detectable moieties to be used in selected embodiments.

| Nucleoside/nucleotide abbreviation | Dye name | λmax (nm) |
|---|---|---|
| dC | Atto 532 | 532 |
| dC | Atto Rho 6G | 535 |
| dC | R6G | 534 |
| dC | Tet | 521 |
| dT | Atto Rho 11 | 572 |
| dT | Atto 565 | 564 |
| dT | Alexa Fluor 568 | 578 |
| dT | dTamra | 578 |
| dA | Alexa Fluor 647 | 650 |
| dA | Atto 647N | 644 |
| dA | Janelia Fluor 646 | 646 |
| dG | Alexa Fluor 680 | 682 |
| dG | Alexa Fluor 700 | 696 |
| dG | CF680R | 680 |

In embodiments, the methods of sequencing a template nucleic acid include extending a complementary polynucleotide in one or more dark cycles. In embodiments, a dark cycle includes extending the complementary polynucleotide by one or more nucleotides using the polymerase, without performing a detection event to identify nucleotides incorporated during the dark cycle. In embodiments, the one or more nucleotides include native nucleotides or analogues thereof. Native nucleotides or analogues thereof, as described herein, do not necessarily include a label, and are not detected in a dark cycle. In embodiments, the one or more nucleotides include a combination of native nucleotides and nucleotides with a reversible terminator moiety. In embodiments, the methods of sequencing a template nucleic acid include extending a complementary polynucleotide in a plurality of dark cycles.

In embodiments, the one or more nucleotides used in the dark cycle have the formula:

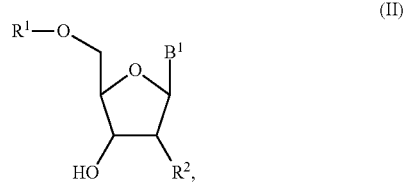

(II)

wherein $R^1$, $R^2$, and $B^1$ are as described herein, including embodiments. In embodiments, four or fewer different nucleotides are present during the dark cycles and each is labeled differently.

In embodiments, a dark cycle includes extending the complementary polynucleotide by at least two nucleotides using the polymerase. In embodiments, the at least two nucleotides include native nucleotides or analogues thereof. In embodiments, at least one of the at least two nucleotides include a reversible terminator moiety. In embodiments, the methods of sequencing a template nucleic acid include extending a complementary polynucleotide in one or more dark cycles further including optionally performing a detection event to identify one or more (but not all) nucleotides incorporated during the dark cycle. This may serve as a quality control measure, for example, to check synchronization of the cluster. In embodiments, a dark cycle includes extending the complementary polynucleotide by plurality of nucleotides using the polymerase. In embodiments, a dark cycle includes extending the complementary polynucleotide by incorporating into the complementary polynucleotide at least two nucleotides using the polymerase. In embodiments, a dark cycle includes extending the complementary polynucleotide by two or more nucleotides using the polymerase.

In embodiments, the methods of sequencing a template nucleic acid includes executing a sequencing cycle after a dark cycle, the sequencing cycle including (i) extending the complementary polynucleotide by incorporating a second nucleotide using a polymerase; and (ii) detecting a label that identifies the second nucleotide. In embodiments, the methods of sequencing a template nucleic acid includes executing a sequencing cycle after a dark cycle, the sequencing cycle including (i) extending the complementary polynucleotide by incorporating a second nucleotide using a polymerase; and (ii) detecting a characteristic signal that identifies the second nucleotide. In embodiments, the methods of sequencing a template nucleic acid includes executing a plurality of sequencing cycles after a dark cycle, each sequencing cycle including (i) extending the complementary polynucleotide by incorporating a second nucleotide using a polymerase; and (ii) detecting a label that identifies the second nucleotide. In embodiments, the nucleotide is selected from one or more of dATP, dCTP, dGTP, and dTTP or analogue thereof. In embodiments, the nucleotide includes a detectable label. In embodiments, the detectable label is a fluorescent label. In other embodiments, the nucleotide includes a reversible terminator moiety. In embodiments, the reversible terminator moiety may be 3'-O-blocked reversible or 3'-unblocked reversible terminator. In nucleotides with 3'-O-blocked reversible terminators, the blocking group (—OR) is linked to the oxygen atom of the 3'-OH of the pentose, while the label is linked to the base, which acts as a reporter and can be cleaved. The 3'-O-blocked reversible terminators are known in the art, and may be, for instance, a 3'-$ONH_2$ reversible terminator, a 3'-O-allyl reversible terminator, or a 3'-O-azidomethyl reversible terminator. In embodiments, the second nucleotide is selected independently of (and may be the same as or different from) the first nucleotide. In some embodiments of methods comprising a plurality of sequencing cycles after a dark cycle, the second nucleotide incorporated in one cycle of the plurality of cycles may be the same or different from the second nucleotide incorporated in another cycle of the plurality of cycles.

In embodiments, the methods of sequencing a template nucleic acid further include executing a second round of one or more dark cycles after an intervening sequencing cycle. In embodiments, the second dark cycle follows the same parameters as the preceding dark cycle, such as a dark cycle with respect to any of the aspects disclosed herein. In embodiments, alternating steps of sequencing cycles followed by dark cycles (or dark cycles followed by sequencing cycles, depending on which is performed first) form a complementary polynucleotide comprising a series of units, each unit comprising nucleotides added by a sequencing cycle and an immediately following (or preceding) dark cycle. In embodiments, a sequencing read represents a complementary polynucleotide comprising about or at least about 1, 2, 3, 4, 5, 6, 7, 8, 9, 10, 15, 20, 25, 30, 40, 50, or more units. In embodiments, the complementary polynucleotide comprises about 1 to about 50 units. In embodiments, the complementary polynucleotide comprises about 10 to about 40 units. In embodiments, the complementary polynucleotide comprises about 20 to about 30 units. In embodiments, the complementary polynucleotide comprises about or at least about 2 units. In embodiments, the complementary polynucleotide comprises about or at least about 4 units. In embodiments, the complementary polynucleotide comprises about or at least about 6 units. In embodiments, the complementary polynucleotide comprises about or at least about 8 units.

In embodiments, the method includes a plurality of sequencing cycles, a plurality of dark cycles, and a plurality of sequencing cycles. In embodiments, the method includes a plurality of sequencing cycles, a plurality of dark cycles, a plurality of sequencing cycles, a plurality of dark cycles, and a plurality of sequencing cycles. In embodiments, the method includes a plurality of dark cycles, a plurality of sequencing cycles, and a plurality of dark cycles. In embodiments, the method includes a plurality of dark cycles, a plurality of sequencing cycles, a plurality of dark cycles, and a plurality of sequencing cycles.

In embodiments, the methods of sequencing a template nucleic acid include a step of executing a sequencing cycle further includes (iii) repeating steps (i) and (ii) one or more times, thereby incorporating one or more additional nucleotides that are identified in the process, according to any of the aspects disclosed herein. In embodiments, extension permits a single type of nucleotide whose identity is known to be incorporated as many times as is indicated by the complementary strand. For example, adding "A" nucleotides to a template where the next position is a "T" followed by a "G" will incorporate a single "A" nucleotide. However, in a template where the next two positions are both "T," then two "A" nucleotides may be incorporated. Nucleotides of known types can be cycled, thereby growing the complementary strand. In embodiments, individual nucleotides are added one at a time from a mixture of different types of nucleotides during a sequencing cycle, where the identity of each subsequent nucleotide is determined following its incorporation, and may be the same as or different from the nucleotide that preceded it (depending on the sequence of the template strand). In embodiments, a sequencing cycle incorporates and identifies about or at least about 2, 3, 4, 5, 6, 7, 8, 9, 10, 15, 20, 25, or more nucleotides. In embodiments, a sequencing cycle incorporates and identifies about or at least about 1 to 100 nucleotides. In embodiments, a sequencing cycle incorporates and identifies about or at least about 10 to 50 nucleotides. In embodiments, a sequencing cycle incorporates and identifies about or at least about 20 to 40 nucleotides. In embodiments, a sequencing cycle incorporates and identifies about or at least about 5 nucleotides. In embodiments, a sequencing cycle incorporates and identifies about or at least about 10 nucleotides. In embodiments, a sequencing cycle incorporates and identifies about or at least about 15 nucleotides. In embodiments, a sequencing cycle incorporates and identifies about or at least about 20 nucleotides.

In embodiments, the methods of sequencing a template nucleic acid include executing a second sequencing cycle of a sequencing cycle that further includes (iii) repeating steps (i) and (ii) one or more times, thereby incorporating one or more additional nucleotides that are identified in the process, according to any of the aspects disclosed herein. The second sequencing cycle may follow or precede a dark cycle, according to any of the aspects disclosed herein. In embodiments, extension permits a single type of nucleotide whose identity is known to be incorporated as many times as is indicated by the complementary strand. For example, adding "A" nucleotides to a template where the next position is a "T" followed by a "G" will incorporate a single "A" nucleotide. However, in a template where the next two positions are both "T," then two "A" nucleotides may be incorporated. Nucleotides of known types can be cycled, thereby growing the complementary strand. In embodiments, individual nucleotides are added one at a time from a mixture of different types of nucleotides during a sequencing cycle, where the identity of each subsequent nucleotide is determined following its incorporation, and may be the same as or different from the nucleotide that preceded it (depending on the sequence of the template strand). In embodiments, a sequencing cycle incorporates and identifies about or at least about 2, 3, 4, 5, 6, 7, 8, 9, 10, 15, 20, 25, or more nucleotides. In embodiments, a sequencing cycle incorporates and identifies about or at least about 1 to 100 nucleotides. In embodiments, a sequencing cycle incorporates and identifies about or at least about 10 to 50 nucleotides. In embodiments, a sequencing cycle incorporates and identifies about or at least about 20 to 40 nucleotides. In embodiments, a sequencing cycle incorporates and identifies about or at least about 5 nucleotides. In embodiments, a sequencing cycle incorporates and identifies about or at least about 10 nucleotides. In embodiments, a sequencing cycle incorporates and identifies about or at least about 15 nucleotides. In embodiments, a sequencing cycle incorporates and identifies about or at least about 20 nucleotides. In embodiments, the methods of sequencing a template nucleic acid further includes repeating one or more sequencing cycles and one or more dark cycles, collectively one or more times. In embodiments, the method comprises a first sequencing cycle, followed by one or more dark cycles, followed by a further sequencing cycle, followed by a further one or more dark cycles, and the entire process may be repeated one or more times. In embodiments, the methods of sequencing a template nucleic acid include executing one or more sequencing cycles before and after an intervening dark cycle. In embodiments, the second sequencing cycle follows the same parameters as the preceding sequencing cycle, such as a sequencing cycle with respect to any of the aspects disclosed herein. In embodiments, the methods of sequencing a template nucleic acid include executing a second round of one or more dark cycles after an intervening sequencing cycle. In embodiments, the second dark cycle follows the same parameters as the preceding dark cycle, such as a dark cycle with respect to any of the aspects disclosed herein. In embodiments, alternating steps of sequencing cycles followed by dark cycles (or dark cycles followed by sequencing cycles, depending on which is performed first) form a complementary polynucleotide comprising a series of units, each unit comprising nucleotides added by a sequencing cycle and an immediately following (or preceding) dark cycle. In embodiments, the method comprises a first sequencing cycle, followed by one or more dark cycles, followed by a further sequencing cycle, followed by a further one or more dark cycles, and the entire process may be repeated one or more times, and each repeat defining a unit. In embodiments, the entire process may include a total number of sequencing and dark cycles of about 1 to about 100, or about 20 to about 50. In embodiments, the total number of sequencing and dark cycles is about 1, 2, 5, 10, 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 cycles. In embodiments, the total number of sequencing and dark cycles is about 2 cycles. In embodiments, the total number of sequencing and dark cycles is about 10 cycles. In embodiments, the total number of sequencing and dark cycles is about 20 cycles. In embodiments, the total number of sequencing cycles is about 30 cycles. In embodiments, the total number of sequencing and dark cycles is about 40 cycles. In embodiments, the total number of sequencing and dark cycles is about 50 cycles. In embodiments, the total number of sequencing and dark cycles is greater than 50 cycles. In embodiments, the total number of sequencing and dark cycles is greater than 100 cycles. In embodiments, the total number of sequencing and dark cycles is greater than 150 cycles. In embodiments, the total number of sequencing and dark cycles is greater than 200 cycles. In embodiments, the total number of sequencing and dark cycles is greater than 250 cycles. In embodiments, the total number of sequencing and dark cycles is greater than 300 cycles. In embodiments, the total number of sequencing and dark cycles is greater than 350 cycles. In embodiments, the total number of sequencing and dark cycles is greater than 400 cycles. In embodiments, the total number of sequencing and dark cycles is greater than 450 cycles. In embodiments, the total number of sequencing and dark cycles is greater than 500 cycles. In embodiments, the entire process may include a total number of sequencing and dark cycles of about 1 to about 1000, 2 to 1000, 100 to 1000, 50 to 500, or 100 to 500 cycles.

In embodiments, the methods of sequencing a template nucleic acid include a first and second nucleotide, where the first and second nucleotides each independently include an identifying label. In embodiments, a particular nucleotide type is associated with a particular label, such that identifying the label identifies the nucleotide with which it is associated. In embodiments, the label is luciferin that reacts with luciferase to produce a detectable signal in response to one or more bases being incorporated into an elongated complementary strand, such as in pyrosequencing. In embodiments, the identifying label is a dye (e.g., a fluorophore). In embodiments, the label is not associated with any particular nucleotide, but detection of the label identifies whether one or more nucleotides having a known identity were added during an extension step.

In embodiments, the methods of sequencing a template nucleic acid include a first and second nucleotide, where the first and second nucleotides each include a reversible terminator, and the method further includes removing the reversible terminator. In embodiments, removal of the reversible terminator moiety occurs after detecting the nucleotide. In embodiments, the method includes one or more wash cycles.

In embodiments, the methods of sequencing a template nucleic acid include a dark cycle that terminates with the addition of a nucleotide that includes a reversible terminator. In embodiments, the methods of sequencing a template nucleic acid include a dark cycle that terminates with the incorporation of a nucleotide that includes a reversible terminator. In embodiments, the methods of sequencing a template nucleic acid include a dark cycle that terminates due to a lack of a nucleotide complementary to a position in the template nucleic acid (e.g., when using a limited-extension solution that does not contain all of the nucleotide types necessary for continuous nucleic acid extension).

In embodiments, the methods of sequencing a template nucleic acid include a plurality of dark cycles. In embodiments, the plurality of dark cycles includes about 1 to about 100, or about 20 to about 50 dark cycles. In embodiments, the plurality of dark cycles is about 1, 2, 5, 10, 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 cycles. In embodiments, the plurality of dark cycles is about 2 cycles. In embodiments, the plurality of dark cycles is about 5 cycles. In embodiments, the plurality of dark cycles is about 10 cycles. In embodiments, the plurality of dark cycles is about 20 cycles. In embodiments, the plurality of dark cycles is about 30 cycles. In embodiments, the plurality of dark cycles is about 40 cycles. In embodiments, the plurality of dark cycles is about 50 cycles. In embodiments, the plurality of dark cycles is greater than 50 cycles. In embodiments, the plurality of dark cycles includes greater than 100, 200, 300 400 or 500 cycles.

In embodiments, the methods of sequencing a template nucleic acid include a plurality of dark cycles and the nucleotide including the reversible terminator is the same type (e.g., a dT nucleotide is terminated and used in all the dark cycles) in the plurality of dark cycles.

In embodiments, the methods of sequencing a template nucleic acid include four different nucleotides that are present during the sequence extending steps and each nucleotide is labeled differently. Various methods for labeling nucleotides differently are available. In embodiments, each type of nucleotide (e.g., dA, dT, dG, and dC) comprise a label that is unique to that type, such as a fluorescent dye that is excited by and/or emits a wavelength that is different from fluorescent dyes associated with the other types. In embodiments, all four types of nucleotides are labeled differently by way of different combinations of labels. For example, using only two labels (e.g., two dyes) "a" and "b," the distinct combinations would be "a" alone, "b" alone, "a"+"b", and no label. As this example illustrates, in embodiments, labeling different types of nucleotides differently includes a type of nucleotide that is identifiable by the absence of a label. A further such example would be the use of a different label for each of three types of nucleotides, and no label for the fourth type.

In embodiments, the methods of sequencing a template nucleic acid include a label. In embodiments, the label is a fluorescent label. In embodiments, the identifying label is a dye.

In embodiments, the methods of sequencing a template nucleic acid include a total number of sequencing cycles of about 1 to about 100, or about 20 to about 50. In embodiments, the total number of sequencing cycles is about 1, 2, 5, 10, 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 cycles. In embodiments, the total number of sequencing cycles is about 2 cycles. In embodiments, the total number of sequencing cycles is about 5 cycles. In embodiments, the total number of sequencing cycles is about 10 cycles. In embodiments, the total number of sequencing cycles is about 20 cycles. In embodiments, the total number of sequencing cycles is about 30 cycles. In embodiments, the total number of sequencing cycles is about 40 cycles. In embodiments, the total number of sequencing cycles is about 50 cycles. In embodiments, the total number of sequencing cycles is greater than 50 cycles. In embodiments, the total number of sequencing cycles is greater than 100 cycles. In embodiments, the total number of sequencing cycles is greater than 150 cycles. In embodiments, the total number of sequencing cycles is greater than 200 cycles. In embodiments, the total number of sequencing cycles is greater than 250 cycles.

In embodiments, the methods of sequencing a template nucleic acid include a total number of dark cycles of about 1 to about 100, or about 20 to about 50. In embodiments, the total number of dark cycles is about 1, 2, 5, 10, 15, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 cycles. In embodiments, the total number of dark cycles is about 2 cycles. In embodiments, the total number of dark cycles is about 5 cycles. In embodiments, the total number of dark cycles is about 10 cycles. In embodiments, the total number of dark cycles is about 20 cycles. In embodiments, the total number of dark cycles is about 30 cycles. In embodiments, the total number of dark cycles is about 40 cycles. In embodiments, the total number of dark cycles is about 50 cycles. In embodiments, the total number of dark cycles is greater than 50 cycles.

In embodiments, the methods of sequencing a template nucleic acid produce one or more sequencing reads including joined discontinuous nucleic acid sequences collectively spanning a length of about 100 to about 5000 bases or more of a template nucleic acid. In embodiments, the methods of sequencing a template nucleic acid produce one or more sequencing reads including joined discontinuous nucleic acid sequences collectively spanning a length of about 500 to about 4500, about 1000 to about 4000, about 1500 to about 3500, about 2000 to about 3000, or about 2500 bases of a template nucleic acid. In embodiments, the methods of sequencing a template nucleic acid produce one or more sequencing reads including joined discontinuous nucleic acid sequences collectively spanning a length of about 100, 200, 300, 400, 500, 600, 700, 800, 900, 1000, 1500, 2000, 2500, 3000, 3500, 4000, 4500, or 5000 bases of a template nucleic acid. In embodiments, the methods of sequencing a template nucleic acid produce one or more sequencing reads including joined discontinuous nucleic acid sequences collectively spanning a length of about 50, 60, 70, 80, 90, 100, 125, 150, 175, 200, 225, 250, 275, 300, 325, 350, 375, 400, 425, 450, 475, or 500 bases of a nucleic acid template. In embodiments, the methods of sequencing a template nucleic acid produce one or more sequencing reads including joined discontinuous nucleic acid sequences collectively spanning a length of about 100 bases of a template nucleic acid. In embodiments, the methods of sequencing a template nucleic acid produce one or more sequencing reads including joined discontinuous nucleic acid sequences collectively spanning a length of about 500 bases of a template nucleic acid. In embodiments, the methods of sequencing a template nucleic acid produce one or more sequencing reads including joined discontinuous nucleic acid sequences collectively spanning a length of about 700 bases of a template nucleic acid. In embodiments, the methods of sequencing a template nucleic acid produce one or more sequencing reads including joined discontinuous nucleic acid sequences collectively spanning a length of about 1000 bases of a template nucleic acid. In embodiments, the methods of sequencing a template nucleic acid produce one or more sequencing reads including joined discontinuous nucleic acid sequences collectively spanning a length of about 3000 bases of a template nucleic acid. In embodiments, the methods of sequencing a template nucleic acid produce one or more sequencing reads including joined discontinuous nucleic acid sequences collectively spanning a length of more than 1 kb, 2 kb, 3 kb, 4 kb, or 5 kb of the template nucleic acid. In embodiments, the methods of sequencing a template nucleic acid produce one or more sequencing reads including joined discontinuous nucleic acid sequences collectively spanning a length of more than 5 kb, 6 kb, 7 kb, 8 kb, 9 kb, or 10 kb of the template nucleic acid. In embodiments, the methods of sequencing a template nucleic acid produce one or more sequencing reads including joined discontinuous nucleic acid sequences collectively spanning a length of about 3 kb to 8 kb of the template nucleic acid.

In embodiments, the methods of sequencing a template nucleic acid further include aligning the one or more sequencing reads to a reference sequence. General methods for performing sequence alignments are known to those skilled in the art. Examples of suitable alignment algorithms, include but not limited to the Needleman-Wunsch algorithm (see e.g. the EMBOSS Needle aligner available at www.ebi.ac.uk/Tools/psa/emboss_needle/, optionally with default settings), the BLAST algorithm (see e.g. the BLAST alignment tool available at blast.ncbi.nlm.nih.gov/Blast.cgi, optionally with default settings), or the Smith-Waterman algorithm (see e.g. the EMBOSS Water aligner available at www.ebi.ac.uk/Tools/psa/emboss_water/, optionally with default settings). Optimal alignment may be assessed using any suitable parameters of a chosen algorithm, including default parameters.

In embodiments, the methods of sequencing a template nucleic acid further include generating overlapping sequence reads and assembling them into a contiguous nucleotide sequence of a nucleic acid of interest. Assembly algorithms known in the art can align and merge overlapping sequence reads generated by methods of several embodiments herein to provide a contiguous sequence of a nucleic acid of interest. A person of ordinary skill in the art will understand which sequence assembly algorithms or sequence assemblers are suitable for a particular purpose taking into account the type and complexity of the nucleic acid of interest to be sequenced (e.g. genomic, PCR product, or plasmid), the number and/or length of deletion products or other overlapping regions generated, the type of sequencing methodology performed, the read lengths generated, whether assembly is de novo assembly of a previously unknown sequence or mapping assembly against a backbone sequence, etc. Furthermore, an appropriate data analysis tool will be selected based on the function desired, such as alignment of sequence reads, base-calling and/or polymorphism detection, de novo assembly, assembly from paired or unpaired reads, and genome browsing and annotation. In several embodiments, overlapping sequence reads can be assembled by sequence assemblers, including but not limited to ABySS, AMOS, Arachne WGA, CAP3, PCAP, Celera WGA Assembler/CABOG, CLC Genomics Workbench, CodonCode Aligner, Euler, Euler-sr, Forge, Geneious, MIRA, miraEST, NextGENe, Newbler, Phrap, TIGR Assembler, Sequencher, SeqMan NGen, SHARCGS, SSAKE, Staden gap4 package, VCAKE, Phusion assembler, Quality Value Guided SRA (QSRA), SPAdes, Velvet (algorithm), and the like.

It will be understood that overlapping sequence reads can also be assembled into contigs or the full contiguous sequence of the nucleic acid of interest by available means of sequence alignment, computationally or manually, whether by pairwise alignment or multiple sequence alignment of overlapping sequence reads. Algorithms suited for short-read sequence data may be used in a variety of embodiments, including but not limited to Cross_match, ELAND, Exonerate, MAQ, Mosaik, RMAP, SHRiMP, SOAP, SSAHA2, SXOligoSearch, ALLPATHS, Edena, Euler-SR, SHARCGS, SHRAP, SSAKE, VCAKE, SPAdes, Velvet, PyroBayes, PbShort, and ssahaSNP.

In embodiments, the methods of sequencing a template nucleic acid further include generating a consensus sequence for the template nucleic acid and/or its complement from the alignment of one or more sequencing reads.

In embodiments, the methods of sequencing a template nucleic acid include generating a consensus sequence that includes (i) a nucleic acid sequence in one or more first sequencing reads that is absent from one or more second sequencing reads, and (ii) a nucleic acid sequence in one or more of the second sequencing reads that is absent from the one or more first sequencing reads. For example, nucleotide positions that were extended during a dark cycle for one template may be combined with sequence information for the corresponding positions identified during a sequencing cycle of an overlapping template nucleic acid. Multiple sequencing reads spanning the same region but with different start and stop positions for sequencing and dark cycles can be collapsed into a consensus sequence that combines sequencing information from the various sequencing cycles.

In embodiments, the methods of sequencing a template nucleic acid include a sequencing cycle where each sequencing cycle includes contacting the complementary polynucleotide with a sequencing solution, where the sequencing solution includes one or more nucleotides, where each nucleotide includes a detectable label and a reversible terminator. In embodiments, the methods of sequencing a template nucleic acid include a sequencing cycle where each sequencing cycle includes contacting the complementary polynucleotide with a sequencing solution, where the sequencing solution includes one or more nucleotides, where each nucleotide includes a reversible terminator.

In embodiments, the methods of sequencing a template nucleic acid include a sequencing solution. In embodiments, the sequencing solution includes (a) an adenine nucleotide, or analog thereof; (b) (i) a thymine nucleotide, or analog thereof, or (ii) a uracil nucleotide, or analog thereof; (c) a cytosine nucleotide, or analog thereof; and (d) a guanine nucleotide, or analog thereof. In embodiments, the sequencing solution includes a plurality of adenine nucleotides, or analogs thereof; a plurality of thymine nucleotides, or analogs thereof, or a plurality of uracil nucleotides, or analogs thereof; a plurality of cytosine nucleotides, or analogs thereof; and a plurality of guanine nucleotides, or analogs thereof. In embodiments, each sequencing cycle includes contacting the complementary polynucleotide with a sequencing solution, wherein the sequencing solution comprises one or more nucleotides, wherein each nucleotide comprises a reversible terminator. In embodiments, each sequencing cycle includes contacting the complementary polynucleotide with a sequencing solution, wherein the sequencing solution comprises one or more nucleotides, wherein each nucleotide comprises a reversible terminator and a label. In embodiments, the sequencing solution includes one or more nucleotides, wherein each nucleotide includes a label and reversible terminator, with the exception of one nucleotide type (e.g., all dTs of the sequencing solution), which includes a reversible terminator but no label.

In embodiments, the methods of sequencing a template nucleic acid include a dark cycle. Each dark cycle includes contacting the complementary polynucleotide with a dark solution, where the dark solution includes one or more nucleotides, and where at least one nucleotide type comprises a reversible terminator. In embodiments, all nucleotides of only one type include a reversible terminator (e.g., all "G" nucleotides are terminated, all "C" nucleotides are terminated, all "A" nucleotides are terminated, or all "T" nucleotides are terminated).

In embodiments, the methods of sequencing a template nucleic acid include a dark solution. In embodiments, the dark solution includes (a) an adenine nucleotide, or analog thereof; (b) (i) a thymine nucleotide, or analog thereof, or (ii) a uracil nucleotide, or analog thereof; (c) a cytosine nucleotide, or analog thereof; and (d) a guanine nucleotide, or analog thereof. In embodiments, the dark solution includes a plurality of adenine nucleotides, or analogs thereof; a plurality of thymine nucleotides, or analogs thereof, or a plurality of uracil nucleotides, or analogs thereof; a plurality of cytosine nucleotides, or analogs thereof; and a plurality of guanine nucleotides, or analogs thereof. In embodiments, the dark solution includes a plurality of one to three of nucleotide types selected from the following: a plurality of adenine nucleotides, or analogs thereof; a plurality of thymine nucleotides, or analogs thereof, or a plurality of uracil nucleotides, or analogs thereof a plurality of cytosine nucleotides, or analogs thereof and a plurality of guanine nucleotides, or analogs thereof. In embodiments, the dark solution includes four nucleotide types (e.g., dA, dT, dC, and dG). In embodiments, the dark solution includes three nucleotide types (e.g., dA, dT, and dG). In embodiments, the dark solution includes a plurality of one to three of nucleotide types selected from the following: a plurality of adenine nucleotides, or analogs thereof a plurality of thymine nucleotides, or analogs thereof, or a plurality of uracil nucleotides, or analogs thereof a plurality of cytosine nucleotides, or analogs thereof and a plurality of guanine nucleotides, or analogs thereof. In embodiments, one plurality of nucleotide types includes a reversible terminator.

In embodiments, the dark solution is identical to the sequencing solution, and is contacted with a cleaving agent prior to nucleotide incorporation. In embodiments, the dark solution is identical to the sequencing solution, and is contacted with a cleaving agent during nucleotide incorporation. In embodiments, the dark solution is identical to the sequencing solution, and is contacted with a cleaving agent after nucleotide incorporation.

In embodiments, the methods of sequencing a template nucleic acid include a dark solution where at least one nucleotide includes a reversible terminator. In embodiments, the methods of sequencing a template nucleic acid include a dark solution where one nucleotide type includes a reversible terminator. In embodiments, the methods of sequencing a template nucleic acid include a dark solution that includes four nucleotide types where one nucleotide type includes a reversible terminator. In embodiments, the dark solution includes a reversible terminated cytosine ($C_t$). In embodiments, the dark solution includes a reversible terminated adenine ($A_t$). In embodiments, the dark solution includes a reversible terminated guanine ($G_t$). In embodiments, the dark solution includes a reversible terminated thymine ($T_t$). In embodiments, the dark solution includes a plurality of reversible terminated cytosines ($C_t$). In embodiments, the dark solution includes a plurality of reversible terminated adenines ($A_t$). In embodiments, the dark solution includes a plurality of reversible terminated guanines ($G_t$). In embodiments, the dark solution includes a plurality of reversible terminated thymines ($T_t$).

In embodiments, the dark solution is a limited-extension solution. The limited-extension solution reaction mixture includes a plurality of nucleotides or analogs thereof wherein one, two, or three of the following nucleotide types are omitted from the dark solution: (a) adenine nucleotides and analogs thereof (b) (i) thymine nucleotides and analogs thereof, and (ii) uracil nucleotides and analogs thereof; (c) cytosine nucleotides and analogs thereof; or (iv) guanine nucleotides and analogs thereof. In embodiments, adenine nucleotides and analogs thereof are omitted. In embodiments, thymine nucleotides and analogs thereof, and uracil nucleotides and analogs thereof are omitted. In embodiments, cytosine nucleotides and analogs thereof are omitted. In embodiments, guanine nucleotides and analogs thereof are omitted.

In embodiments, the dark solution includes a plurality of adenine nucleotides, or analogs thereof; thymine nucleotides, or analogs thereof, and cytosine nucleotides, or analogs thereof, and does not include a plurality of guanine nucleotides or analogs thereof. In embodiments, the dark solution includes a plurality of adenine nucleotides, or analogs thereof; thymine nucleotides, or analogs thereof, and guanine nucleotides, or analogs thereof, and does not include a plurality of cytosine nucleotides or analogs thereof. In embodiments, the dark solution includes a plurality of adenine nucleotides, or analogs thereof; guanine nucleotides, or analogs thereof, and cytosine nucleotides, or analogs thereof, and does not include a plurality of thymine nucleotides or analogs thereof. In embodiments, the dark solution includes a plurality of guanine nucleotides, or analogs thereof; thymine nucleotides, or analogs thereof, and cytosine nucleotides, or analogs thereof, and does not include a plurality of adenine nucleotides or analogs thereof.

In embodiments, the limited-extension solution includes a plurality of adenine nucleotides, or analogs thereof; thymine nucleotides, or analogs thereof, and cytosine nucleotides, or analogs thereof, and does not include a plurality of guanine nucleotides or analogs thereof. In embodiments, the limited-extension solution includes a plurality of adenine nucleotides, or analogs thereof; thymine nucleotides, or analogs thereof, and guanine nucleotides, or analogs thereof, and does not include a plurality of cytosine nucleotides or analogs thereof. In embodiments, the limited-extension solution includes a plurality of adenine nucleotides, or analogs thereof; guanine nucleotides, or analogs thereof, and cytosine nucleotides, or analogs thereof, and does not include a plurality of thymine nucleotides or analogs thereof. In embodiments, the limited-extension solution includes a plurality of guanine nucleotides, or analogs thereof; thymine nucleotides, or analogs thereof, and cytosine nucleotides, or analogs thereof, and does not include a plurality of adenine nucleotides or analogs thereof.

A variety of suitable sequencing platforms are available for implementing methods disclosed herein. Non-limiting examples include SMRT (single-molecule real-time sequencing), ion semiconductor, pyrosequencing, sequencing by synthesis, combinatorial probe anchor synthesis, SOLiD sequencing (sequencing by ligation), and nanopore sequencing. Sequencing platforms include those provided by Illumina® (e.g., the HiSeq™, MiSeg™ and/or Genome Analyzer™ sequencing systems); Ion Torrent™ (e.g., the Ion PGM™ and/or Ion Proton™. sequencing systems); Pacific Biosciences (e.g., the PACBIO RS II sequencing system); Life Technologies™ (e.g., a SOLiD sequencing system); Roche (e.g., the 454 GS FLX+ and/or GS Junior sequencing systems). See, for example U.S. Pat. Nos. 7,211,390; 7,244,559; 7,264,929; 6,255,475; 6,013,445; 8,882,980; 6,664,079; and 9,416,409. Useful pyrosequencing reactions are described, for example, in US Patent Application Publication No. 2005/0191698 and U.S. Pat. No. 7,244,559, each of which is incorporated herein by reference. Sequencing-by-ligation reactions are described, for example, in Shendure et al. Science 309:1728-1732 (2005); U.S. Pat. Nos. 5,599,675; and 5,750,341, each of which is incorporated herein by reference in its entirety.

In an aspect is a method of sequencing a template nucleic acid and identifying a gene fusion event. In an aspect is a method of sequencing C-V-D-J regions of an RNA transcript. In an aspect is a method of identifying the bacterial species by analyzing a 16S RNA sequence. In an aspect is a method of analyzing an alternative splicing (AS) event in a template nucleic acid. For the aforementioned aspects, the methods include sequencing a template nucleic acid and assembling the sequencing reads as described herein, including examples and embodiments.

Kits

In an aspect, provided herein are kits for use in accordance with any of the methods disclosed herein, and including one or more elements thereof. In embodiments, a kit includes labeled nucleotides including four differently labeled nucleotides, where the label identifies the type of nucleotide, unlabeled nucleotides lacking a reversible terminator; and unlabeled nucleotides including a reversible terminator. In embodiments, the kit further includes instructions for use thereof. In embodiments, a kit includes labeled nucleotides including four or fewer differently labeled nucleotides, where the label identifies the type of nucleotide, unlabeled nucleotides lacking a reversible terminator; and unlabeled nucleotides including a reversible terminator.

In embodiments, kits described herein include labeled nucleotides including four differently labeled nucleotides, where the label identifies the type of nucleotide. For example, each of an adenine nucleotide, or analog thereof; a thymine nucleotide; a cytosine nucleotide, or analog thereof; and a guanine nucleotide, or analog thereof may be labelled with a different fluorescent label, or a different combination of labels. In embodiments, the adenine nucleotide, or analog thereof a thymine nucleotide; a cytosine nucleotide, or analog thereof and a guanine nucleotide, or analog thereof may be labelled with a different fluorescent label (or different combination of labels) and one may unlabeled.

In embodiments, the kit includes labeled nucleotides including four or fewer differently labeled nucleotides, wherein the label identifies the type of nucleotide, and (b) unlabeled nucleotides lacking a reversible terminator. In embodiments, the kit includes labeled nucleotides comprising four or fewer differently labeled nucleotides, wherein the label identifies the type of nucleotide.

In embodiments, kits described herein include unlabeled nucleotides lacking a reversible terminator. In embodiments, kits described herein include unlabeled nucleotides including a reversible terminator. In embodiments, kits described herein include labeled nucleotides including a reversible terminator. In embodiments, kits described herein include labeled nucleotides without a reversible terminator.

In embodiments, kits described herein include a polymerase. In embodiments, the polymerase is a DNA polymerase. In embodiments, the DNA polymerase is a thermophilic nucleic acid polymerase. In embodiments, the DNA polymerase is a modified archaeal DNA polymerase.

In an aspect, provided herein are reaction mixtures for use in accordance with any of the methods disclosed herein, and including one or more elements thereof. In embodiments, a reaction mixture includes labeled nucleotides including four differently labeled nucleotides, where the label identifies the type of nucleotide, unlabeled nucleotides lacking a reversible terminator; unlabeled nucleotides including a reversible terminator; and a polymerase.

In embodiments, reaction mixtures described herein include labeled nucleotides including four differently labeled nucleotides, where the label identifies the type of nucleotide. For example, each of an adenine nucleotide, or analog thereof, a thymine nucleotide; a cytosine nucleotide, or analog thereof; and a guanine nucleotide, or analog thereof may be labelled with a different fluorescent label. In embodiments, three of an adenine nucleotide, or analog thereof, a thymine nucleotide; a cytosine nucleotide, or analog thereof, and a guanine nucleotide, or analog thereof may be labelled with a different fluorescent label and one may unlabeled.

In embodiments, reaction mixtures described herein include unlabeled nucleotides lacking a reversible terminator. In embodiments, kits described herein include unlabeled nucleotides including a reversible terminator.

In embodiments, reaction mixtures described herein include a polymerase. In embodiments, the polymerase is a DNA polymerase. In embodiments, the DNA polymerase is a thermophilic nucleic acid polymerase. In embodiments, the DNA polymerase is a modified archaeal DNA polymerase (e.g., a modified archaeal DNA polymerase described herein). In embodiments, the polymerase in the kit is a bacterial DNA polymerase, eukaryotic DNA polymerase, archaeal DNA polymerase, viral DNA polymerase, or phage DNA polymerases. Bacterial DNA polymerases include E. coli DNA polymerases I, II and III, IV and V, the Klenow fragment of E. coli DNA polymerase, Clostridium stercorarium (Cst) DNA polymerase, Clostridium thermocellum (Cth) DNA polymerase and Sulfolobus solfataricus (Sso) DNA polymerase. Eukaryotic DNA polymerases include DNA polymerases α, β, γ, δ, €, η, ζ, λ, σ, μ, and k, as well as the Revl polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cpl DNA polymerase, Cpl DNA polymerase, T7 DNA polymerase, and T4 polymerase. Other useful DNA polymerases include thermostable and/or thermophilic DNA polymerases such as *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. In embodiments, the polymerase is a 3PDX polymerase as disclosed in U.S. Pat. No. 8,703,461, the disclosure of which is incorporated herein by reference. In embodiments, the polymerase is a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, or Telomerase reverse transcriptase. In embodiments, the polymerase is a mutant *P. abyssi* polymerase (e.g., such as a mutant *P. abyssi* polymerase described in WO 2018/148723 or WO 2020/056044, each of which are incorporated herein by reference for all purposes). In embodiments, the kit includes a strand-displacing polymerase. In embodiments, the kit includes a strand-displacing polymerase, such as a phi29 polymerase, phi29 mutant polymerase or a thermostable phi29 mutant polymerase.

In embodiments, the reaction mixtures include a buffer solution. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, Tricine, HEPES, TES, MOPS, MOPSO and PIPES. Additionally, other buffer agents that can be used in enzyme reactions, hybridization reactions, and detection reactions are well known in the art. In embodiments, the buffered solution can include Tris. With respect to the embodiments described herein, the pH of the buffered solution can be modulated to permit any of the described reactions. In some embodiments, the buffered solution can have a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In other embodiments, the buffered solution can have a pH ranging, for example, from about pH 6 to about pH 9, from about pH 8 to about pH 10, or from about pH 7 to about pH 9. In embodiments, the buffered solution can comprise one or more divalent cations. Examples of divalent cations can include, but are not limited to, $Mg^{2+}$, $Mn^{2+}$, $Zn^{2+}$ and $Ca^{2+}$.

In embodiments, the buffered solution can contain one or more divalent cations at a concentration sufficient to permit hybridization of a nucleic acid. In some embodiments, a concentration can be more than about 1 µM, more than about 2 µM, more than about 5 µM, more than about 10 µM, more than about 25 µM, more than about 50 µM, more than about 75 µM, more than about 100 µM, more than about 200 µM, more than about 300 µM, more than about 400 µM, more than about 500 µM, more than about 750 µM, more than about 1 mM, more than about 2 mM, more than about 5 mM, more than about 10 mM, more than about 20 mM, more than about 30 mM, more than about 40 mM, more than about 50 mM, more than about 60 mM, more than about 70 mM, more than about 80 mM, more than about 90 mM, more than about 100 mM, more than about 150 mM, more than about 200 mM, more than about 250 mM, more than about 300 mM, more than about 350 mM, more than about 400 mM, more than about 450 mM, more than about 500 mM, more than about 550 mM, more than about 600 mM, more than about 650 mM, more than about 700 mM, more than about 750 mM, more than about 800 mM, more than about 850 mM, more than about 900 mM, more than about 950 mM or more than about 1M.

Adapters and/or primers may be supplied in the kits ready for use, or more preferably as concentrates-requiring dilution before use, or even in a lyophilized or dried form requiring reconstitution prior to use. If required, the kits may further include a supply of a suitable diluent for dilution or reconstitution of the primers. Optionally, the kits may further include supplies of reagents, buffers, enzymes, and dNTPs for use in carrying out nucleic acid amplification and/or sequencing. Further components which may optionally be supplied in the kit include sequencing primers suitable for sequencing templates prepared using the methods described herein.

EXAMPLES

Example 1: Long Read Sequencing Method

Provided herein are sequencing methods that include alternating a series of sequencing and extending cycles allowing longer read lengths. In a general sense, the methods and kits described herein provide detection of a nucleic acid that allows data collection at noncontiguous regions of a nucleic acid.

Described herein is a method for sequencing a template nucleic acid, the method including a plurality of sequencing-cycles and a plurality of dark cycles (depicted in FIG. 1). The method includes (a) executing a sequencing cycle that includes (i) extending a complementary polynucleotide that is hybridized to the template nucleic acid by incorporating a first nucleotide using a polymerase; and (ii) detecting a label that identifies the first nucleotide; (b) extending the complementary polynucleotide in one or more dark cycles, where each dark cycle includes extending the complementary polynucleotide by one or more nucleotides using the polymerase, without performing a detection event to identify nucleotides incorporated during the dark cycle; and (c) executing a sequencing cycle that includes (i) extending the complementary polynucleotide by incorporating a second nucleotide using a polymerase; and (ii) detecting a label that identifies the second nucleotide, thereby sequencing a template nucleic acid.

The methods may include (a) executing a sequencing cycle including (i) extending a complementary polynucleotide that is hybridized to the template nucleic acid by incorporating a first nucleotide using a polymerase; where said nucleotide includes a reversible terminator moiety, and (ii) detecting a label that identifies the first nucleotide; (b) extending the complementary polynucleotide in one or more dark cycles, where each dark cycle includes extending the complementary polynucleotide by at least two nucleotides using the polymerase; wherein at least one nucleotide does not comprise a reversible terminator, and one nucleotide comprises a reversible terminator moiety, optionally performing a detection event to identify nucleotides incorporated during the dark cycle; and (c) executing a sequencing cycle including (i) extending the complementary polynucleotide by incorporating a second nucleotide using a polymerase; wherein said nucleotide comprises a reversible terminator moiety, and (ii) detecting a label that identifies the second nucleotide, thereby sequencing a template nucleic acid.

Executing a sequencing cycle includes (i) incorporating in series with a nucleic acid polymerase, one of four differently labeled nucleotide analogues into a nucleic acid strand complementary to the template nucleic acid to create a sequenced-extension strand, where each of the four differently labeled nucleotide analogues include a detectable label; and (ii) detecting the unique detectable label of each incorporated nucleotide analogue, so as to thereby identify each incorporated nucleotide analogue in the sequenced-extension strand.

Sequence data is collected for a first portion of the template nucleic acid under a first set of reaction conditions as the template nucleic acid is extended to generate an extension strand, for example by traditional sequence by synthesis (SBS) methodologies. Following a defined number of sequencing cycles (i.e., a series of nucleotide extension steps that are sequenced), the reaction conditions are changed to a second set of reaction conditions to initiate a limited-extension (LE) or dark cycle. The cycle is referred to as 'dark' since during this cycle, sequencing (i.e., nucleotide identification) is not taking place.

Each dark cycle includes extending the complementary polynucleotide by one or more nucleotides using the polymerase, without performing a detection event to identify nucleotides incorporated during the dark cycle. During a dark cycle, the extension strand from the nucleotide extension step completed during the sequencing cycle, referred to as the sequenced-extension strand, is elongated with nucleotides (e.g., native nucleotides) under a second set of reaction conditions. The extension strand generated during this limited-extension or dark cycle may be referred to as the dark-extension strand and is contiguous with the extension strand generated from the sequencing cycle. The identity of each nucleic acid incorporated into the nascent nucleic acid strand is not monitored during a dark or LE cycle. Any number of native nucleotides may be incorporated into the dark-extension strand until a nucleotide analogue having a polymerase-compatible cleavable moiety (i.e., a reversible terminator moiety) is incorporated, which temporarily halts the polymerase reaction until the moiety is removed. Once the moiety is removed, another sequencing cycle or an additional dark cycle may be initiated. In embodiments, a series of dark cycles are performed before changing the reaction conditions to perform a series of sequencing cycles.

In some embodiments, the dark cycle includes extending the complementary polynucleotide by at least two nucleotides using the polymerase; where at least one nucleotide does not include a reversible terminator, and at least one nucleotide includes a reversible terminator moiety and a label, and optionally performing a detection event to identify nucleotides incorporated during the dark cycle. This process would enable detecting the labeled nucleotide as a quality control measure, for example to check the synchronization of the process.

In other embodiments, the dark cycle includes extending the complementary polynucleotide by one or more nucleotides using a polymerase; where the extension is accomplished by a pool of native nucleotides lacking at least one of the four bases. For example, the dark cycle may include extending the complementary nucleotide in the presence of three nucleotides, e.g., dA, dG, and dC. The cycles of extension may continue until the complement of the missing nucleotide, e.g., dT, is necessary to continue extension.

In other embodiments, the dark cycle includes extending the complementary polynucleotide by one or more nucleotides using a polymerase; where the extension is accomplished by a pool of modified nucleotides having a reversible terminator moiety and/or a label moiety, while a second agent is contemporaneously applied to remove the label and termination moieties from the nucleotides. For example, the extension mixture in a dark cycle may include contact with a second agent capable of cleaving or removing the reversible terminator and/or the label. In embodiments, the second agent is a cleaving agent, such as a reducing agent. If the nucleotides are mixed with a cleaving agent prior to introduction, or during transit, or within the flow cell, the reversible terminator and/or label are removed and extension is permitted so long as the deblocked nucleotide extension mixture is in contact with the complementary polynucleotide. Alternatively, the extension mixture may contain nucleotides where one or more of the four nucleotide bases is absent, such that extension is halted when the extending strand reaches a base on the template molecule whose complement is one of the absent bases.

Figure 2:
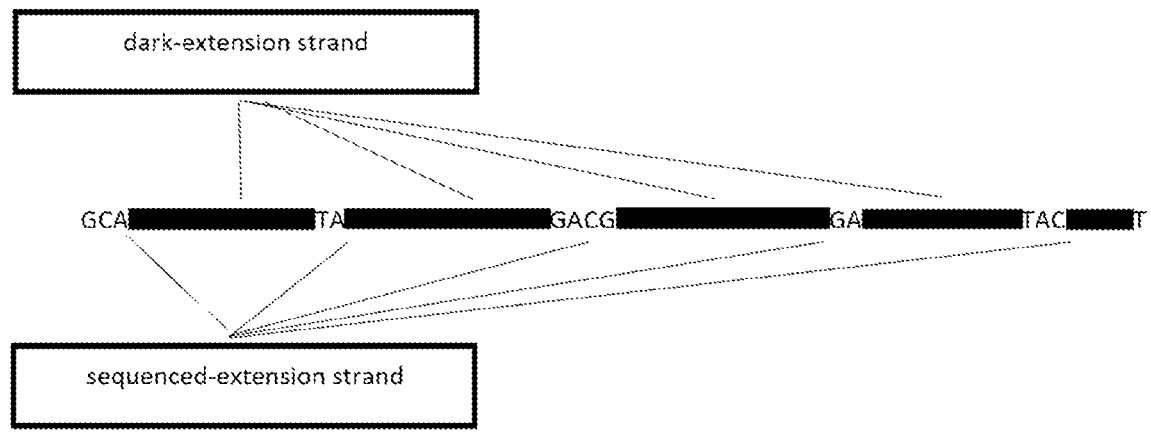
FIG. 2 depicts a template nucleic acid sequence that is subjected to an interval sequencing reaction. Following alternating sequencing and dark cycles (the dark cycles may be referred to as limited-extension or LE cycles), a complementary interval sequenced nucleic acid template is formed wherein sequenced-extension strands correspond to the complement of portions of the template nucleic acid sequence. The sequence reported in this figure corresponds to SEQ ID NO: 9.

Following a plurality of dark cycles, a sequencing cycle, or a plurality of sequencing cycles, may be reinstated, whereby the extension strand from the limited-extension cycle (i.e. the dark-extension strand) is elongated in the presence of a polymerase and labeled nucleotide analogues. The sequence data is collected from a portion of the template nucleic acid sequence which is contiguous with the dark-extension strand, but not contiguous with the sequenced-extension strand from the first nucleic acid sequencing reaction. An example of the sequenced-extension/dark-extension strand is found in FIG. 2. When combined with a distribution of nucleic acid fragments and the massive parallelization that next-generation sequencing technology affords, in embodiments, the methods described herein may increase the sequencing read length to 500-1000 base pairs of a region of a reference sequence.

Dark Cycle

By way of example, the dark cycle may include incorporating into the extension strand either native nucleotides (e.g., natural A, C, and G) or a terminated nucleotide analogue (e.g., $T_t$), or a combination thereof, where the terminated nucleotide analogue includes a polymerase-compatible cleavable moiety on the 3'-oxygen atom (also referred to herein as a reversible terminated nucleotide). During the dark cycle, with the extension solution including for example native nucleotides A, C, G, and a terminated nucleotide, $T_t$, where $T_t$ represents a thymine nucleotide analogue with a polymerase-compatible cleavable moiety on the 3'-oxygen atom, the native nucleotides will continue to be incorporated until the template nucleic acid sequence is an adenine nucleotide (i.e., the complement to $T_t$). The polymerase will incorporate the $T_t$ nucleotide analogue and cease incorporation of any additional nucleotides until the polymerase-compatible cleavable moiety is removed (e.g., contacting the polymerase-compatible cleavable moiety with a cleaving agent, such as a reducing agent). Upon removal of the polymerase-compatible cleavable moiety, a new dark cycle may begin and nucleotides (e.g., native nucleotides) may be incorporated into the extension strand until another adenine nucleotide is present in the template nucleic acid.

In the above example, without inclusion of a terminated nucleotide, for example using all native nucleotides, the extension step would be uncontrolled and would require mathematical and/or computational calculations (e.g., velocity functions, correlation functions, probability determinations, or Hidden Markov models) in order to determine how much sequencing has occurred, essentially estimating the location of the polymerase on the target nucleic acid. Controlling the reaction by including at least one nucleotide containing a polymerase-compatible cleavable moiety negates the use of additional mathematical calculations or analytical techniques. Cycles may therefore be measured by the number of reversibly terminated bases that are incorporated.

By way of example, in another embodiment, a controlled dark cycle extension may be achieved by contacting template molecules with a pool of native nucleotides where one or more of the four nucleotide bases is absent. Here, the extension halts when the extending strand reaches a base on the template molecule (e.g., dA) whose complement is one of the absent bases (e.g., dT).

By way of example, in another embodiment, a controlled dark cycle extension may be achieved by contacting template molecules with a pool of reversible terminated and/or labeled nucleotides where one or more of the four nucleotide bases is absent, while contemporaneously contacting the pool of nucleotides an agent to remove the reversible terminator and/or label (e.g., cleaving the reversible terminator and/or label with a cleaving agent, such as a reducing agent). Here again, the extension halts when the extending strand reaches a base on the template molecule (e.g., dA) whose complement is one of the absent bases (e.g., dT).

The methods described herein permit faster sequencing of nucleic acid sequences with greater sequencing depth. In embodiments, the methods described herein are about or more than about 2-fold or 4-fold faster than traditional sequencing methodologies.

Example 2: Experimental Results

Methods described herein may be used for sequencing nucleic acid templates interspersed with repetitive elements (e.g., homopolymeric nucleic acid regions). These repetitive elements present major logistical and computational challenges for assembling fragments produced by traditional sequencing technologies, especially considering that approximately two-thirds of the sequence of the human genome consists of repetitive units. For example, the human genome includes minisatellite regions, repetitive motifs ranging in length from about 10-100 base pairs and can be repeated about 5 to 50 times in the genome, and short tandem repeats (STR), regions ranging in length from about 1-6 base pairs and can be repeated about 5 to 50 times in the genome (e.g., the sequence TATATATATA (SEQ ID NO:10) is a dinucleotide STR). Complicating matters, mutations lead to the gain or loss of an entire repeat unit (e.g., TATA), and sometimes two or more repeats simultaneously, which can significantly burden traditional sequencing methodologies. The α/δ, β, and γ human T-cell receptor loci contain a five-fold repeat of a trypsinogen gene that is 4,000 nucleotides in length and varies 5-10% between copies. Smaller elements, such as the approximately 300 base pair 'Alu' repeats can constitute 50-60% of the target sequence, representing almost 11% of the human genome). In certain embodiments, the methods described herein allow for determining the sequence of long templates comprising such repetitive sequences, in part because the present methods do not rely solely on sequence overlap to generate consensus sequences (for example, see FIG. 3B), but also include information about the location of the sequenced nucleotides in relation to the dark-sequenced nucleotides within the overall template. This greatly facilitates accurate assembly of sequence reads to determine the overall template sequence.

Methods. To a Kapton 8-lane flow cell, each lane was prepared according to standard methods in the art; PhiX templates of variable length were loaded in the flow cell. The sequences for the nucleic acid templates are described in Table 1. The experiment was conducted in triplicate, varying the concentration of the nucleotides from 200 nM (experiment 1), 300 nm (experiment 2), and 400 nM (experiment 3). It was concluded that varying the concentration of the nucleotides did not have a significant effect on the sequencing results.

Figure 4A:
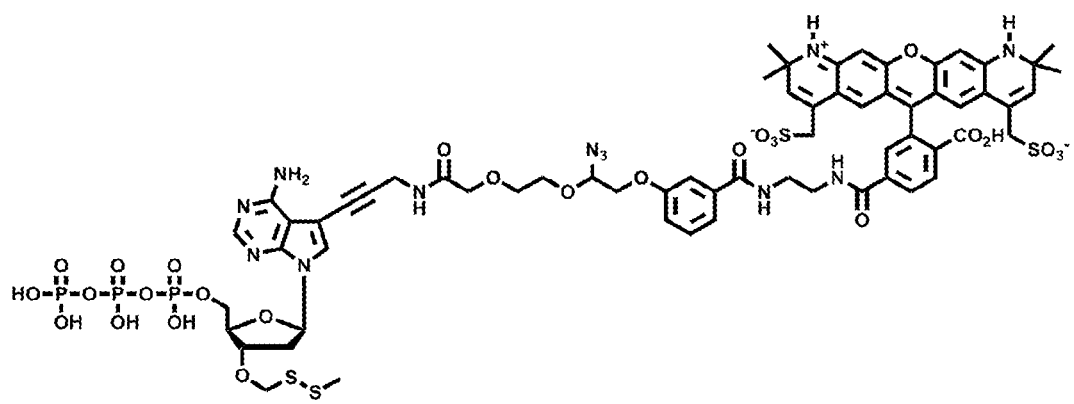
FIGS. 4A-4B illustrate example structures of labeled reversibly terminated nucleotides.
Figure 4A:
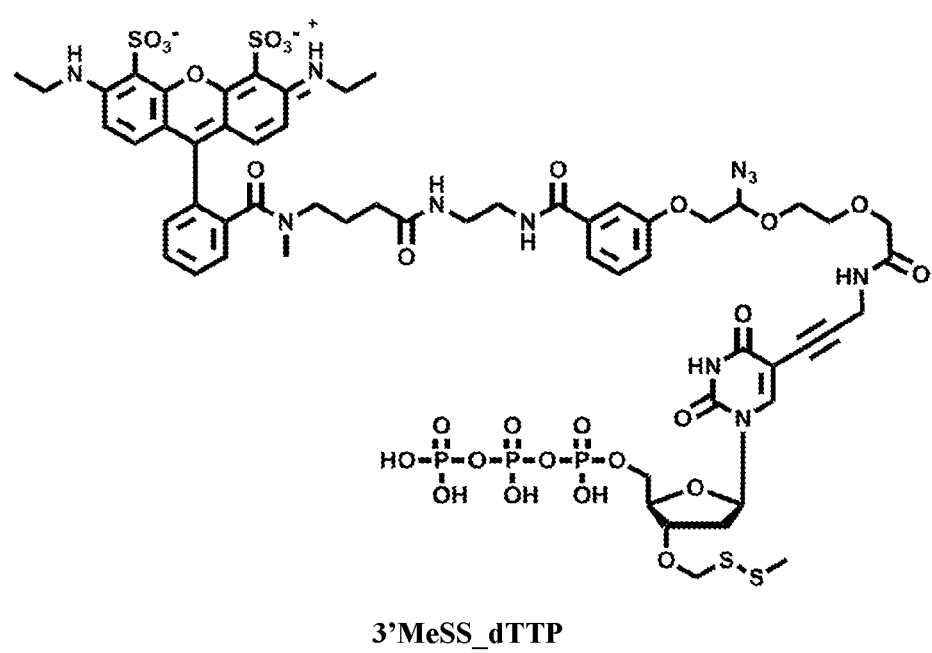

For the sequencing cycles, 200-400 nM of labeled reversibly terminated nucleotides (dNTPC-SSme, dNTPT-SSme, dNTPA-SSme, and dNTPG-SSme) and 133 nM of a DNA polymerase in a buffer were added to the lanes. The labeled reversibly terminated nucleotides are depicted in FIGS. 4A-4B.

Figure 4B:
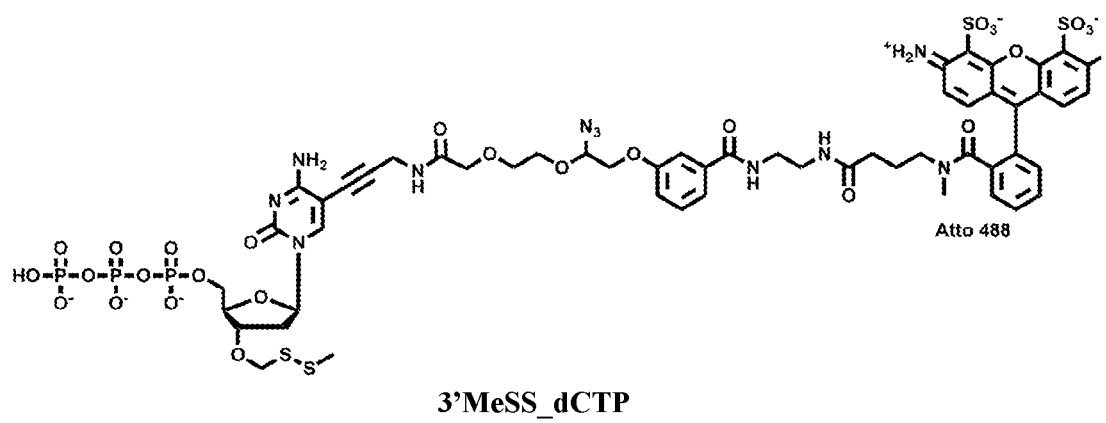
Figure 4B:
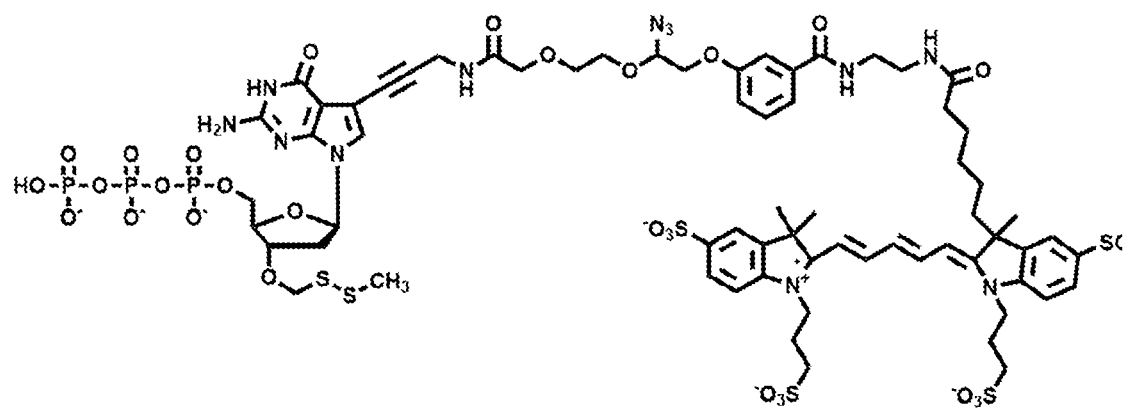

For a dark cycle, 200-400 nM of native nucleotides adenine (A), thymine (T), and guanine (G), 200 nM of reversible terminated cytosine (CO, the structure of which may be observed in FIG. 4B, and 133 nM of a DNA polymerase in a buffer were added to the lanes.

The buffer includes borate, ammonium sulfate, KCl, Mg, Triton X, EDTA, and DPDS and was maintained at pH 8.5. The reversible terminators were cleaved using THPP in a buffer solution at pH 9.5. The temperature was maintained at 65° C.

The experiment was conducted such that 10 consecutive sequencing cycles occurred (i.e., 10 bases were sequenced), followed by 8 dark cycles (i.e. 8 terminated nucleotides were incorporated). The series of consecutive cycles were repeated (10 sequencing cycles, 8 dark cycles, 10 sequencing cycles, 8 dark cycles, etc.) five times.

TABLE 1

Templates subjected to sequencing-dark cycles.

| Template | Length | Sequences |
|---|---|---|
| template 1 | 116 | GCTTCCTTGCTGGTCAGATTGGTCGTCTTATTACCAT TTCAACTACTCCGGTTATCGCTGGCGACTCCTTCGA GATGGACGCCGTTGGCGCTCTCCGTCTTTCTCCATT GCGTCGT (SEQ ID NO: 1) |

TABLE 1-continued

Templates subjected to sequencing-dark cycles.

| Template | Length | Sequences |
|---|---|---|
| template 2 | 193 | ATTGTTCGCGTTTACCTTGCGTGTACGCGCAGGAAA<br>CACTGACGTTCTTACTGACGCAGAAGAAAACGTGC<br>GTCAAAAATTACGTGCGGAAGGAGTGATGTAATGT<br>CTAAAGGTAAAAAACGTTCTGGCGCTCGCCCTGGTC<br>GTCCGCAGCCGTTGCGAGGTACTAAAGGCAAGCGT<br>AAAGGCGCTCGTCTTT (SEQ ID NO: 2) |
| template 3 | 297 | TGACATTTTAAAAGAGCGTGGATTACTATCTGAGTC<br>CGATGCTGTTCAACCACTAATAGGTAAGAAATCAT<br>GAGTCAAGTTACTGAACAATCCGTACGTTTCCAGAC<br>CGCTTTGGCCTCTATTAAGCTCATTCAGGCTTCTGC<br>CGTTTTGGATTTAACCGAAGATGATTTCGATTTTCT<br>GACGAGTAACAAAGTTTGGATTGCTACTGACCGCTC<br>TCGTGCTCGTCGCTGCGTTGAGGCTTGCGTTTATGG<br>TACGCTGGACTTTGTGGGATACCCTCGCTTTCCTGC<br>TCCTGTTGAG (SEQ ID NO: 3) |
| template 4 | 394 | TCAAGATGATGCTCGTTATGGTTTCCGTTGCTGCCA<br>TCTCAAAAACATTTGGACTGCTCCGCTTCCTCCTGA<br>GACTGAGCTTTCTCGCCAAATGACGACTTCTACCAC<br>ATCTATTGACATTATGGGTCTGCAAGCTGCTTATGC<br>TAATTTGCATACTGACCAAGAACGTGATTACTTCAT<br>GCAGCGTTACCATGATGTTATTTCTTCATTTGGAGG<br>TAAAACCTCTTATGACGCTGACAACCGTCCTTTACT<br>TGTCATGCGCTCTAATCTCTGGGCATCTGGCTATGA<br>TGTTGATGGAACTGACCAAACGTCGTTAGGCCAGTT<br>TTCTGGTCGTGTTCAACAGACCTATAAACATTCTGT<br>GCCGCGTTTCTTTGTTCCTGAGCATGGCACTATG<br>(SEQ ID NO: 4) |
| template 5 | 277 | CGTTCGTCAAGGACTGGTTTAGATATGAGTCACATT<br>TTGTTCATGGTAGAGATTCTCTTGTTGACATTTTAA<br>AAGAGCGTGGATTACTATCTGAGTCCGATGCTGTTC<br>AACCACTAATAGGTAAGAAATCATGAGTCAAGTTA<br>CTGAACAATCCGTACGTTTCCAGACCGCTTTGGCCT<br>CTATTAAGCTCATTCAGGCTTCTGCCGTTTTGGATTT<br>AACCGAAGATGATTTCGATTTTCTGACGAGTAACAA<br>AGTTTGGATTGCTACTGACCGCTCT (SEQ ID NO: 5) |
| template 6 | 259 | CCTTTCGCCATCAACTAACGATTCTGTCAAAACTG<br>ACGCGTTGGATGAGGAGAAGTGGCTTAATATGCTT<br>GGCACGTTCGTCAAGGACTGGTTTAGATATGAGTCA<br>CATTTTGTTCATGGTAGAGATTCTCTTGTTGACATTT<br>TAAAAGAGCGTGGATTACTATCTGAGTCCGATGCTG<br>TTCAACCACTAATAGGTAAGAAATCATGAGTCAAG<br>TTACTGAACAATCCGTACGTTTCCAGACCGCTTTGG<br>CCTCTATT (SEQ ID NO: 6) |
| template 7 | 291 | CTGCCGTTTTGGATTTAACCGAAGATGATTTCGATT<br>TTCTGACGAGTAACAAAGTTTGGATTGCTACTGACC<br>GCTCTCGTGCTCGTCGCTGCGTTGAGGCTTGCGTTT<br>ATGGTACGCTGGACTTTGTGGGATACCCTCGCTTTC<br>CTGCTCCTGTTGAGTTTATTGCTGCCGTCATTGCTTA<br>TTATGTTCATCCCGTCAACATTCAAACGGCCTGTCT<br>CATCATGGAAGGCGCTGAATTTACGGAAAACATTA<br>TTAATGGCGTCGAGCGTCCGGTTAAAGCCGCTGAAT<br>TGT (SEQ ID NO: 7) |
| template 8 | 398 | ACATTCAAACGGCCTGTCTCATCATGGAAGGCGCTG<br>AATTTACGGAAAACATTATTAATGGCGTCGAGCGTC<br>CGGTTAAAGCCGCTGAATTGTTCGCGTTTACCTTGC<br>GTGTACGCGCAGGAAACACTGACGTTCTTACTGAC<br>GCAGAAGAAAACGTGCGTCAAAAATTACGTGCGGA<br>AGGAGTGATGTAATGTCTAAAGGTAAAAAACGTTC<br>TGGCGCTCGCCCTGGTCGTCCGCAGCCGTTGCGAGG<br>TACTAAAGGCAAGCGTAAAGGCGCTCGTCTTTGGT<br>ATGTAGGTGGTCAACAATTTTAATTGCAGGGGCTTC<br>GGCCCCTTACTTGAGGATAAATTATGCTAATATTC<br>AAACTGGCGCCGAGCGTATGCCGCATGACCTTTCCC<br>ATCTTG (SEQ ID NO: 8) |

Upon initiating the first series of sequencing cycles, all of the templates are in sync (i.e., all 10 nucleotides are sequenced and correspond to the first 10 nucleotides). Once the reaction conditions are changed to initiate a limited-extension cycle, the cycles may become out of sync. This can be observed when comparing the templates, as depicted in Table 2, where a truncated sequence (nucleotides 10-18) for each template is reported. These templates are subjected to 10 cycles of sequencing so the identity of the first 10 bases are identified, and beginning with base 11, native nucleotides are incorporated until a $C_t$ is incorporated. Note that even when the number of dark cycles is held constant (e.g., 8 dark cycles used in this example) the length of the dark extension strands may independently vary, depending on how many nucleotides are complementary to the reversibly terminated nucleotide present in the template nucleic acid. The number of terminated nucleotides incorporated into the complementary strand corresponds to the number of dark cycles.

Truncated templates, showing bases 10-18 of the templates 1-8 are depicted in Table 2. The sequencing cycle ceases at cycle 10, and the reaction conditions are changed such that native nucleotides are incorporated at base 11. The bases in bold are terminated and the polymerase is unable to continue incorporating nucleotides until a cleaving agent removes the reversible terminator.

TABLE 2

| Template | 10 | 11 | 12 | 13 | 14 | 15 | 16 | 17 | 18 | LE cycle |
|---|---|---|---|---|---|---|---|---|---|---|
| 1 | C | T | G | G | T | $C_t$ | A | G | A | 1 |
| 2 | G | T | T | T | A | $C_t$ | $C_t$ | T | T | 2 |
| 3 | A | A | A | A | G | A | G | $C_t$ | G | 1 |
| 4 | T | G | C | T | $C_t$ | G | T | T | A | 1 |
| 5 | A | G | G | A | $C_t$ | T | G | G | T | 1 |
| 6 | A | T | C | A | A | $C_t$ | T | A | A | 1 |
| 7 | T | G | G | A | T | T | T | A | A | 0 |
| 8 | C | G | G | $C_t$ | $C_t$ | T | G | T | $C_t$ | 3 |

While the lengths of the templates differ, all of the templates were subjected to the same number of sequencing and limited-extension cycles. Following 10 sequencing cycles, 8 dark cycles, 10 sequencing cycles, 8 dark cycles, 10 sequencing cycles, 8 dark cycles, 10 sequencing cycles, 8 dark cycles, 10 sequencing cycles, and 8 dark cycles, the true-sequenced length (i.e., the last base number identified) for each template is reported in Table 3. Within Table 3, traditional SBS techniques are defined as consecutive sequencing cycles without any dark cycles.

Using traditional SBS techniques (i.e., 50 consecutive sequencing cycles without any LE cycles), the true-sequenced length would be 50 for all templates. Using the methods described herein, significantly more information may be gained about the template nucleic acid sequence. When combined with the massive parallelization that next generation sequencing affords, as depicted in FIG. 3, sequencing of longer template nucleic acids for the same amount of sequencing time becomes possible.

TABLE 3

Reporting on the percent of the template sequenced using the methods described herein.

| Template | Actual length | True-sequenced length | Percent read using traditional SBS | Percent read using methods described herein |
|---|---|---|---|---|
| Template 1 | 116 | 116 | 43.10% | 100.00% |
| Template 2 | 193 | 193 | 25.91% | 100.00% |
| Template 3 | 297 | 216 | 16.84% | 72.73% |
| Template 4 | 394 | 166 | 12.69% | 42.13% |
| Template 5 | 277 | 173 | 18.05% | 62.45% |
| Template 6 | 259 | 182 | 19.31% | 70.27% |
| Template 7 | 291 | 202 | 17.18% | 69.42% |
| Template 8 | 398 | 185 | 12.56% | 46.48% |

REFERENCES FOR EXAMPLES 1 AND 2

1. Bentley D R, et al. Nature, 2008, 456, 53-59
2. U.S. Pat. No. 6,664,079
3. Ju et al. Proc. Natl. Acad. Sci. USA, 2006, 103, 19635-19640
4. de Koning et al. PLoS Genet 7.12 (2011): e100238
5. Deininger, P. Genome Biology 2011 12:236

Example 3: T-Cell and B-Cell Receptor Repertoire Sequencing

The functions of immune cells such as B- and T-cells are predicated on the recognition through specialized receptors of specific targets (antigens) in pathogens. There are approximately $10^{10}$-$10^{11}$ B-cells and $10^{11}$ T-cells in a human adult (Ganusov V V, De Boer R J. Trends Immunol. 2007; 28(12):514-8; and Bains I, Antia R, Callard R, Yates A J. Blood. 2009; 113(22): 5480-5487).

Figure 5A:
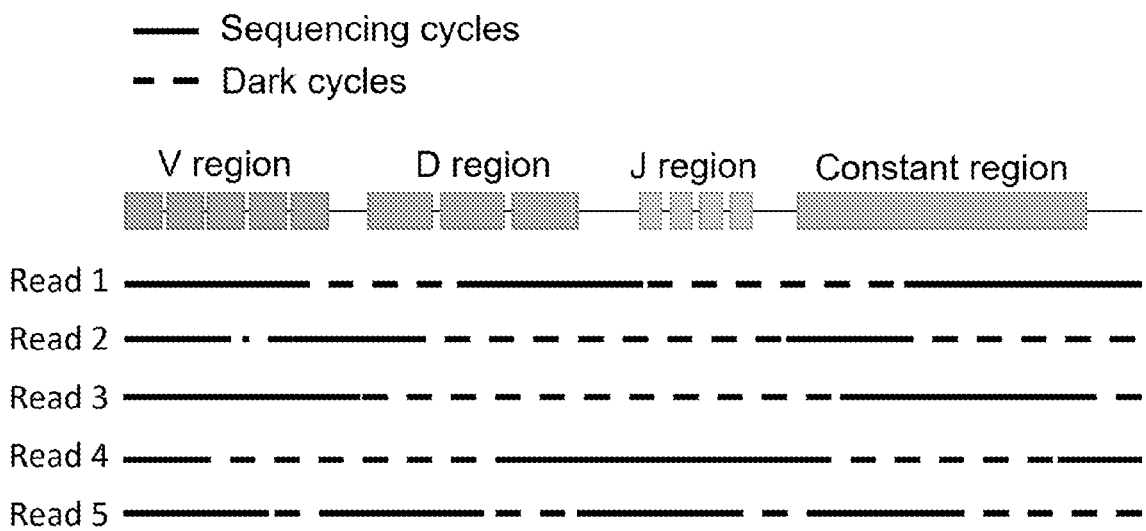
FIGS. 5A-5C illustrate the gene segments of a variable (V), joining (J), diversity (D), and constant (C) region, which confers the isotype to an antibody (see FIG. 5A). Utilizing the methods described herein, comprehensive snapshots of the repertoire diversity for each class of antibody may be realized by sequencing a portion of the constant region to determine the isotype, then alternating dark cycles (indicated as dashed lines in FIGS. 5A and 5B) and sequencing cycles (indicated as solid lines in FIGS. 5A and 5B) to obtain a comprehensive view of the C-V-D-J segments.

Immune cells are critical components of adaptive immunity and directly bind to pathogens through antigen-binding regions present on the cells. Within lymphoid organs (e.g., bone marrow for B cells and the thymus for T cells) the gene segments variable (V), joining (J), and diversity (D) rearrange to produce a novel amino acid sequence in the antigen-binding regions of antibodies that allow for the recognition of antigens from a range of pathogens (e.g., bacteria, viruses, parasites, and worms) as well as antigens arising from cancer cells. The large number of possible V-D-J segments, combined with additional (junctional) diversity, lead to a theoretical diversity of $>10^{14}$, which is further increased during adaptive immune responses. Overall, the result is that each B- and T-cell expresses a practically unique receptor, whose sequence is the outcome of both germline and somatic diversity. These antibodies also contain a constant (C) region, which confers the isotype to the antibody (see FIG. 5A). In most mammals, there are five antibody isotypes: IgA, IgD, IgE, IgG, and IgM. For example, each antibody in the IgA isotype shares the same constant region.

Figure 5B:
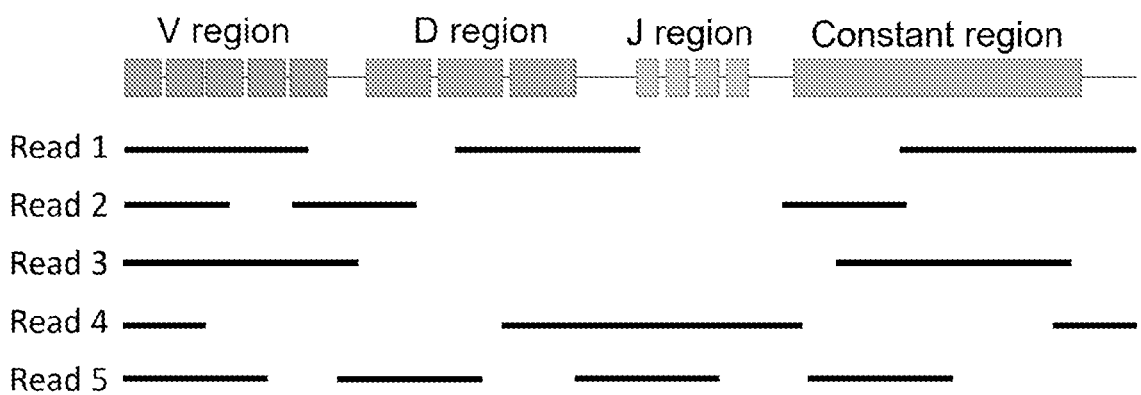
Figure 5C:
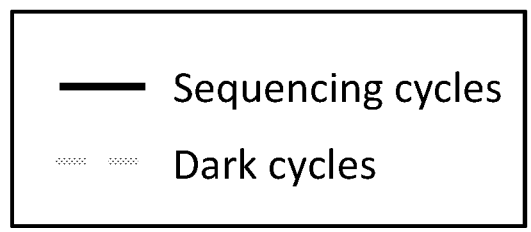
Figure 5C:
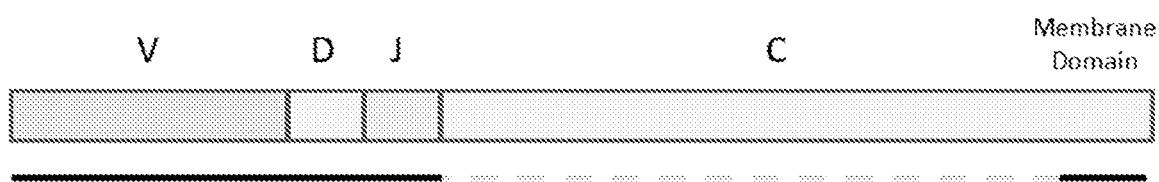

While parts of the B-cell immunoglobulin receptor (BCR) can be traced back to segments encoded in the germline (i.e., the V, D and J segments), the set of segments used by each receptor is something that needs to be determined as it is coded in a highly repetitive region of the genome (Yaari G, Kleinstein S H. Practical guidelines for B-cell receptor repertoire sequencing analysis. Genome Med. 2015; 7:121. (2015)). Additionally, there are no pre-existing full-length templates to align the sequencing reads. Thus, obtaining long-range sequence data is incredibly insightful to gain insights into the adaptive immune response in healthy individuals and in those with a wide range of diseases. Utilizing the methods described herein, comprehensive snapshots of the repertoire diversity for each class of antibody may be realized by sequencing a portion of the constant region sufficient to determine the isotype and/or to determine whether a transmembrane domain is present, whereby the transmembrane domain is indicative of a surface bound receptor or secreted immunoglobulin, applying multiple dark cycles to rapidly extend the elongating strand to the joining gene, then applying sequencing cycles to obtain a comprehensive readout of the V-D-J segments, which determine the antigen specificity of the surface bound receptor or secreted immunoglobulin (see FIG. 5C). In embodiments, the method includes alternating dark and sequencing cycles to obtain a comprehensive view of the C-V-D-J segments, for example see FIGS. 5A-5B for an overview of this process and subsequent sequencing results, in accordance with some embodiments.

Sample library preparation involves the isolation and amplification of the target nucleic acid fragments for sequencing. Briefly, B cells are separated from the starting tissue (e.g., anticoagulated whole blood containing B cells). There are two starting materials that can serve as the initial template to sequence immunoglobulin (Ig) repertoires—genomic DNA (gDNA) and mRNA. In the example above, RNA input would be used as splicing eliminates large introns within the rearranged receptor, resulting in a constant gene region sequence that directly flanks the rearranged V-D-J. RNA is converted to cDNA by reverse transcription; in some embodiments, RNA derived from B cells may be selectively converted to cDNA using oligomers targeting the 3' most region of the isotype. Optionally, IGH cDNA may be amplified by PCR, followed by NGS library preparation according to known techniques in the art, then subjected to alternating sequencing and dark cycles (e.g., the interval sequencing protocols) as described herein.

Example 4: Metagenomics and Profiling Bacteria

The study of bacterial phylogeny and taxonomy by analyzing the 16S rRNA gene has become popular among microbiologists due to the need to study the diversity and structure of microbiomes thriving in specific ecosystems. Due to its presence in almost all bacteria, the 16S rRNA gene is a core component of the 30S small subunit of prokaryotes. The 16S sequence contains ten conserved (C) regions that are separated by nine variable (V1-V9) regions, wherein the V regions are useful for taxonomic identification. Due to limitations in previous NGS platforms, the entirety of the 16S gene (approximately 1,500 bp) is difficult to accurately sequence.

Clever design of primers have been reported and used for amplifying specific V regions of 16S rRNA; for example, the third, fourth, and fifth variable regions (V3, V4 and V5 regions, respectively) have been used for studies where classification and understanding phylogenic relationships is important (see for example, Baker G. C., et al J. of Microbiological Methods, V55 (2003), 541-555; and Wang, Y., et al. (2014). PloS one, 9(3), e90053). While the information gained from sequencing the V3 or V4 region is valuable, no single variable region can differentiate among all bacteria. For example, the V1 region has been demonstrated to be particularly useful for differentiating among species in the genus *Staphylococcus*, whereas V2 distinguished among Mycobacterial species and V3 among *Haemophilus* species (Chakravorty, S., et al (2007). Journal of microbiological methods, 69(2), 330-339). It would therefore be very beneficial to be able to sequence the entirety of the 16s gene without having to a priori select appropriate primer sets. The methods described herein provide a new method for sequencing the 16S rRNA gene in its entirety, including the constant and nine variable regions, permitting species level identification.

Figure 6:
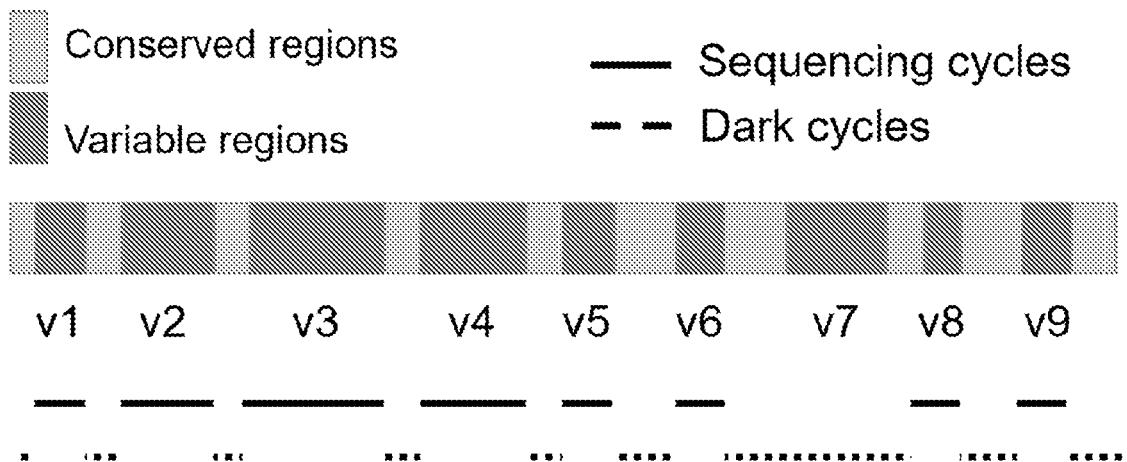
FIG. 6 illustrates a 16S rRNA variable and conserved gene segment. The 16S sequence contains ten conserved (C) regions that are separated by nine variable (V1-V9) regions, wherein the V regions are useful for taxonomic identification. Using methods described herein (e.g., alternating a plurality of sequencing cycles and a plurality of dark cycles), provides valuable insight into the entirety of the 16S rRNA gene. Depicted below the 16S gene and the variable labels in FIG. 6 are dashed lines representing extensions generated during a plurality of dark cycles which are offset from the solid lines representing a sequencing read from a plurality of sequencing cycles. Note, the identity of the nucleotides is not determined in a dark cycle and a read is not necessarily produced.
Figure 7:
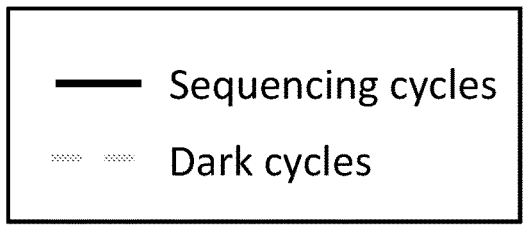
FIG. 7. Detection of a structural variant by an embodiment of interval sequencing methods described herein. For example, depicted in FIG. 7 is a sample containing a genomic rearrangement fusing Region 1 with Region 2 (e.g., a gene fusion event). An embodiment of interval sequencing as described herein is applied, followed by mapping of each interval region to a reference genome. Mapping reveals presence of a breakpoint fusing Region 1 with Region 2.
Figure 7:
Figure 8:
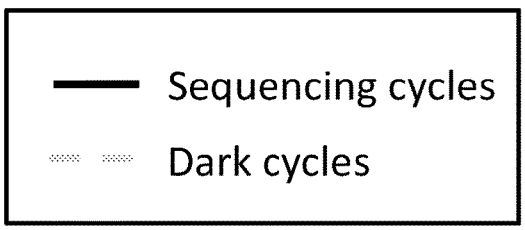
FIG. 8. Reconstruction of the entire sequence region presented in FIG. 7 by alignment and consensus assembly. An embodiment of internal sequencing methods as described herein is applied whereby a plurality of reads cover a region of interest, such that the sequencing intervals are staggered and complementary. Consensus assembly of the sequence fragments produces the full sequence of the region, precisely mapping the breakpoint junction.
Figure 8:
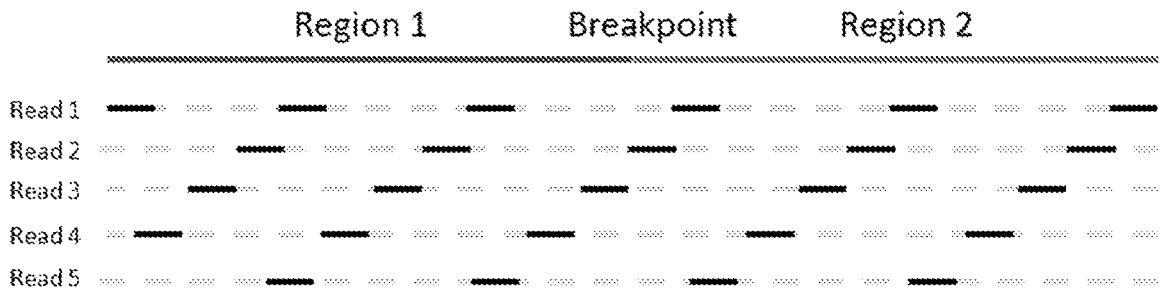
Figure 9:
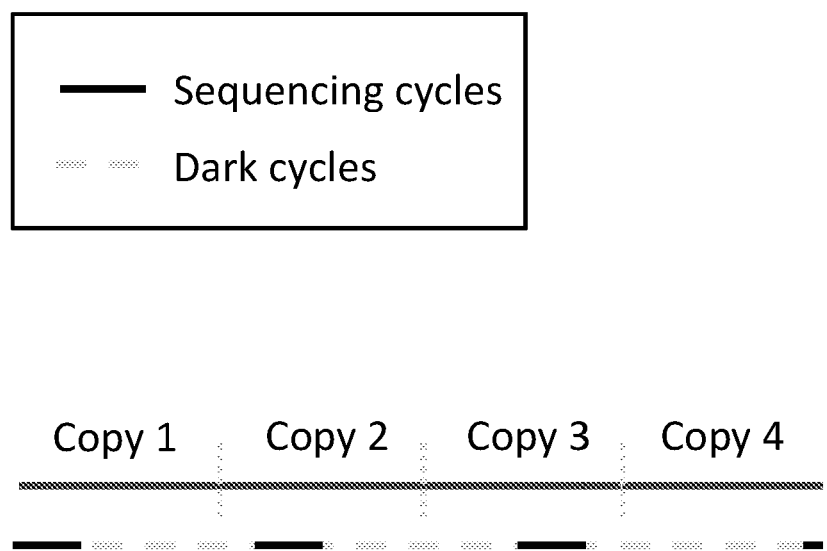
FIG. 9. Interval sequencing-based reconstruction of an entire region of interest represented as tandemly arranged copies. In the illustrated embodiment, a single interval read sequences different and complementary portions of tandemly arranged copies of a region, permitting reconstruction of the entire sequence of the region of interest.

Briefly, an isolated RNA molecule (e.g., mRNA), may be further purified and selected for 16S rRNA sequencing. The RNA may be reverse transcribed to cDNA, followed by a DNA polymerase-mediated second strand synthesis to yield an input DNA molecule. It is known that RNA representation bias can be introduced with the generation of cDNA; therefore it may be preferable to use the RNA as the template directly. The target nucleic acid may be amplified using known methods in the art (e.g., standard PCR amplification) and subjected to standard library preparation methods as known in the art. The amplified template strand may be subjected to the interval sequencing methods as described herein. For example, alternating series of dark and sequencing cycles, preferably using a majority of LE cycles during the constant regions and using a majority of sequencing cycles during the variable regions, will help shed insight into the entirety of the 16S rRNA gene and allow for bacterial species identification. See FIG. 6 for an illustration of the 16S gene.

Example 5: De Novo Assembly of Bacterial Genomes

Microbial genome sequencing has revealed how microorganisms adapt, evolve, and contribute to health and disease. With respect to bacterial genomes, the de novo assembly of short reads (100-300 bp) can result in fragmented assemblies, particularly because of the widespread presence of repetitive sequences. These repetitive sequences are often longer than the length of a short read and the span of paired-end reads. For example, antimicrobial resistance regions are often flanked by repetitive insertion sequences; in such a case, from an incomplete short-read assembly, it would be impossible to determine whether resistance regions are present in chromosomes or plasmids (Liao Y C et al. Front. Microbiol. 2019; 10:2068). As such, faithful de novo assembly of bacterial genomes typically requires larger inserts, for example, 1 kbp or larger.

Existing methods for de novo bacterial genome assembly include the use of long-read sequencing technology such as that of Pacific Biosciences and Oxford Nanopore, both of which report higher error rates and lower throughput in comparison to other sequencing methods (e.g., sequencing-by-synthesis technologies). Alternatively, large-scale genome assembly can use mate pair sequencing to generate long-insert paired-end DNA libraries, however the relatively laborious and lengthy protocol that generates long insert sizes needed for mate pair sequencing typically produces a large proportion of duplicates and chimeric variants that reduces true coverage and insight. Still, a major challenge is the higher rate of sequencing errors abundant in these existing methods, in combination with base composition bias and the complexity of repetitive regions in genomes, leading to complicated and unsatisfactory sequence assembly (Liao X et al. Quant. Biol. 2019; 7(2):90-109). The methods described herein address these and other problems. For example, the compositions and sequencing methods described herein will allow for high-accuracy pairwise sequencing of large-insert genomic libraries.

Bacterial genomic DNA is purified from isolated cultures using a commercial solution, such as the NEB Monarch® Genomic DNA Purification Kit (Cat. No. T30105). The extracted genomic DNA is fragmented to an average size of approximately 1000 bp by acoustic shearing (Covaris). The fragments are subjected to standard library preparation methods as known in the art. The amplified genomic fragments are then subjected to the interval sequencing methods as described herein. Following sequencing and acquiring the resulting reads, these reads are then assembled using bioinformatic tools known in the art to generate the complete bacterial genome. These methods could also be applied to other prokaryotic and eukaryotic de novo genome assembly efforts.

Example 6: Alternative Splicing Analysis

Alternative splicing (AS) is a key post-transcriptional regulatory mechanism in which alternative splice sites are selected to generate more than one transcript from heterogenous nuclear RNA (hnRNA) transcripts (Wahl M C Cell 2009; 136:701-718). During AS, intronic sequences are defined by the dinucleotide conserved sequence motifs at the intron/exon junctions, usually GT-AG, which are respectively named as 5' donor site and 3' acceptor site. Other intron/exon junction dinucleotide sequence motifs have also been reported, including AT-AC, GC-AG, and GT-GG (Dubrovina A S et al. Biomed. Res. Int. 2013). Different transcript isoforms may encode proteins with different functions or affect the mRNA stability of translational capacity. For multiexon mRNA, the splicing mode may vary in multiple ways, including intron retention, exon skipping, and alternative donor/acceptor sites, dramatically increasing the complexity of the entire transcriptome and proteome (Li Y et al. The Plant J. 2016; 90(1):164-176).

Accurate detection of AS events remains a challenge due to the limitations of short-read sequences in reconstructing full-length isoforms (Hu H et al. Front. Genet. 2020; 11:48). These disadvantages generally lead to gene prediction without reliable annotation on alternative isoforms and untranslated regions, which can limit their use to characterize the post-transcriptional processes. Therefore, the identification of full-length splice isoforms is essential for a deep understanding of the transcriptome complexity and its potential role in gene regulation. Much like de novo bacterial genome assembly (see Example 5), AS detection will benefit from a longer insert size and reliable capture of AS-related motifs. A comparison between PacBio's SMRT sequencing and Illumina's RNA-seq platforms (Li Y et al. The Plant J. 2016; 90(1):164-176) indicated that SMRT, which utilizes longer read-length technology, was able to identify more genes undergoing AS than standard RNA-seq, although still lacked reliable capture of all known AS events. The sequencing method described herein allows for high-accuracy RNA sequencing of a large-insert library to enable efficient AS site detection.

Briefly, total RNA is extracted from a sample for AS analysis using a commercial solution such as the RNeasy Mini Kit (Qiagen). Ribosomal RNA (rRNA) is then depleted using a commercial solution such as the NEBNext® rRNA Depletion Kit V2 (Cat. No. E7405S). While polyA+ selection is typically used for RNA-seq protocols, rRNA depletion has been shown to capture significantly more transcriptome features useful for AS analysis (see, for example, Zhao S et al. Scientific Reports 2018; 8: 4781). The RNA is then fragmented to an average size of greater than 200 bases, for example, approximately 200-300 bases, or approximately 300-400 bases, or approximately 400-500 bases, or approximately 500-600 bases, or approximately 600-700 bases, or approximately 700-800 bases, using standard methods for RNA fragmentation such as acoustic shearing (Covaris) or incubation with divalent cations, e.g. Mg2+, at elevated temperatures.

The fragmented RNA is then reverse transcribed and converted to double-stranded cDNA using commercial solutions, for example, the Invitrogen™ SuperScript™ Double-Stranded cDNA Synthesis Kit (Cat. No. 11917010). A library is prepared and amplified from the cDNA using methods known in the art and subjected to the interval sequencing methods as described herein.

Following sequencing of cDNA and acquiring the resulting reads, the identification of major AS events, including exon skipping events, intron retention, alternative 5' donor, and alternative 3' donor usage can be accomplished through bioinformatic analysis, including the use of publicly available tools such as JUM (Wang Q and Rio D C Proc. Natl. Acad. Sci. 2018; 115(35):E8181-E8190) and PASA (Campbell M A et al. BMC Genomics 2006; 7:327). Identified AS events can then be cross-checked with known AS databases and reference genomes.

P-EMBODIMENTS

The present disclosure provides the following illustrative embodiments.

Embodiment P1. A method of sequencing a template nucleic acid, the method comprising: (a) executing a sequencing cycle comprising (i) extending a complementary polynucleotide that is hybridized to the template nucleic acid by incorporating a first nucleotide using a polymerase; and (ii) detecting a label that identifies the first nucleotide; (b) extending the complementary polynucleotide in one or more dark cycles, wherein each dark cycle comprises extending the complementary polynucleotide by one or more nucleotides using the polymerase, without performing a detection event to identify nucleotides incorporated during the dark cycle; and (c) executing a sequencing cycle comprising (i) extending the complementary polynucleotide by incorporating a second nucleotide using a polymerase; and (ii) detecting a label that identifies the second nucleotide, thereby sequencing a template nucleic acid.

Embodiment P2. A method of sequencing a template nucleic acid, the method comprising: (a) executing a sequencing cycle comprising (i) extending a complementary polynucleotide that is hybridized to the template nucleic acid by incorporating a first nucleotide using a polymerase; wherein said nucleotide comprises a reversible terminator moiety, and (ii) detecting a label that identifies the first nucleotide; (b) extending the complementary polynucleotide in one or more dark cycles, wherein each dark cycle comprises extending the complementary polynucleotide by at least two nucleotides using the polymerase; wherein at least one nucleotide does not comprise a reversible terminator, and one nucleotide comprises a reversible terminator moiety, optionally performing a detection event to identify nucleotides incorporated during the dark cycle; and (c) executing a sequencing cycle comprising (i) extending the complementary polynucleotide by incorporating a second nucleotide using a polymerase; wherein said nucleotide comprises a reversible terminator moiety, and (ii) detecting a label that identifies the second nucleotide, thereby sequencing a template nucleic acid.

Embodiment P3. The method of Embodiment P1, wherein the method comprises extending the complementary polynucleotide in one or more dark cycles, wherein each dark cycle comprises extending the complementary polynucleotide by one or more nucleotides using the polymerase, without performing a detection event to identify nucleotides incorporated during a dark cycle before step (a).

Embodiment P4. The method of Embodiment P2, wherein the method comprises extending the complementary polynucleotide in one or more dark cycles, wherein each dark cycle comprises extending the complementary polynucleotide by at least two nucleotides using the polymerase; wherein at least one nucleotide does not comprise a reversible terminator, and one nucleotide comprises a reversible terminator moiety, optionally performing a detection event to identify nucleotides incorporated during the dark cycle; and incorporated during a dark cycle before step (a).

Embodiment P5. The method of Embodiment P1 or Embodiment P2, further comprising, (d) repeating step (b).

Embodiment P6. The method of one of Embodiment P1 to Embodiment P5, wherein step (a) further comprises (iii) repeating steps (i) and (ii) one or more times.

Embodiment P7. The method of one of Embodiment P1 to Embodiment P6, wherein step (c) further comprises (iii) repeating steps (i) and (ii) one or more times.

Embodiment P8. The method of one of Embodiment P5 to Embodiment P7, further comprising repeating steps (a) to (d) one or more times.

Embodiment P9. The method of one of Embodiment P1 to Embodiment P8, wherein the first and second nucleotides each comprise an identifying label.

Embodiment P10. The method of one of Embodiment P1 to Embodiment P9, wherein the first and second nucleotides each comprise a reversible terminator, and the method further comprises removing the reversible terminator after said detecting.

Embodiment P11. The method of one of Embodiment P1 to Embodiment P10, wherein a dark cycle terminates with the addition of a nucleotide comprising a reversible terminator.

Embodiment P12. The method of Embodiment P11, comprising a plurality of dark cycles.

Embodiment P13. The method of Embodiment P12, wherein the nucleotide comprising the reversible terminator is the same type in the plurality of dark cycles.

Embodiment P14. The method of one of Embodiment P1 to Embodiment P13, wherein four different nucleotides are present during said extending steps and each is labeled differently.

Embodiment P15. The method of one of Embodiment P1 to Embodiment P14, wherein the label is a fluorescent label.

Embodiment P16. The method of one of Embodiment P1 to Embodiment P15, wherein the method comprises a total number of sequencing cycles of about 20 to about 50.

Embodiment P17. The method of one of Embodiment P1 to Embodiment P16, wherein the total number of dark cycles is about 20 to about 50.

Embodiment P18. The method of one of Embodiment P1 to Embodiment P17, wherein the method produces one or more sequencing reads comprising joined discontinuous nucleic acid sequences collectively spanning a length of about 500 to about 1000 bases of the template nucleic acid.

Embodiment P19. The method of Embodiment P18, further comprising aligning the one or more sequencing reads to a reference sequence.

Embodiment P20. The method of Embodiment P19, further comprising generating a consensus sequence from the aligned one or more sequencing reads.

Embodiment P21. The method of Embodiment P20, wherein the consensus sequence comprises (i) a nucleic acid sequence in one or more first sequencing reads that is absent from one or more second sequencing reads, and (ii) a nucleic acid sequence in one or more of the second sequencing reads that is absent from the one or more first sequencing reads.

Embodiment P22. The method of one of Embodiment P1 to Embodiment P21, wherein each sequencing cycle comprises contacting the complementary polynucleotide with a sequencing solution, wherein said sequencing solution comprises one or more nucleotides, wherein each nucleotide comprises a detectable label and a reversible terminator.

Embodiment P23. The method of Embodiment P22, wherein said sequencing solution comprises a. an adenine nucleotide, or analog thereof; b. (i) a thymine nucleotide, or analog thereof, or (ii) a uracil nucleotide, or analog thereof; c. a cytosine nucleotide, or analog thereof; and d. a guanine nucleotide, or analog thereof.

Embodiment P24. The method of one of Embodiment P1 to Embodiment P23, wherein each dark cycle comprises contacting the complementary polynucleotide with a dark solution, wherein said dark solution comprises one or more nucleotides, wherein at least one nucleotide comprises a reversible terminator.

Embodiment P25. The method of Embodiment P24, wherein said dark solution comprises a. an adenine nucleotide, or analog thereof; b. (i) a thymine nucleotide, or analog thereof, or (ii) a uracil nucleotide, or analog thereof; c. a cytosine nucleotide, or analog thereof; and d. a guanine nucleotide, or analog thereof.

Embodiment P26. The method of Embodiment P21 or Embodiment P22, wherein one nucleotide comprises a reversible terminator.

Embodiment P27. A kit comprising (a) labeled nucleotides comprising four differently labeled nucleotides, wherein the label identifies the type of nucleotide, (b) unlabeled nucleotides lacking a reversible terminator; and (c) unlabeled nucleotides comprising a reversible terminator.

Embodiment P28. The kit of Embodiment P27, further comprising (d) a polymerase.

Embodiment P29. A reaction mixture comprising (a) labeled nucleotides comprising four differently labeled nucleotides, wherein the label identifies the type of nucleotide, (b) unlabeled nucleotides lacking a reversible terminator; (c) unlabeled nucleotides comprising a reversible terminator; and (d) a polymerase.

Embodiment P30. A method of sequencing a template nucleic acid, the method comprising: (a) executing a sequencing cycle comprising (i) extending a complementary polynucleotide that is hybridized to the template nucleic acid by incorporating a first nucleotide using a polymerase; and (ii) detecting a characteristic signature indicating that the first nucleotide has been incorporated; (b) extending the complementary polynucleotide in one or more dark cycles, wherein each dark cycle comprises extending the complementary polynucleotide by one or more nucleotides using the polymerase, without applying a detection process to identify nucleotides incorporated during the dark cycle; and (c) executing a sequencing cycle comprising (i) extending the complementary polynucleotide by incorporating a second nucleotide using a polymerase; and (ii) detecting a characteristic signature that identifies the second nucleotide, thereby sequencing a template nucleic acid.

Embodiment P31. The method of one of embodiments P1 to P26 or P30, wherein each dark cycle comprises extending the complementary polynucleotide by incorporating with a polymerase a nucleotide from a limited-extension solution, wherein the limited-extension solution comprises a plurality of nucleotides or analogs thereof wherein one to three of the following plurality of nucleotides or analogs thereof is absent: (a) adenine nucleotides and analogs thereof; (b) (i) thymine nucleotides and analogs thereof, and (ii) uracil nucleotides and analogs thereof; (c) cytosine nucleotides and analogs thereof, or (d) guanine nucleotides and analogs thereof.

Embodiment P32. The method of embodiments P31, wherein each nucleotide or analog thereof of the limited-extension solution comprises a reversible terminator, a label, or both, and the limited-extension solution is contacted by a cleaving agent prior to, during, or following incorporating nucleotides in the one or more dark cycles.

Embodiment P33. The method of embodiments P31 or P32, wherein the limited-extension solution is contacted by a cleaving agent prior to incorporating.

Embodiment P34. The method of one of embodiments P30 to P33, step (b) comprises a plurality of dark cycles.

Embodiment P35. The method of one of embodiments P1 to P26 or P30 to P34, wherein each sequencing cycle comprises contacting the complementary polynucleotide with a sequencing solution, wherein said sequencing solution comprises one or more nucleotides, wherein each nucleotide comprises a reversible terminator.

Embodiment P36. The method of Embodiment P24, wherein said dark solution comprises a plurality of one to three of nucleotide types selected from the following: a. a plurality of adenine nucleotides, or analogs thereof; b. (i) a plurality of thymine nucleotides, or analogs thereof, or (ii) a plurality of uracil nucleotides, or analogs thereof; c. a plurality of cytosine nucleotides, or analogs thereof; and d. a plurality of guanine nucleotides, or analogs thereof.

Embodiment P37. The method of one of embodiments P1 to P26 or P30 to P36, wherein the method produces one or more sequencing reads comprising joined discontinuous nucleic acid sequences collectively spanning a length of more than 1 kb, 2 kb, 3 kb, 4 kb, or 5 kb of the template nucleic acid.

Embodiment P38. The method of one of embodiments P1 to P26 or P30 to P36, wherein the method produces one or more sequencing reads comprising joined discontinuous nucleic acid sequences collectively spanning a length of more than 5 kb, 6 kb, 7 kb, 8 kb, 9 kb, or 10 kb of the template nucleic acid.

Embodiment P39. The method of one of embodiments P1 to P26 or P30 to P36, wherein the method produces one or more sequencing reads comprising joined discontinuous nucleic acid sequences collectively spanning a length of 3 kb to 8 kb of the template nucleic acid.

What is claimed:

1. A method of extending a complementary polynucleotide hybridized to a template nucleic acid, the method comprising:
    (a) contacting the complementary polynucleotide with an extension solution thereby forming an extension strand, wherein said extension solution comprises four nucleotide types, wherein only one of the four nucleotide types comprises a reversible terminator; and
    (b) removing said reversible terminator and repeating step (a) for one or more cycles with said extension solution, wherein the nucleotide comprising the reversible terminator is the same nucleotide type in one or more cycles.

2. The method of claim 1, wherein said four nucleotide types consist of: i) an adenine nucleotide, or analog thereof; ii) a thymine nucleotide, or analog thereof, or a uracil nucleotide, or analog thereof; iii) a cytosine nucleotide, or analog thereof; and iv) a guanine nucleotide, or analog thereof.

3. The method of claim 2, wherein said adenine nucleotide, or analog thereof, comprise the reversible terminator.

4. The method of claim 2, wherein said thymine nucleotide, or analog thereof, comprise the reversible terminator.

5. The method of claim 2, wherein said cytosine nucleotide, or analog thereof, comprise the reversible terminator.

6. The method of claim 2, wherein said guanine nucleotide, or analog thereof, comprise the reversible terminator.

7. The method of claim 1, wherein prior to step a), said method comprises removing a reversible terminator from the complementary polynucleotide by contacting the complementary polynucleotide with a cleaving agent.

8. The method of claim 1, wherein during step a), said method comprises detecting the nucleotides incorporated.

9. The method of claim 1, wherein prior to step a), said method comprises sequencing said template nucleic acid.

10. The method of claim 1, further comprising sequencing said template nucleic acid to generate a sequenced-extension strand.

11. The method of claim 10, further comprising contacting the sequenced-extension strand with the extension solution; and removing said reversible terminator and repeating contacting the sequenced-extension strand with said extension solution for one or more cycles.

12. The method of claim 9, wherein sequencing comprises incorporating one or more labeled nucleotides or labeled nucleotide analogues with a polymerase into the complementary polynucleotide, and detecting the label that identifies the one or more incorporated nucleotides.

13. The method of claim 12, wherein 2 to 150 nucleotides are incorporated.

14. The method of claim 1, wherein the method comprises repeating step (a) for 5 to 50 cycles.

15. The method of claim 1, wherein the method comprises repeating step (a) for 25 to 100 cycles.

16. The method of claim 1, wherein the template nucleic acid is immobilized to a solid support.

17. The method of claim 1, wherein the template nucleic acid is at least 1000 bases (1kb), at least 2 kb, at least 4 kb, at least 6 kb, at least 10 kb, at least 20 kb, at least 30 kb, at least 40 kb, or at least 50 kb in length.

18. The method of claim 10, wherein the method produces one or more sequencing reads comprising joined discontinuous nucleic acid sequences collectively spanning a length of about 100 to about 5000 bases of the template nucleic acid.

19. The method of claim 18, further comprising aligning the one or more sequencing reads to a reference sequence.

20. The method of claim 19, further comprising generating a consensus sequence from the aligning of one or more sequencing reads, wherein the consensus sequence comprises (i) a nucleic acid sequence in one or more first sequencing reads that is absent from one or more second sequencing reads, and (ii) a nucleic acid sequence in one or more of the second sequencing reads that is absent from the one or more first sequencing reads.

21. The method of claim 1, wherein the template nucleic acid is an RNA transcript.

22. The method of claim 1, wherein the template nucleic acid comprises a gene or a gene fragment, wherein the gene or gene fragment is a cancer-associated gene or fragment thereof, T cell receptor (TCR) gene or fragment thereof, or a B cell receptor (BCR) gene, or fragment thereof.

23. The method of claim 10, wherein sequencing comprises incorporating one or more labeled nucleotides or labeled nucleotide analogues with a polymerase into the complementary polynucleotide, and detecting the label that identifies the one or more incorporated nucleotides.

24. The method of claim 1, wherein the template nucleic acid is within a sample comprising cells or tissues.

25. A method of extending a polynucleotide hybridized to a template nucleic acid, the method comprising:
(a) contacting the polynucleotide with a first extension solution thereby forming an extension strand, wherein said first extension solution comprises a plurality of adenine nucleotides, a plurality of thymine nucleotides, a plurality of cytosine nucleotides, and a plurality of guanine nucleotides, wherein the nucleotides of one plurality comprise a reversible terminator;
(b) removing said reversible terminator; and
(c) contacting the polynucleotide with the same extension solution of step (a).

26. The method of claim 25, wherein said template nucleic acid is in a cell or tissue.

27. The method of claim 25, further comprising sequencing said template nucleic acid to generate a sequenced-extension strand.

28. The method of claim 25, wherein steps (a), (b), and (c) comprise a cycle, the method further comprises repeating steps (a), (b), and (c) for 5 to 500 cycles.

29. The method of claim 25, wherein the adenine nucleotides comprise a reversible terminator or the thymine nucleotides comprise a reversible terminator.

30. The method of claim 25, wherein the cytosine nucleotides comprise a reversible terminator or the guanine nucleotides comprise a reversible terminator.

31. The method of claim 25, wherein said template nucleic acid is on a cell.

32. The method of claim 1, wherein the reversible terminator is comprises an azido moiety, a disulfide moiety, or an allyl moiety.

33. The method of claim 1, wherein the reversible terminator comprises the formula:

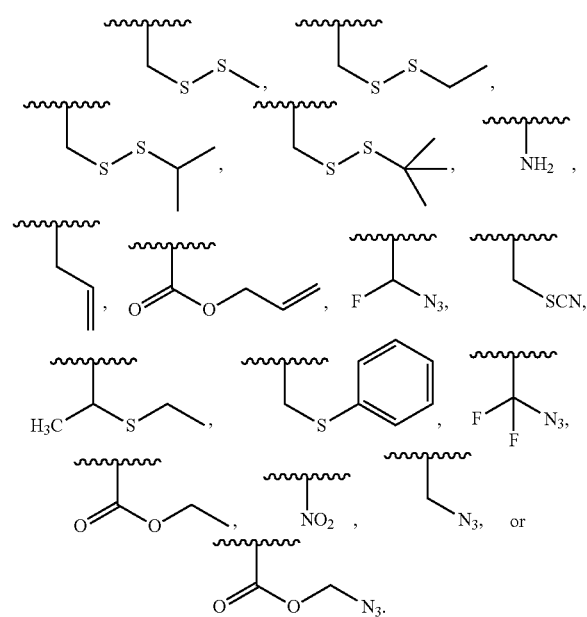

34. The method of claim 1, wherein the reversible terminator is comprises an azido moiety, a disulfide moiety, or an allyl moiety.

35. The method of claim 1, wherein the reversible terminator comprises the formula:

-continued

*  *  *  *  *